US012766260B2

(12) United States Patent
Sjolund et al.

(10) Patent No.: US 12,766,260 B2
(45) Date of Patent: Oct. 20, 2026

(54) SYSTEMS, DEVICES AND RELATED METHODS OF COORDINATING INSULIN MANAGEMENT AND DELIVERY MODES IN FASTING AND NON-FASTING PERIODS

(71) Applicant: LUNA HEALTH, INC., Wilmington, DE (US)

(72) Inventors: Per John Sjolund, San Diego, CA (US); Sean Thomas Saint, San Diego, CA (US); Jack David Pryor, San Diego, CA (US); Lane Desborough, Thousand Oaks, CA (US)

(73) Assignee: Luna Health, Inc., Wilmington, DE (US)

( * ) Notice: Subject to any disclaimer, the term of this patent is extended or adjusted under 35 U.S.C. 154(b) by 543 days.

(21) Appl. No.: 18/135,447

(22) Filed: Apr. 17, 2023

(65) Prior Publication Data

US 2023/0330336 A1 Oct. 19, 2023

Related U.S. Application Data

(60) Provisional application No. 63/332,001, filed on Apr. 18, 2022.

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14244* (2013.01); *G16H 20/17* (2018.01);
(Continued)

(58) Field of Classification Search
CPC ...... A61M 5/1723; A61M 2005/14208; A61M 2205/52; A61M 2230/201; G16H 20/17;
(Continued)

(56) References Cited

U.S. PATENT DOCUMENTS 7,137,964 B2 11/2006 Flaherty
8,062,256 B2 11/2011 Carter et al.
(Continued)

FOREIGN PATENT DOCUMENTS

CN 107073207 B 8/2017
JP 2013516231 A 5/2013
(Continued)

OTHER PUBLICATIONS

Garnica, O., et al., "Noise spectral analysis and error estimation of continuous glucose monitors under real-life conditions of diabetes patients," Biomedical Signal Processing Control, 2020, pp. 1-10, v. 61, Elsevier Ltd.
(Continued)

*Primary Examiner* — David P. Olynick
(74) *Attorney, Agent, or Firm* — Veros Legal Solutions, LLP

(57) ABSTRACT

An insulin management method is provided. The method includes providing an insulin delivery device, wherein the insulin delivery device is in the form of an automatic insulin delivery device attachable to a user's body for the duration of a fasting period. The method includes delivering insulin from the insulin delivery device during the fasting period within an overall time period in the form of correction bolus doses of insulin in response to received blood glucose measurements. The insulin delivery device refrains from administering basal insulin at a preset or default rate or in a preset or default pattern. Insulin is received by the user from a non-fasting insulin management modality during a non-fasting period within the overall time period and the non-fasting insulin management modality provides at least one of a basal dose of insulin and bolus doses of insulin. Other methods, devices and systems are also provided.

27 Claims, 26 Drawing Sheets

(51) Int. Cl.
*G16H 20/17* (2018.01)
*G16H 40/67* (2018.01)

(52) U.S. Cl.
CPC ... *G16H 40/67* (2018.01); *A61M 2005/14208* (2013.01); *A61M 2202/0486* (2013.01); *A61M 2205/52* (2013.01); *A61M 2230/201* (2013.01)

(58) Field of Classification Search
CPC ........ G16H 50/20; G16H 50/30; G16H 40/63; G16H 40/67; G16H 20/10
See application file for complete search history.

(56) References Cited

U.S. PATENT DOCUMENTS

| | | | | |
|---|---|---|---|---|
| 8,147,446 | B2 | 4/2012 | Yodfat et al. | |
| 8,465,460 | B2 | 6/2013 | Yodfat et al. | |
| 8,556,866 | B2 | 10/2013 | Krulevitch et al. | |
| 8,568,361 | B2 | 10/2013 | Yodfat et al. | |
| 8,900,189 | B2 | 12/2014 | Yodfat et al. | |
| 9,089,637 | B2 | 7/2015 | Chong et al. | |
| 9,402,950 | B2 | 8/2016 | Dilanni et al. | |
| 9,457,146 | B2 | 10/2016 | Dobbles et al. | |
| 9,572,935 | B2 | 2/2017 | Dobbles et al. | |
| 9,572,936 | B2 | 2/2017 | Dobbles et al. | |
| 9,597,453 | B2 | 3/2017 | Dobbles et al. | |
| 9,817,372 | B2 | 11/2017 | Schaffrath | |
| 9,827,372 | B2 | 11/2017 | Dobbles et al. | |
| 9,849,239 | B2 | 12/2017 | Grosman et al. | |
| 10,058,691 | B2 | 8/2018 | Yue et al. | |
| 10,105,488 | B2 | 10/2018 | Palerm et al. | |
| 10,275,573 | B2 | 4/2019 | Mazlish et al. | |
| 10,279,106 | B1 | 5/2019 | Cook et al. | |
| 10,369,079 | B2 | 8/2019 | Rodriguez et al. | |
| 10,376,638 | B2 | 8/2019 | Levesque et al. | |
| 10,420,883 | B2 | 9/2019 | Diianni et al. | |
| 10,610,643 | B2 | 4/2020 | Mazlish et al. | |
| 10,610,644 | B2 | 4/2020 | Mazlish et al. | |
| 10,716,896 | B2 | 7/2020 | O'Connor et al. | |
| 10,842,936 | B2 | 11/2020 | Loutseiko et al. | |
| 10,874,803 | B2 | 12/2020 | Cardinali et al. | |
| 10,881,792 | B2 | 1/2021 | Mazlish et al. | |
| 10,933,188 | B2 | 3/2021 | Gonnelli et al. | |
| 10,987,468 | B2 | 4/2021 | Mazlish et al. | |
| 11,027,063 | B2 | 6/2021 | Mazlish et al. | |
| 11,083,852 | B2 | 8/2021 | Sjolund et al. | |
| 11,090,434 | B2 | 8/2021 | O'Connor et al. | |
| 11,116,899 | B2 | 9/2021 | Sjolund et al. | |
| 11,229,741 | B2 | 1/2022 | Diianni et al. | |
| 11,357,910 | B2 | 6/2022 | Kamen et al. | |
| 11,529,464 | B1 | 12/2022 | Pruijs et al. | |
| 11,559,625 | B2 | 1/2023 | Kamen et al. | |
| 11,576,594 | B2 | 2/2023 | Blomquist | |
| 11,684,714 | B2 | 6/2023 | Poetschke | |
| 11,744,944 | B2 | 9/2023 | O'Connor et al. | |
| 11,801,340 | B2 | 10/2023 | Antonio et al. | |
| 11,992,656 | B2 | 5/2024 | Golenberg et al. | |
| 12,047,417 | B2 | 7/2024 | Labudde et al. | |
| 12,088,137 | B2 | 9/2024 | Conrad et al. | |
| 12,191,017 | B2 * | 1/2025 | Mensinger .......... | A61M 5/2033 |
| 2007/0118405 | A1 * | 5/2007 | Campbell ......... | A61M 5/14248 705/2 |
| 2008/0172031 | A1 * | 7/2008 | Blomquist ............. | G16H 20/17 604/500 |
| 2009/0030398 | A1 * | 1/2009 | Yodfat .................. | G16H 20/17 702/19 |
| 2010/0017141 | A1 | 1/2010 | Campbell et al. | |
| 2011/0166544 | A1 | 7/2011 | Verhoef et al. | |
| 2011/0184267 | A1 * | 7/2011 | Duke ..................... | A61B 5/725 600/365 |
| 2011/0224523 | A1 | 9/2011 | Budiman | |
| 2013/0267813 | A1 | 10/2013 | Pryor et al. | |
| 2014/0094771 | A1 | 4/2014 | Li et al. | |
| 2014/0180203 | A1 | 6/2014 | Budiman et al. | |
| 2014/0324018 | A1 | 10/2014 | Bazargan et al. | |
| 2015/0011970 | A1 | 1/2015 | Kamen et al. | |
| 2015/0151041 | A1 | 6/2015 | Yodfat et al. | |
| 2015/0151050 | A1 * | 6/2015 | Estes ..................... | A61M 5/172 604/151 |
| 2015/0165119 | A1 | 6/2015 | Palerm et al. | |
| 2015/0314069 | A1 * | 11/2015 | Estes ................ | A61M 5/14244 604/66 |
| 2016/0129178 | A1 | 5/2016 | Askarinya et al. | |
| 2017/0213002 | A1 * | 7/2017 | Jha ...................... | A61M 5/1723 |
| 2017/0216524 | A1 | 8/2017 | Haider et al. | |
| 2017/0332952 | A1 | 11/2017 | Desborough et al. | |
| 2017/0351842 | A1 * | 12/2017 | Booth .................... | G16H 20/60 |
| 2018/0085517 | A1 * | 3/2018 | Laurence .......... | A61M 5/14216 |
| 2018/0200434 | A1 | 7/2018 | Mazlish et al. | |
| 2018/0296757 | A1 | 10/2018 | Finan et al. | |
| 2019/0009019 | A1 | 1/2019 | Shor et al. | |
| 2019/0131010 | A1 * | 5/2019 | Bengtsson ............. | G16H 50/50 |
| 2019/0156930 | A1 * | 5/2019 | Bengtsson ............. | G16H 50/20 |
| 2019/0228853 | A1 * | 7/2019 | Bengtsson .......... | A61M 5/1723 |
| 2019/0252079 | A1 | 8/2019 | Constantin et al. | |
| 2019/0272912 | A1 * | 9/2019 | Van Orden ............ | G16H 50/30 |
| 2019/0298259 | A1 | 10/2019 | Mensinger et al. | |
| 2019/0321553 | A1 | 10/2019 | Grosman et al. | |
| 2020/0170671 | A1 | 6/2020 | Schoonmaker et al. | |
| 2020/0176101 | A1 * | 6/2020 | Aanæs Wendt ........ | G16H 20/17 |
| 2020/0197608 | A1 | 6/2020 | Mazlish et al. | |
| 2021/0015996 | A1 | 1/2021 | Winheim et al. | |
| 2021/0077719 | A1 | 3/2021 | Cardinali et al. | |
| 2021/0098105 | A1 | 4/2021 | Lee et al. | |
| 2021/0137427 | A1 | 5/2021 | Cardinali et al. | |
| 2021/0177345 | A1 | 6/2021 | Wu et al. | |
| 2021/0205534 | A1 | 7/2021 | Jepson et al. | |
| 2021/0260289 | A1 | 8/2021 | Kamath et al. | |
| 2021/0290845 | A1 | 9/2021 | Mazlish et al. | |
| 2021/0308370 | A1 | 10/2021 | Arnold et al. | |
| 2021/0379282 | A1 | 12/2021 | O'Connor et al. | |
| 2022/0062553 | A1 * | 3/2022 | Constantin ............ | G16H 20/17 |
| 2022/0160309 | A1 | 5/2022 | Poltorak | |
| 2022/0168506 | A1 | 6/2022 | Zhong et al. | |
| 2022/0172816 | A1 | 6/2022 | Mensinger et al. | |
| 2022/0192591 | A1 | 6/2022 | Patek | |
| 2022/0203023 | A1 | 6/2022 | O'Connor et al. | |
| 2022/0211937 | A1 | 7/2022 | Kamen et al. | |
| 2022/0211944 | A1 | 7/2022 | Mensinger et al. | |
| 2022/0233773 | A1 | 7/2022 | Rueda et al. | |
| 2022/0241504 | A1 * | 8/2022 | Lee ........................ | A61K 38/22 |
| 2022/0249773 | A1 | 8/2022 | Zheng et al. | |
| 2022/0273873 | A1 | 9/2022 | Williams et al. | |
| 2022/0362469 | A1 | 11/2022 | Kim et al. | |
| 2022/0379029 | A1 | 12/2022 | Zade et al. | |
| 2023/0018355 | A1 | 1/2023 | Narayanaswami | |
| 2023/0211075 | A1 | 7/2023 | Fiechter et al. | |
| 2023/0270933 | A1 | 8/2023 | Sjölund et al. | |
| 2023/0330335 | A1 | 10/2023 | Sjolund et al. | |
| 2023/0330336 | A1 | 10/2023 | Sjolund et al. | |
| 2023/0343430 | A1 * | 10/2023 | Narayanaswami .... | G16H 50/30 |
| 2024/0042128 | A1 | 2/2024 | Bang et al. | |
| 2024/0075208 | A1 | 3/2024 | Lee et al. | |
| 2024/0123141 | A1 | 4/2024 | Lee et al. | |
| 2024/0268724 | A1 | 8/2024 | Causey | |
| 2024/0269376 | A1 | 8/2024 | Tschirren et al. | |
| 2025/0140364 | A1 | 5/2025 | Mensinger et al. | |
| 2025/0319249 | A1 | 10/2025 | Jeon et al. | |

FOREIGN PATENT DOCUMENTS

| | | | |
|---|---|---|---|
| KR | 20200027984 | A | 3/2020 |
| WO | 2009048462 | A1 | 4/2009 |
| WO | 2015100248 | A1 | 7/2015 |
| WO | 2016181384 | A2 | 11/2016 |
| WO | 2018218082 | A1 | 11/2018 |
| WO | 2018229783 | A1 | 12/2018 |
| WO | 2019089178 | A1 | 5/2019 |
| WO | 2019118541 | A1 | 6/2019 |
| WO | 20190118541 | | 6/2019 |
| WO | 2022097057 | A1 | 5/2022 |

(56) References Cited

OTHER PUBLICATIONS

Grunberger, G. et al., "Consensus Statement by the American Association of Clinical Endocrinologists/American College of Endocrinology Insulin Pump Management Task Force," AACE, 2014, pp. 463-469, v. 20(No. 5).
International Search Report and Written Opinion, mailed Jul. 3, 2023 in PCT/IB2023/053951.
International Search Report and Written Opinion, mailed Jul. 3, 2023 in PCT/IB2023/053952.
International Search Report and Written Opinion, mailed Jul. 5, 2023 in PCT/IB2023/053950.
European Search Report in EP Application No. 21888795.8, dated Apr. 4, 2024.
IN Foreign Office Action in related IN application 202417089119, mailed May 5, 2026.
IN Foreign Office Action in related IN application 202417089120, Mailed Aug. 3, 2026.

* cited by examiner

SYSTEMS, DEVICES AND RELATED METHODS OF COORDINATING INSULIN MANAGEMENT AND DELIVERY MODES IN FASTING AND NON-FASTING PERIODS

CROSS-REFERENCE TO RELATED APPLICATIONS

This application claims priority to U.S. Provisional Patent Application Ser. No. 63/332,001, filed on Apr. 18, 2022, and entitled "INSULIN MANAGEMENT FOR DELIVERING INSULIN DURING A FASTING PERIOD", the contents of which is hereby incorporated by reference in its entirety.

FIELD OF THE DISCLOSURE

This disclosure relates to insulin management. In particular, the disclosure relates to systems, devices and related methods of insulin management for delivering insulin during a fasting period and/or coordination of such fasting period insulin management with another therapy modality utilized during a non-fasting period.

BACKGROUND

Numerous diabetes management methods are currently used in the form of different insulin therapies. One insulin therapy is continuous subcutaneous insulin therapy provided by continuous-use insulin pumps. Known insulin pumps provide continuous subcutaneous insulin infusion (CSII) by attachment to a user's body with a reservoir of insulin inside the pump for delivery via a cannula for subcutaneous insertion. The insulin pump has a controller that may be integrated into the pump body or provided separately that controls the delivery of insulin. Automated insulin delivery (AID) is provided by using a pump with blood glucose monitoring from a device attached to the body that takes periodic blood glucose readings.

Known insulin pumps are worn continuously day and night and therefore the insulin pumps deliver a single type of rapid-acting insulin as a combination of basal and bolus insulin. The basal insulin is the background insulin that a person needs to maintain target blood glucose and does not count insulin administered or determined to counteract blood glucose elevations caused by ingested food. Where provided by CSII, such fast-acting basal or background insulin is conventionally provided at a preset and/or default basal rate and delivered to the user in a preset and/or default basal pattern, for example, 2 units per hour delivered at a continuous rate or delivered in a series of predetermined doses that are not calculated or adjusted based on real-time glucose values. On pumps, the basal rates may be varied over time but are generally stable and represent about 50% of the total insulin needs of somebody with Type 1 diabetes. In contrast to CSII basal and/or background insulin, CSII meal bolus insulin doses are pumped to cover food eaten or to correct a high blood glucose level.

Known insulin pumps require accurate estimates of numerous user-specific variables that must be used to ensure safe and effective insulin delivery over a 24-hour cycle. However, accurate estimates can be difficult to determine and require tuning over time. Continuous-use insulin pumps suffer from high costs and patient inconvenience due to a requirement to be attached to the body continuously, day and night.

Another popular diabetes management method is provided by multiple daily injections (MDI) to provide conventional insulin therapy or flexible insulin therapy. Various regimes are known and may include bolus insulin (or meal insulin) supplied by injection of rapid-acting insulin before each meal in an amount proportional to the meal and basal insulin provided as a once or twice daily injection of a long-acting insulin.

Insulin pen solutions for providing MDI, which are used by the majority of patients, typically provide lower cost and higher flexibility for patients as compared to CSII. However, the use of insulin pens, along with syringes and inhalable solutions, suffer from a requirement to be awake to use, resulting in reduced rest and/or reduced glucose control, particularly at night, when the patient would like to rest undisturbed and wake up in a healthy target glucose range.

Typically, a patient with diabetes uses a single solution for their diabetes management therapy at least in part due to the complexity of and/or risk associated with coordination of different therapies. Some risks include unrecognized insulin stacking and misinformed insulin delivery. Each available diabetes management method has a set of unique behavioral requirements, costs and potential clinical outcomes. No one solution meets the preferred behavioral, cost and clinical outcome requirements for all patients with diabetes. Patients typically follow a physician recommendation for a particular method and adapt their lifestyle to that solution.

The preceding discussion of the background to the invention is intended only to facilitate an understanding of the present invention. It should be appreciated that the discussion is not an acknowledgment or admission that any of the material referred to was part of the common general knowledge in the art at the priority date of the application.

SUMMARY

According to some embodiments, an insulin management method implemented by an insulin delivery system is provided. The method includes determining an assumed insulin on board based on an assumed external dose calculated to correct an initial blood glucose value of the user to a target blood glucose. The method includes delivering insulin from an insulin delivery device with the insulin in the form of a plurality of correction bolus doses during a fasting period in response to received blood glucose measurements, the correction bolus doses compensated for by a determined insulin on board, wherein for at least a first correction bolus dose of the plurality of correction bolus doses the determined insulin on board equals the assumed insulin on board.

In some embodiments, the insulin delivery device is an automatic insulin delivery device attachable to a user's body for a duration of the fasting period and configured to refrain from administering basal insulin at a preset or default rate or in a preset or default pattern. In some embodiments, the method includes calculating each of the plurality of correction bolus doses by comparing an evaluated blood glucose measurement to the target blood glucose to obtain a difference, adjusting the difference by a user insulin sensitivity factor to obtain a resultant dose amount, and reducing the resultant dose amount by the determined insulin on board. In some embodiments, the method includes, at the start of the delivery from the insulin delivery device, calculating the assumed external dose to correct an initial blood glucose measurement of the user to the target blood glucose. In some embodiments, the determined insulin on board is a combination of at least the assumed insulin on board and a known delivered insulin from the delivery device during the fasting period once insulin is delivered. In some embodiments, the correction bolus doses are calculated based on a user's insulin sensitivity factor obtained for the user. In some embodiments, the user's insulin sensitivity factor is derived from a total daily basal dose information used in a defined period prior to the fasting period. In some embodiments, the correction bolus doses are calculated based on at least one of a fixed target blood glucose for all users and a fixed insulin action time for all users. In some embodiments, the evaluated blood glucose measurement is evaluated at least in part by smoothing the received blood glucose measurements with a low pass filter to reduce the effect of noise and/or abrupt perturbations to obtain blood glucose values. In some embodiments, the evaluated blood glucose measurement is evaluated at least in part by retaining a received blood glucose measurement that is less than a rolling average of a predetermined number of prior received blood glucose measurements and retaining the rolling average for the received blood glucose measurement otherwise. In some embodiments, the evaluated blood glucose measurement is evaluated at least in part by projecting a downward trend of the received blood glucose measurements forward and adding the downward trend to the blood glucose measurement value used in the dose calculation. In some embodiments, the downward trend is determined based at least in part on a largest negative slope between any received blood glucose measurement within a predetermined timeframe and a reference blood glucose measurement. In some embodiments, the evaluated blood glucose measurement is evaluated at least in part by fitting received blood glucose measurements within a predetermined timeframe to a trend having a median slope selected from a plurality of regression fit slopes for different rolling subsets of received blood glucose measurements within the predetermined timeframe. In some embodiments, the evaluated blood glucose measurement is evaluated at least in part by filtering the received blood glucose measurements. The filtering including imposing a progressively increasing limit on how much each next received blood glucose measurement can increase compared to the previous received blood glucose measurement for increasing received blood glucose measurements, and amplifying how much each next received blood glucose measurement decreases compared to the previous received blood glucose measurement for decreasing received blood glucose measurements. In some embodiments, the method includes limiting the correction bolus doses to a defined maximum dose per correction bolus dose such that the correction bolus dose is a divided portion of a total correction bolus dose.

In some other embodiments, an insulin management method implemented by a controller of an insulin delivery device for delivering insulin during a fasting period from a delivery device in the form of a wearable automated insulin delivery device is provided. The method includes determining a user insulin sensitivity factor. The method includes receiving blood glucose measurements. The method includes evaluating the blood glucose measurements to obtain evaluated blood glucose values. The method includes determining an assumed insulin on board based on an assumed external dose calculated to correct an initial blood glucose value of the user to a target blood glucose. The method includes calculating periodic correction bolus doses by comparing an evaluated blood glucose value to a target blood glucose to obtain a difference, the difference adjusted by the user insulin sensitivity factor to obtain a resultant dose amount, and the resultant dose amount compensated by a determined insulin on board. Correction bolus doses in an initial period are calculated using the determined insulin on board set equal to the assumed insulin on board. Delivering at least a portion of a calculated correction dose at periodic time intervals.

In some embodiments, the assumed insulin on board is initially assumed to be sufficient to bring an initial blood glucose measurement into a target range and is reduced over time during the fasting period. In some embodiments, the method includes adjusting the assumed insulin on board over time based on comparisons between to the evaluated blood glucose measurement. In some embodiments, the determined insulin on board includes a known delivered insulin from delivered correction doses from the delivery device during the fasting period. In some embodiments, the method includes dividing the correction dose into delivery portions with a maximum delivery rate for a maximum amount of insulin to be delivered over a given time period. In some embodiments, the method includes determining an initial user insulin sensitivity factor for the fasting period based on a received total daily basal dose information. In some embodiments, the method includes adjusting the initial user insulin sensitivity factor by a sensitivity safety factor configured to bias the calculating periodic correction bolus doses to less insulin dosage. In some embodiments, the method includes adjusting the target blood glucose by a target safety factor based at least in part on a difference between a received blood glucose measurement and the target blood glucose. In some embodiments, the method includes adjusting the calculated correction bolus dose by an overall safety factor configured to limit the calculated bolus dose to a a maximum delivery rate for insulin to be delivered over a time period between delivery of correction bolus doses. In some embodiments, the target blood glucose is time varying to decrease over time during the fasting period and a rate of decrease over time of the target blood glucose is determined based on an assumption that blood glucose levels are being lowered by existing externally administered insulin administered prior to the fasting period. In some embodiments, the user insulin sensitivity factor is initially set at a predetermined value and adjusted over time based at least in part on a difference between received blood glucose measurements and expected blood glucose. In some embodiments, evaluating the blood glucose measurements includes filtering for increasing blood glucose values and not filtering for decreasing blood glucose values. In some embodiments, evaluating the blood glucose measurements includes adjusting for a long term downward trend over a period of hours in the fasting period. In some embodiments, delivering at least a portion of the correction doses includes delivering a first zero dose.

In yet other embodiments, an insulin management system of an insulin delivery device in the form of an automatic insulin delivery device attachable to a user's body for a duration of a fasting period is provided. The system includes a delivery component of the insulin delivery device configured to deliver insulin in the form of a plurality of correction bolus doses in response to received blood glucose measurements, the correction bolus doses compensated for by a determined insulin on board, wherein for at least a first correction bolus dose of the plurality of correction bolus doses the determined insulin on board equals an assumed insulin on board based on an assumed external dose calculated to correct an initial blood glucose value of the user to a target blood glucose.

In some embodiments, the delivery component includes an insulin sensitivity factor receiving component configured to determine a user insulin sensitivity factor, a blood glucose measurement receiving component configured to periodically receive blood glucose measurements, a blood glucose measurement evaluating component configured to evaluate the blood glucose measurements, a correction dose calculating component configured to calculate the periodic correction bolus, and the delivery component delivering at least a portion of a calculated correction dose at time intervals. In some embodiments, the insulin sensitivity factor receiving component is configured to derive an initial insulin sensitivity factor from a total daily basal dose information received from a non-fasting insulin management modality in a defined period prior to the fasting period for use in determining the correction bolus doses. In some embodiments, the delivery component includes an insulin on board determining component including an assumed insulin on board component for configured to calculate an initial assumed correction dose to correct an initial blood glucose measurement of the user to a target blood glucose. In some embodiments, the insulin on board determining component also includes a device insulin on board component and the correction bolus doses of the fasting period are calculated based on assumed insulin on board and known delivered insulin from the delivery device. In some embodiments, the delivery component includes an activation component for detecting activation of the delivery device to commence delivery of insulin from the fasting insulin delivery device. In some embodiments, the correction dose calculating component is configured to determine the correction bolus doses for the fasting period at each blood glucose measurement timepoint to determine if insulin is required to bring the user to a target blood glucose. In some embodiments, the measurement evaluating component is configured to perform at least one of smoothing the received blood glucose measurements with a low pass filter to reduce the effect of noise and/or abrupt perturbations to obtain blood glucose values, retaining a received blood glucose measurement that is less than a rolling average of a predetermined number of prior received blood glucose measurements and retaining the rolling average for the received blood glucose measurement if the received blood glucose is not less than the rolling average, projecting a downward trend of the received blood glucose measurements forward and adding the downward trend to the blood glucose measurement value used in the dose calculation, filtering the received blood glucose measurements, the filtering comprising imposing a progressively increasing limit on how much each next received blood glucose measurement can increase compared to the previous received blood glucose measurement for increasing received blood glucose measurements, and amplifying how much each next received blood glucose measurement decreases compared to the previous received blood glucose measurement for decreasing received blood glucose measurements, and fitting received blood glucose measurements within a predetermined timeframe to a trend having a median slope selected from a plurality of regression fit slopes for different rolling subsets of received blood glucose measurements within the predetermined timeframe. In some embodiments, the delivery component includes a correction dose limiting component configured to limit the correction bolus doses for the fasting period to a defined maximum dose given at any time point to minimize sudden corrections. In some embodiments, the correction dose limiting component is configured to limit each of the correction bolus doses for the fasting period to at least a minimum dose deliverable by the delivery device hardware. In some embodiments, the delivery component includes a safety factor component configured to provide safety factors to parameters on which the dose correction is based. In some embodiments, the delivery component includes including an end-procedure component configured to coordinate an end bolus delivery at the end of the fasting period. In some embodiments, the delivery component includes a processor and a memory configured to provide non-transitory, computer-readable program instructions to the processor to execute functions of the components. In some embodiments, the system includes a mobile user computing device. The mobile computer device includes a processor and a memory configured to provide non-transitory, computer-readable program instructions to the processor to execute functions of components, a basal insulin input component for requesting a value from a user of a total daily basal dose information used in a defined period prior to the fasting period, and a controller pairing component for pairing the mobile user computing device to a controller of the delivery device.

In yet other embodiments an automatic insulin delivery device attachable to a user's body for a duration of a fasting period is provided. The device includes a durable portion including a delivery component configured to control a delivery of insulin in the form of a plurality of correction bolus doses in response to received blood glucose measurements, at least the first correction bolus dose of the plurality of correction bolus doses determined based on a determined insulin on board equal to an assumed insulin on board that is determined based on an assumed external dose calculated to correct an initial blood glucose value of the user to a target blood glucose. The device includes a disposable portion including a reservoir configured to contain insulin and configured to automatically deliver the correction bolus doses to the user.

In some embodiments, the reservoir is configured to be fillable from a non-fasting insulin injection device used during a non-fasting period.

In yet other embodiments, a computer-implemented method for managing delivery of insulin during a fasting period from a delivery device in the form of a wearable automated insulin delivery device worn for the fasting period is provided. The method is carried out by a computing application provided at a mobile user computing device. The includes requesting a value from a user of a total daily basal dose information used in a defined period prior to the fasting period. The includes pairing the mobile user computing device to a controller of the delivery device, the controller configured to control a delivery of insulin in the form of a plurality of correction bolus doses in response to received blood glucose measurements, the correction bolus doses compensated for by a determined insulin on board, wherein for at least a first correction bolus dose of the plurality of bolus doses the determined insulin on board is equal to an assumed insulin on board based on an assumed external dose calculated to correct an initial blood glucose value of the user to a target blood glucose. The includes transmitting and receiving information to and from the controller of the delivery device during the fasting period.

In some embodiments, requesting a value from a user of a total daily basal dose information includes requesting a usual number of units of basal insulin received from a non-fasting form of insulin therapy. In some embodiments, the method includes pairing the mobile user computing device to a blood glucose monitor to transfer blood glucose measurements to the delivery device. In some embodiments, the method provides a display of a session history of information relating to the fasting period. In some embodiments, the method includes providing user training in use of a delivery device. In some embodiments, the method includes coordinating a fast-ending procedure for the user including dividing a fast-ending meal bolus into a first portion equal to a remaining insulin in the delivery device at the end of the fasting period and a second portion to be delivered to the user utilizing a delivery method other than the delivery device in a non-fasting period immediately following the fasting period.

In accordance with some embodiments, an insulin management method implemented by an insulin delivery device is provided. The method includes detecting a starting activity associated with preparation of use of the insulin delivery device in the form of an automatic insulin delivery device attachable to a user's body for a duration of a fasting period within an overall time period. The method includes initiating automated delivery of insulin in the form correction bolus doses in response to periodically received blood glucose measurements during the fasting period.

In some embodiments, the method includes detecting an ending activity associated with ending the use of the insulin delivery device, and terminating automated delivery of the insulin correction bolus doses. In some embodiments, the starting activity has a primary function other than initiating automated delivery of insulin from the insulin delivery device, thereby, being simultaneously reused as an indication to initiate automated delivery of insulin from the insulin delivery device. In some embodiments, the starting activity comprises one or more of arrival of a pre-set time of the day, removal of the insulin delivery device from a power charger, and attachment of a disposable insulin dispensing unit to the insulin delivery device. In some embodiments, the starting activity comprises one or more of attachment of the insulin delivery device to the user, detachment of an applicator of the insulin delivery device from the insulin delivery device, and a verbal command or selection by the user indicating a desire to initiate automated delivery of insulin. In some embodiments, the starting activity comprises at least one of a proximity to or pairing of a controller of the insulin delivery device to a user computing device on which a user application associated with the insulin delivery device is installed, a proximity to or pairing of the controller of the insulin delivery device to a smart insulin pen, a fill level of an insulin reservoir of a disposable insulin dispensing unit indicative of a sufficiently filled insulin reservoir for initiating the automated delivery of insulin, and a movement of a plunger of an insulin reservoir of a disposable insulin dispensing unit indicative of a filing of the insulin reservoir. In some embodiments, the method includes receiving from a paired user computing device a total daily basal dose information as received from a non-fasting insulin management modality in a defined period prior to the fasting period for use in determining the correction bolus doses. In some embodiments, initiating automated delivery of insulin includes priming the delivery device to be ready to deliver the insulin. In some embodiments, the insulin delivery device refrains from administering basal insulin at a preset or default rate or in a preset or default pattern. In some embodiments, the method includes delivering insulin in the form of the correction bolus doses in response to received blood glucose measurements, the correction bolus doses compensated by a determined insulin on board. In some embodiments, the method includes delivering at least a first correction bolus dose that is compensated for by the determined insulin on board set equal to an assumed insulin on board that is determined based on an assumed external dose calculated to correct an initial blood glucose value of the user to a target blood glucose. In some embodiments, the method includes calculating correction bolus doses by comparing an evaluated blood glucose measurement to a target blood glucose to obtain a difference, the difference adjusted by a user insulin sensitivity factor to obtain a resultant dose amount, the resultant dose amount compensated by the determined insulin on board. In some embodiments, the determined insulin on board includes the assumed insulin on board and a known delivered insulin from the delivery device. In some embodiments, the correction bolus doses are based on a user's insulin sensitivity factor derived from a total daily basal dose information used in a defined period prior to the fasting period. In some embodiments, the total daily basal dose information is an average total number of basal dose units given in an overall time period.

In yet other embodiments, an insulin management system of an insulin delivery device in the form of an automatic insulin delivery device attachable to a user's body for a duration of a fasting period within an overall time period is provided. The system includes an activation component configured to detect a starting activity associated with preparation of use of the insulin delivery device. The system includes a delivery component configured to initiate automated delivery of insulin in the form of correction bolus doses in response to periodically received blood glucose measurements during the fasting period.

In some embodiments, the system includes an end detecting component configured to detect an ending activity associated with ending the use of the insulin delivery device. In some embodiments, the starting activity has a primary function other than initiating automated delivery of insulin from the insulin delivery device, thereby, being simultaneously reused as an indication to initiate automated delivery of insulin from the insulin delivery device. In some embodiments, the activation component is configured to detect, as the starting activity, one or more of arrival of a pre-set time of the day as the starting activity, removal of the insulin delivery device from a power charger, and attachment of a disposable insulin dispensing unit to the insulin delivery device. In some embodiments, the activation component is configured to detect, as the starting activity, one or more of attachment of the insulin delivery device to the user, detachment of an applicator of the insulin delivery device from the insulin delivery device, and a verbal command or selection by the user indicating a desire to initiate automated delivery of insulin. In some embodiments, the activation component is configured to detect, as the starting activity, one or more of a proximity to or pairing of a controller of the insulin delivery device to a user computing device on which a user application associated with the insulin delivery device is installed, a proximity to or pairing of the controller of the insulin delivery device to a smart insulin pen, a fill level of an insulin reservoir of a disposable insulin dispensing unit indicative of a sufficiently filled insulin reservoir for initiating the automated delivery of insulin, and a movement of a plunger of an insulin reservoir of a disposable insulin dispensing unit indicative of a filing of the insulin reservoir. In some embodiments, the activation component detects receiving, from the paired user computing device, a total daily basal dose information as received from a non-fasting insulin management modality in a defined period prior to the fasting period for use in determining the correction bolus doses. In some embodiments, the delivery component is configured to prime the delivery device to be ready to deliver the insulin. In some embodiments, the delivery component comprises a processor and a memory configured to provide non-transitory, computer-readable program instructions to the processor to execute functions of the components. In some embodiments, the system includes a mobile user computing device that includes a processor and a memory configured to provide non-transitory, computer-readable program instructions to the processor to execute functions of components, a basal insulin input component configured to request a value from a user of a total daily basal dose information used in a defined period prior to the fasting period, and a controller pairing component configured to pair the mobile user computing device to a controller of the delivery device.

In yet other embodiments, an automatic insulin delivery device attachable to a user's body for a duration of a fasting period is provided. The device includes a durable portion including a delivery component configured to control a delivery of insulin in the form of correction bolus doses in response to received blood glucose measurements. The delivery component includes an activation component configured to detect a starting activity associated with preparation of use of the insulin delivery device, and a delivery component configured to initiate automated delivery of insulin in the form of correction bolus doses in response to periodically received blood glucose measurements during the fasting period. The device includes a disposable portion comprising a reservoir configured to contain insulin and configured to automatically deliver the correction bolus doses to the user.

In some embodiments, the reservoir is configured to be fillable from a non-fasting insulin injection device used during a non-fasting period preceding the fasting period.

In yet other embodiments, a computer-implemented method for managing delivery of insulin during a fasting period from a delivery device in the form of a wearable automated insulin delivery device worn for the fasting period is provided. The method is carried out by a computing application provided at a mobile user computing device. The method includes requesting from a user a value of a total daily basal dose information used in a defined period prior to the fasting period. The method includes pairing the mobile user computing device to a controller of the delivery device, the controller detecting a starting activity associated with preparation of use of the insulin delivery device, thereby, initiating automated delivery of insulin in the form correction bolus doses in response to periodically received blood glucose measurements during the fasting period. The method includes transmitting and receiving information to and from the controller of the delivery device during the fasting period.

In some embodiments, the value from the user of the total daily basal dose information includes a usual number of units of basal insulin received from a non-fasting form of insulin therapy. In some embodiments, the method includes pairing the mobile user computing device to a blood glucose monitor, thereby, allowing transfer of blood glucose measurements to the delivery device via the mobile user computing device. In some embodiments, the method includes providing a display of a session history of information relating to a fasting period to the user. In some embodiments, the method includes providing user training in use of a delivery device to the user. In some embodiments, the method includes coordinating a fast-ending procedure for the user including dividing a fast-ending meal bolus into a first portion equal to a remaining insulin in the delivery device at the end of the fasting period and a second portion to be delivered to the user utilizing a delivery method other than the delivery device in a non-fasting period immediately following the fasting period.

In yet other embodiments, an insulin management method of use of an insulin delivery device in the form of an automatic insulin delivery device attachable to a user's body for a duration of a fasting period within an overall time period is provided. The method includes carrying out a starting activity associated with preparation of use of the insulin delivery device, The method includes receiving automated delivery of insulin in the form correction bolus doses in response to periodically received blood glucose measurements during the fasting period.

In some embodiments, the method includes carrying out an ending activity associated with ending the user of the insulin delivery device. In some embodiments, carrying out the starting activity comprises one or more of removal of the insulin delivery device from a power charger, and attachment of a disposable insulin dispensing unit to the insulin delivery device. In some embodiments, carrying out the starting activity comprises one or more of attachment of the insulin delivery device to the user, detachment of an applicator of the insulin delivery device from the insulin delivery device, and a verbal command or selection by the user indicating a desire to initiate automated delivery of insulin. In some embodiments, carrying out the starting activity comprises at least one of pairing a controller of the insulin delivery device to a user computing device on which a user application associated with the insulin delivery device is installed, pairing the controller of the insulin delivery device to a smart insulin pen, filling an insulin reservoir of a disposable insulin dispensing unit, and causing movement of a plunger of the insulin reservoir indicative of a filing of the insulin reservoir. In some embodiments, the method includes providing at least one of an insulin sensitivity factor and total daily basal dose information used by the user in a defined period prior to the fasting period to the insulin delivery device.

According to some example embodiments, an insulin management method is provided. The method includes providing an insulin delivery device, wherein the insulin delivery device is in the form of an automatic insulin delivery device attachable to a user's body for the duration of a fasting period. The method includes delivering insulin from the insulin delivery device during the fasting period within an overall time period in the form of correction bolus doses of insulin in response to received blood glucose measurements. The insulin delivery device refrains from administering basal insulin at a preset or default rate or in a preset or default pattern. Insulin is received by the user from a non-fasting insulin management modality during a non-fasting period within the overall time period and the non-fasting insulin management modality provides at least one of a basal dose of insulin and bolus doses of insulin.

In some embodiments, a single non-fasting period and a single fasting period are provided in the overall time period and wherein the single fasting period is the major sleep portion of a user's regular daily routine. In some embodiments, the method includes calculating the correction bolus doses by comparing an evaluated blood glucose measurement to a target blood glucose to obtain a difference, the difference adjusted by a user insulin sensitivity factor to obtain a resultant dose amount and the resultant dose amount compensated by a determined insulin on board. In some embodiments, the user's insulin sensitivity factor is derived from a total daily basal dose information received from the non-fasting insulin management modality in a defined period prior to the fasting period. In some embodiments, for calculating at least the first correction bolus dose, the determined insulin on board is equal to an assumed insulin on board calculated as an assumed external dose to correct an initial blood glucose value of the user to a target blood glucose. In some embodiments, the determined insulin on board comprises the assumed insulin on board and a known delivered insulin from the delivery device. In some embodiments, the target blood glucose is fixed for all users. In some embodiments, delivering the insulin from the insulin delivery device during the fasting period is commenced based on detection of activation of the delivery device by the user. In some embodiments, the correction bolus doses for the fasting period are calculated at each blood glucose measurement timepoint to determine the timing and amount of insulin required to bring the user to the target blood glucose. In some embodiments, the evaluated blood glucose measurements are evaluated at least in part by smoothing with a low pass filter to reduce the effect of noise and/or abrupt perturbations to obtain blood glucose values. In some embodiments, the method the evaluated blood glucose measurements are evaluated at least in part by projecting a downward trend of the received blood glucose measurements forward and adding the downward trend to the blood glucose measurement value used in the dose calculation. In some embodiments, the evaluated blood glucose measurement is evaluated at least in part by retaining a received blood glucose measurement that is less than a rolling average of a predetermined number of prior received blood glucose measurements and retaining the rolling average for the received blood glucose measurement otherwise. In some embodiments, the downward trend is determined based at least in part on a largest negative slope between any received blood glucose measurement within a predetermined timeframe and a reference blood glucose measurement. In some embodiments, the evaluated blood glucose measurement is evaluated at least in part by fitting received blood glucose measurements within a predetermined timeframe to a trend having a median slope selected from a plurality of regression fit slopes for different rolling subsets of received blood glucose measurements within the predetermined timeframe. In some embodiments, the evaluated blood glucose measurement is evaluated at least in part by filtering the received blood glucose measurements. The filtering includes imposing a progressively increasing limit on how much each next received blood glucose measurement can increase compared to the previous received blood glucose measurement for increasing received blood glucose measurements, and amplifying how much each next received blood glucose measurement decreases compared to the previous received blood glucose measurement for decreasing received blood glucose measurements. In some embodiments, the method includes limiting the correction bolus doses to a defined maximum dose per correction bolus dose such that the correction bolus dose is a divided portion of a total correction bolus dose. In some embodiments, the method includes providing coordination between the non-fasting insulin management therapy and the delivery device to the user. In some embodiments, the coordination comprises providing one or more recommendations to a user relating to the non-fasting insulin management therapy and/or the delivery device. In some embodiments, the coordination comprises providing one or more predictions to a user relating to hypothetical use of the non-fasting insulin management therapy and/or the delivery device. In some embodiments, the one or more recommendations comprise at least one of a recommendation for the user to utilize the delivery device for a recommended timeframe at night, and a recommendation for the user to adjust daily basal doses of insulin from a current value to a different value. In some embodiments, wherein the one or more predictions comprise one or more of a prediction of waking blood glucose levels for the user if the user utilizes the delivery device for the recommended timeframe at night, a prediction of waking blood glucose levels for the user if the user adjusts daily basal doses of insulin from a current value to the different value, and a prediction of waking blood glucose levels for the user if the user does not utilize the delivery device for an entire night. In some embodiments, the coordination includes coordinating a fast-ending procedure for the user. Coordinating the fast-ending procedure includes receiving information relating to a fast-breaking meal that requires a meal bolus, dividing a fast-ending meal bolus into a first portion equal to a remaining insulin in the delivery device at the end of the fasting period and a second portion to be delivered to the user utilizing the non-fasting insulin management modality in a non-fasting period immediately following the fasting period, and providing the user with instructions to deliver the second portion of the fast-ending meal bolus dose from the non-fasting insulin management modality.

In some other embodiments, an insulin management system of an insulin delivery device in the form of an automatic insulin delivery device attachable to a user's body for a duration of a fasting period within an overall time period is provided. The system includes a delivery component configured to deliver insulin from the insulin delivery device during the fasting period in the form of correction bolus doses of insulin in response to received blood glucose measurements. The delivery component refrains from administering basal insulin at a preset or default rate or in a preset or default pattern. Insulin is received from a non-fasting insulin management modality during a non-fasting period within the overall time period and the non-fasting insulin management modality provides at least one of a basal dose of insulin and bolus doses of insulin.

In some embodiments, the delivery component is configured to calculate the correction bolus doses by comparing an evaluated blood glucose measurement to a target blood glucose to obtain a difference, the difference adjusted by a user insulin sensitivity factor to obtain a resultant dose amount, and the resultant dose amount compensated by a determined insulin on board. In some embodiments, the user's insulin sensitivity factor is derived from a total daily basal dose information received from the non-fasting insulin management modality in a defined period prior to the fasting period. In some embodiments, the delivery component includes an initializing component configured to, at the start of the delivery from the fasting insulin delivery device, determine an assumed insulin on board as an assumed external dose calculated to correct an initial blood glucose value of the user to a target blood glucose. In some embodiments, the delivery component includes a processor and a memory configured to provide non-transitory, computer-readable program instructions to the processor to execute functions of the components. In some embodiments, the system includes a mobile user computing device that includes a processor and a memory configured to provide non-transitory, computer-readable program instructions to the processor to execute functions of components, a basal insulin input component for requesting a value from a user of a total daily basal dose information used in a defined period prior to the fasting period, and a controller pairing component for pairing the mobile user computing device to a controller of the delivery device.

In yet other embodiments, an automatic insulin delivery device attachable to a user's body for a duration of a fasting period is provided. The device includes a durable portion including a delivery component configured to control a delivery of insulin in the form of a plurality of correction bolus doses of insulin in response to received blood glucose measurements and refraining from administering basal insulin at a preset or default rate or in a preset or default pattern. The device includes a disposable portion including a reservoir configured to contain insulin and configured to automatically deliver the correction bolus doses to the user under control of the delivery component.

In some embodiments, the reservoir is configured to be fillable from a non-fasting insulin injection device used during a non-fasting period. In some embodiments, the delivery component is configured to calculate the correction bolus doses by comparing an evaluated blood glucose measurement to a target blood glucose to obtain a difference, the difference adjusted by a user insulin sensitivity factor to obtain a resultant dose amount, and the resultant dose amount compensated by a determined insulin on board.

In yet other embodiments, a computer-implemented method for managing delivery of insulin when using a delivery device in the form of a wearable automated insulin delivery device worn for the fasting period is provided. The method is carried out by a computing application provided at a mobile user computing device. The method includes receiving information relating to a non-fasting insulin management therapy used during a non-fasting period in an overall period, receiving information relating to the delivery device used during a fasting period in the overall period, and providing coordination between the non-fasting insulin management therapy and the delivery device.

In some embodiments, the method includes providing one or more recommendations to a user relating to the non-fasting insulin management therapy and/or the delivery device. In some embodiments, the method includes providing one or more predictions to a user relating to hypothetical use of the non-fasting insulin management therapy and/or the delivery device. In some embodiments, the one or more recommendations include at least one of a recommendation for the user to utilize the delivery device for a recommended timeframe at night, and a recommendation for the user to adjust daily basal doses of insulin from a current value to a different value. In some embodiments, the one or more predictions include one or more of a prediction of waking blood glucose levels for the user if the user utilizes the delivery device for the recommended timeframe at night, a prediction of waking blood glucose levels for the user if the user adjusts daily basal doses of insulin from a current value to the different value, and a prediction of waking blood glucose levels for the user if the user does not utilize the delivery device for an entire night. In some embodiments, the method includes coordinating a fast-ending procedure for the user. The coordinating includes receiving information relating to a fast-breaking meal that requires a meal bolus, dividing a fast-ending meal bolus into a first portion equal to a remaining insulin in the delivery device at the end of the fasting period and a second portion to be delivered to the user utilizing the non-fasting insulin management modality in a non-fasting period immediately following the fasting period, and providing the user with instructions to deliver the second portion of the fast-ending meal bolus dose from the non-fasting insulin management modality.

In yet other embodiments, an insulin management method of use is provided. The method includes receiving insulin from a non-fasting insulin management modality during a non-fasting period within an overall time period, wherein the non-fasting insulin management modality provides required doses of insulin during the non-fasting period. The method includes receiving insulin from a fasting insulin delivery device during a fasting period within the overall time period, wherein the fasting insulin delivery device is an automatic insulin delivery device attachable to a user's body for the duration of the fasting period and is configured to deliver correction bolus doses of insulin in response to received blood glucose measurements and refrains from administering basal insulin at a preset or default rate or in a preset or default pattern. The method includes receiving, from a coordinating computing device, at least one of a recommendation to a user relating to the non-fasting insulin management therapy and/or the delivery device, and a prediction to a user relating to hypothetical use of the non-fasting insulin management therapy and/or the delivery device.

In some embodiments, the one or more recommendations comprise at least one of a recommendation for the user to utilize the delivery device for a recommended timeframe at night, and a recommendation for the user to adjust daily basal doses of insulin from a current value to a different value. In some embodiments, the one or more predictions comprise one or more of a prediction of waking blood glucose levels for the user if the user utilizes the delivery device for the recommended timeframe at night, a prediction of waking blood glucose levels for the user if the user adjusts daily basal doses of insulin from a current value to the different value, and a prediction of waking blood glucose levels for the user if the user does not utilize the delivery device for an entire night. In some embodiments, the method includes carrying out a coordinated fast-ending procedure by the user. The coordinated fast-ending procedure includes providing information relating to a fast-breaking meal that requires a meal bolus, receiving a first portion of a fast-ending meal bolus that is equal to a remaining insulin in the delivery device from the delivery device at the end of the fasting period, receiving instructions to deliver a second portion of the fast-ending meal bolus dose using the non-fasting insulin management modality, and delivering the second portion of the fast-ending meal bolus dose to the user utilizing the non-fasting insulin management modality in the non-fasting period immediately following the fasting period.

BRIEF DESCRIPTION OF THE DRAWINGS

A more complete appreciation of the subject matter of the present disclosure and of the various advantages thereof can be realized by reference to the following detailed description in which reference is made to the accompanying drawings in which.

DETAILED DESCRIPTION

Figure 1:
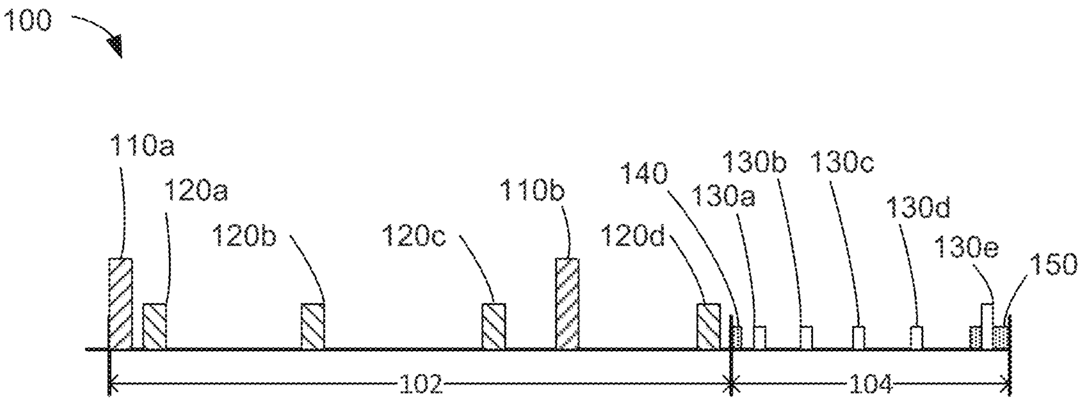
FIG. 1 illustrates an overall time period in which two different modes of insulin management may be used in a non-overlapping manner, in accordance with some example embodiments.

This disclosure describes medicant management methods, systems, and delivery devices for delivering a medicant (e.g., insulin and/or glucagon) from a wearable automated medicant delivery device during a fasting period of, for example, less than about 12 hours, where the wearable automated medicant delivery device is configured and intended to be utilized only during the fasting period. Where the automated medicant delivery device is configured to dispense insulin, the device may be considered an automated insulin delivery device, or AID device. Several embodiments are described below in connection with insulin delivery. However, the present disclosure is not so limited and also contemplates similar or identical embodiments configured for delivering any other medicament affecting blood glucose levels, e.g., glucagon for increasing blood glucose concentrations when they fall below predetermined levels, for example, during sleep, or athletic or otherwise energetically demanding physical activity.

Diabetics, by definition, are unable to regulate blood sugar properly due to substantially complete lack of endogenous insulin secretion (in Type 1 diabetics) or due to insufficient endogenous insulin secretion (in Type 2 diabetics). Accordingly, diabetics require insulin management procedures for maintaining blood glucose levels within desired target ranges essentially at all times. Accordingly, managing automatic insulin delivery only during daily fasting periods, for example when sleeping, presents several unique challenges.

First, a user must integrate a supplementary method of insulin administration outside the fasting period (e.g., multiple daily insulin injections to cover basal and meal bolus requirements) but tracking of insulin administration between multiple modes of insulin delivery can be cumbersome for users.

Second, since there is a transition between the supplementary non-fasting mode of insulin delivery and the automatic fasting mode of insulin delivery twice each day, it is may be desirable to engage and disengage the automatic fasting mode at the proper times (e.g., engage at the start of the fasting period and disengage at the end of the fasting period) but natural variations in timing and duration of these fasting or sleeping periods from day to day makes determining proper times for engagement and disengagement difficult.

And third, since automatic insulin administration only during the fasting period generally occurs while the user is sleeping and fasting, it is very important to guard against over-dispensing insulin and resultant hypoglycemic events during the fasting period, but this requires accurate accounting of insulin that is already in the user's system at the start of the fasting period and users are not always good at accurately estimating or accounting for actual insulin on board, especially as the time since the last manual insulin injection increases and that on-board insulin is progressively metabolized by the body.

Moreover, the majority of patients with diabetes (type 1 and type 2) continue to rely on multiple daily injections (MDI) therapy for diabetes management. Unfortunately, while there are many good reasons that patients may choose MDI therapy, nighttime control (as compared with automated insulin delivery (AID)) remains a missing element. Up until now, nighttime only use of AID has been impractical or even unachievable because set up of traditional insulin pump therapy (especially with AID) is a highly complex process that requires significant start up time. Additionally, continuous subcutaneous insulin infusion (CSII) is designed for infusion of basal and/or background insulin at predetermined rates rather than for use with exogenous basal insulin. For example, traditional AID includes delivery of basal and/or background insulin at predetermined, preset, and/or default rates that are not calculated or adjusted in real-time (or substantially in real-time) based on real-time (or substantially real-time) glucose values. Such basal, baseline and/or background insulin infusion would conflict with daily basal pen doses, and is not practical for twice a day transitions. Furthermore, transitioning from AID to pen and back would often leave some active insulin in your body during the changeover, which current systems aren't equipped to handle.

Aspects of this disclosure solve each of these potential problems, among any number of potential others, as described below, including through methods, devices and systems for integrating a supplementary method of insulin administration outside the fasting period; methods, devices and systems for controlling insulin administration during a fasting period using events indicative of a start and/or end of the fasting period; and/or methods, devices and systems for automated calculation and delivery of correction doses of insulin during the fasting period to, thereby, provide a simplified, safe and effective management of time in range (TIR) during extended fasting periods. While embodiments described herein may be directed toward one or more of the above-described challenges, the present disclosure contemplates utilizing and/or incorporating any feature or features from any embodiment or embodiments with any feature or features from any other embodiment or embodiments described herein.

Methods described herein solve, among other problems, the problem of transition complexity for transient use by providing a simplified system that allows for ease of transition between two different diabetes management modalities. In one implementation, the systems and methods described herein enable seamless, intermittent, episodic use of MDI for basal insulin during day cycles and AID during night cycles, thereby allowing users to benefit from low costs, high flexibility, and improved clinical outcomes. For example, diabetes management therapy with daily basal and daytime bolusing are accomplished by MDI therapy, while overnight glucose control is achieved by a short-term wear insulin pump that provides AID control during fasting to allow the user to sleep well and wake in a target glucose range without awakening for correction bolusing.

FIG. 1 illustrates an example of an overall time period 100 in which a plurality of different modes of insulin management may be used in a non-overlapping manner, in accordance with some example embodiments. In some situations, overall timer period 100 may be 24 hours in length, as is a usual daily routine for most users. However, the overall time period 100 may be adjusted for users who require different and sometimes more erratic schedules, for example, due to shift work. The described insulin management is based on a user receiving insulin from one or more non-fasting insulin management modalities (e.g., an insulin pen 210 as shown in or described in connection with FIG. 2) during a non-fasting period 102 of the overall time period 100 and receiving insulin from a different fasting insulin management modality (e.g., fasting-time wear delivery device 230 as shown in or described in connection with FIG. 2) during a fasting period 104 of the overall time period 100.

As described herein, the non-fasting insulin management modality and the fasting period insulin management modality are intended for adjunctive, e.g., supplemental, use without the non-fasting and fasting modalities actively overlapping. For example, as will be described below, neither basal insulin dose(s), e.g., 110*a*, 110*b*, nor meal bolus doses 120*a*-120*d* will typically be given from the non-fasting insulin management modality during the fasting period 104 and correction doses 130*a*-130*e* will typically not be given from the fasting insulin management modality during the non-fasting period 102. Accordingly, once non-fasting period 102 has commenced the fasting period insulin management modality is not intended for use, and once fasting period 104 has commenced, the non-fasting insulin management modality is not intended for use. However, at least part of the basal doses 110*a*, 110*b* or meal bolus doses 120*a*-120*d* administered during the non-fasting period 102 may still be active in the body, as insulin on board, during the fasting period 104. Correction doses 130*a*-130*e* during a fasting period 104 are supplemental to meal boluses 120*a*-120*d* given during non-fasting period 102, for example, when meal boluses 120*a*-120*d* have not sufficiently covered the rise in glucose resulting from a meal or when glucose otherwise remains elevated after meals or meal bolusing. This non-sufficiency may be due to errors in bolus calculation, errors in reported meal information, errors in therapy parameters used for therapy calculations, hormonal factors, and the like.

The non-fasting period 102 may be the time that a user is awake in a daily cycle; however, the non-fasting period 102 may include short periods of sleep, such as a day-time nap. The fasting period 104 may be a time period of intended fasting. This may be at nighttime or any time period wherein only correction bolusing is needed in additive sense to any existing basal therapy and meal bolus therapy, which may still be "on board" throughout the fasting time period 104. Accordingly, the fasting period 104 may be the time that a user is asleep in a daily cycle. For most users, the fasting period 104 may be a night-time period of between 6 and 12 hours, and typically less than 22 hours, when the user is typically lying down in a restful position and does not eat during this time.

In FIG. 1, basal doses 110*a* and/or 110*b* and meal bolus doses 120*a*-120*d* are administered via the non-fasting insulin management modalities during the non-fasting period 102. Basal insulin is the background insulin that a diabetic person needs to maintain blood glucose in a desired range in the absence of meals during the non-fasting period 102. While needs vary by user, basal insulin typically comprises approximately 50% of the total insulin needs of somebody with Type 1 diabetes. Basal dose(s) 110*a*, 110*b* may comprise slow-acting insulin. Where one basal dose 110*a* is administered per day, dose 110*a* may be configured to fulfill the user's 24-hr basal requirements for insulin and may be administered by daily injection of insulin administration during the non-fasting period 102, for example via insulin pen 210 (see, e.g., FIG. 2). Where two basal doses 110*a*, 110*b* are administered per day, doses 110*a*, 110*b* may each be configured to fulfill the user's 12-hr basal requirements for insulin and doses 110*a*, 110*b* may be administered by a multiple daily injection (MDI) mode during the non-fasting period 102.

By contrast, a meal bolus dose is an amount of insulin needed to compensate for an expected rise in glucose in a person with diabetes resulting from eating food, where the compensation aims to bring blood glucose into a target range. Typically, a user eating some amount of carbohydrates requires insulin to avoid resulting elevated glucose. FIG. 1 illustrates meal bolus doses 120*a*, 120*b*, 120*c*, 120*d* (120*a*-120*d*) administered by the MDI mode during the non-fasting period 102. In contrast to basal dose(s) 110*a*, 110*b*, meal bolus doses 120*a*-120*d* may comprise fast-acting insulin. While a certain number of meal bolus doses are illustrated in non-fasting period 102, they are for example only and any number of doses are contemplated as required by the number of meals eaten during the non-fasting period 102.

Figure 2:
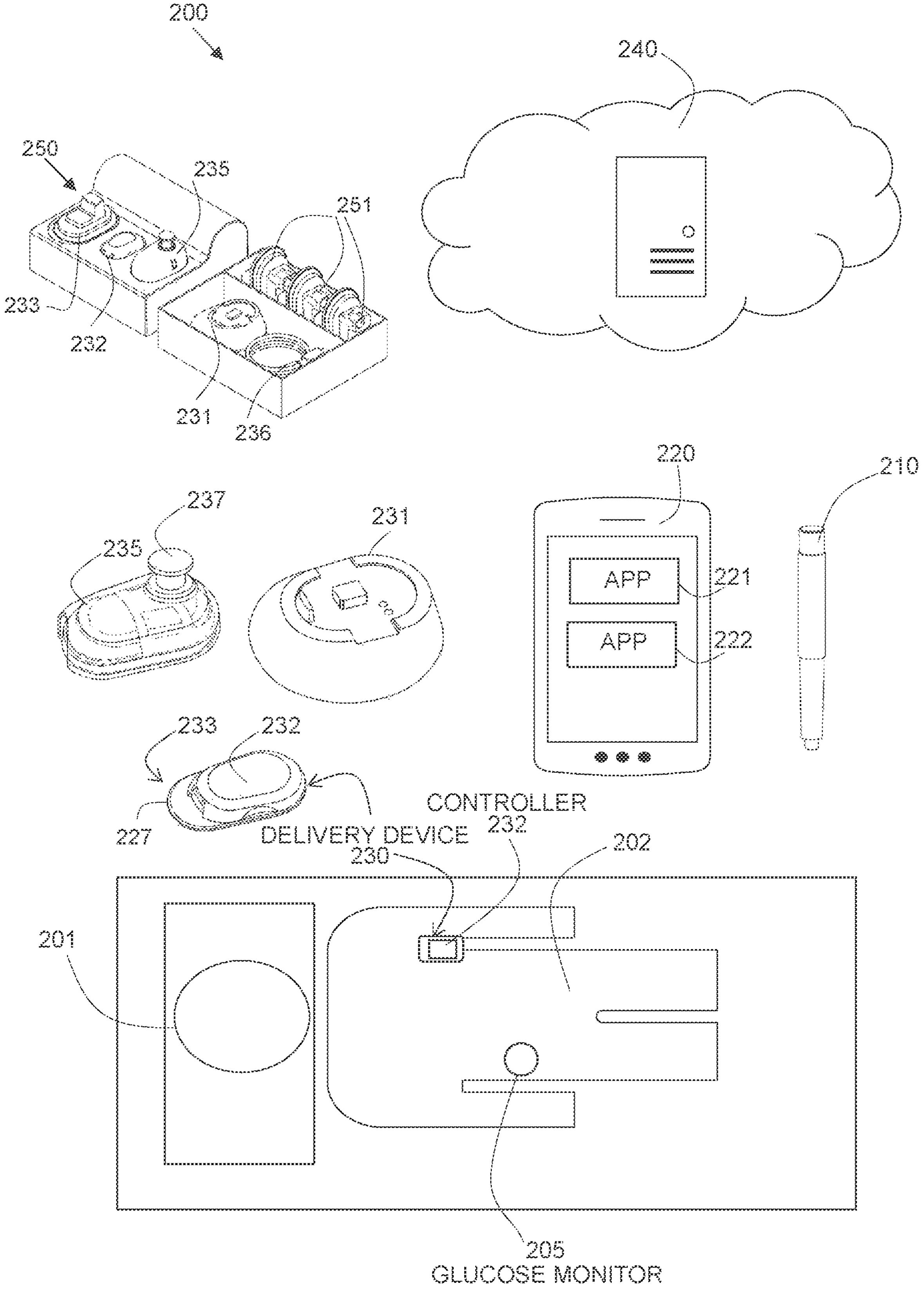
FIG. 2 is a schematic diagram illustrating an example embodiment of an overall therapy arrangement, according to some example embodiments.

During the fasting period 104 within the overall time period 100, the described insulin management method delivers insulin from a fasting automatic insulin delivery (AID) device attachable to a user's body for the duration of the fasting period 104, for example, a night-time wear only pump as provided in PCT Patent Application No. PCT/IB2021/060206, the contents of which are incorporated herein by reference. Such a device 230 is illustrated in FIG. 2, as will be described in more detail below. Since no meals are eaten during the fasting period 102, the device 230 is configured to deliver fast-acting insulin, in the form of correction bolus doses or micro-bolus doses 130*a*-130*e*, to gradually correct high blood glucose measurements during the fasting period 104 and, thereby, allow the user to sleep well and wake in a target glucose range without awakening for correction bolusing. While a certain number of correction bolus doses are illustrated in fasting period 104, they are for example only and any number of correction doses are contemplated as required during the fasting period 104.

Basal doses 110*a*, 110*b* are assumed to be taken during non-fasting period 102 from the non-fasting insulin management modality. Notably, fasting insulin delivery device 230 refrains from administering background and/or basal insulin to the user. Specifically, fasting insulin delivery device 230 does not allow for any preset default, basal or background doses of fast-acting insulin delivery, for example, to account for a user's basal insulin needs. In other words, in contrast to the operation of conventional CSII devices, delivery device 230 does not allow a preset basal rate of basal insulin delivery or a preset pattern of basal insulin delivery, for either fast- or slow-acting insulin. Delivery device 230 also does not store such preset basal rates or preset patterns of basal insulin delivery, fast- or slow-acting. Delivery device 230 does not deliver background insulin whatsoever. Therefore, background, baseline and/or basal rates of basal, baseline and/or background insulin delivery are unalterably fixed at zero, as insulin delivery device 230 may be specifically configured to be incapable of such basal, baseline and/or background insulin delivery. Accordingly, fasting insulin delivery device 230 is designed to perform only minor correction bolusing while the user is fasting for a limited time period and, in contrast to CSII devices, cannot deliver any insulin dose without first running an insulin correction dose calculation that is based on true and/or evaluated real-time (or substantially real-time) blood glucose values, as described anywhere in this disclosure. And in some embodiments, fasting insulin delivery device 230 is also not configured for meal bolus delivery whatsoever. This configuration greatly simplifies the requirements for delivery algorithms to enable fasting insulin delivery device 230 to effectively maintain blood glucose in a target range without the need for information relating to basal rates, carbohydrate ratios, or insulin action time.

As will be described in more detail below, a delivery algorithm tasked with determining the size of correction doses 130*a*-130*e* employs various safety factors to adjust one or more variables and ensure that there is no over-administration of insulin or attendant over-correction of blood glucose during non-fasting period 104. Moreover, since the user must integrate the non-fasting mode of insulin administration outside the fasting period, one or more systems, devices and methods disclosed herein may also provide functionality that integrates this supplementary method of insulin administration, utilized outside fasting period 104, with the automatic fasting insulin delivery method of insulin administration utilized during fasting period 104. In some embodiments, to aid efficient transition between this supplementary method of insulin administration during non-fasting period 102 and the automatic corrective method of delivery during fasting period 104, one or more systems, devices and methods disclosed herein may also be configured to accurately detect one or both of a starting activity 140 (FIG. 1) indicative of a need, desire, or appropriateness for initiating automated delivery of insulin from insulin delivery device 230 at or temporally near the beginning of fasting period 104, and an ending activity 150 (FIG. 1) indicative of a need, desire, or appropriateness for terminating automated delivery of insulin from insulin delivery device 230 at or temporally near the end of fasting period 104, as will be described in more detail below.

In the following description, various embodiments of methods, systems, and devices are described with reference to the FIGS. Described individual features of each of the embodiments may be used in other embodiments. Where the methods are described in flow diagrams, with features described by steps in the flow diagram the following may apply. One or more of the described individual features of a method may be accomplished by a single step. Individual features described as a single method step may be carried out by more than one step. Portions of the described individual features may overlap. The order of features of the methods may also be changed. In computer-implemented methods, it will be understood that each block of a flowchart illustrations and/or block diagrams, and combinations of blocks in the flowchart illustrations and/or block diagrams, may be implemented by non-transitory, computer readable program instructions.

FIG. 2 is a schematic diagram which illustrates an example embodiment of an overall therapy arrangement 200 in which described insulin management methods of a fasting-time wear delivery device 230 is used.

A user 201 is shown in a sleeping position with a continuous glucose monitor (CGM) 205 attached to their body 202. CGM 205 may take and transmit blood glucose measurements to a base station or mobile computing device 220. The user 201 may use an insulin pen 210, such as a smart-pen, or other MDI method during the daytime, i.e., during non-fasting period 102 of FIG. 1. The user 201 may use a mobile computing device 220, such as a smart phone, for managing their insulin usage. In one embodiment, a known application 221 provided by the mobile computing device 220 may receive blood glucose measurements from CGM 205 and may manage daytime MDI therapy, for example, by interaction with insulin pen 210.

Fasting-time wear delivery device 230 is utilized only during fasting period 104 as shown in FIG. 1. Fasting-time wear delivery device 230 is configured to deliver rapid-acting insulin in small correction doses 130*a*-130e based at least in part on periodic blood glucose measurement from CGM 205. In some embodiments, CGM 205 may be incorporated into delivery device 230. In other embodiments, CGM 205 may be a separate CGM worn by the user day and night.

In some embodiments, fasting-time wear delivery device 230 may be provided in a kit 250. Delivery device 230 comprises a durable unit into which a disposable dispensing unit 233 containing the insulin is fitted. Delivery device 230 may have an applicator 235 for use while filling delivery device 230 with insulin and/or for applying delivery device 230 to the user's body 202 as described anywhere in this disclosure. A charger (e.g., charging station) 231 may be configured to charge the durable unit, for example during non-fasting period 102 of FIG. 1, so as to be ready for re-use during a subsequent fasting period 104.

The durable unit of delivery device 230 includes a controller 232 for controlling the delivery of insulin from delivery device 230 according to a delivery algorithm as described anywhere in this disclosure. The delivery algorithm may be provided entirely on the controller 232. This may be provided in the form of software and/or hardware components. In a first alternative, the delivery algorithm may be provided remotely instructing the delivery amounts to the controller 232. This may be provided remotely from: a cloud computing system 240; a computer application 222 on a user's mobile computing device 222; or another form of computing device or system. In a second alternative, the delivery algorithm may be distributed between any two or more of: the controller 232; a cloud computing system 240; a computer application 222 on a user's mobile computing device 222; and another form of computing device or system.

Kit 250 may comprise multiple sealed packages 251, for example, blister-packs, each containing a disposable dispensing unit 233. As will be described in more detail in connection with FIGS. 13A-13L, dispensing units 233 each include a reservoir 225 and a plunger 226 supported on a base 227. Plunger 226 is provided for controlled delivery of insulin from reservoir 225 to the user via a cannula (not shown). As will also be described in more detail in connection with FIGS. 13A-13L, dispensing units 233 may be provided with a coupler 228 and dispensing units 233 may be provided without any insulin in their reservoirs 225 for filling from an MDI therapy pen 210 or syringe by using the coupler 228 to position pen 210 or a syringe as described anywhere in this disclosure. Alternative embodiments may be configured to received pre-filled cartridges in place of reservoir 225. Controller 232 is attached to dispensing unit 233 to form delivery device 230.

The kit 250 may also include an applicator 235 and a charger 231 with a charging cable 236. Push applicator 235 is configured to attach to an upper portion of delivery device 230 to allow the delivery device to be removed from base 227 or positioned on the user's body with a single hand. When delivery device 230, held within applicator 235, is positioned on the user's body and the applicator's push button 237 is pushed down by the user, delivery device 230 is pushed against the user's body with sufficient force that an adhesive layer disposed on an underside of base 227 is adhered to the user's body and a cannular on the underside of the delivery device pierces the user's skin ready for delivery of insulin. Applicator 235 may then be removed from delivery device 230, after which, delivery device 230 may be ready to deliver correction doses 130*a*-130*e* during fasting period 104. At the end of fasting period 104, delivery device 230 may be removed from the user's body and returned to charger 231.

Figure 3:
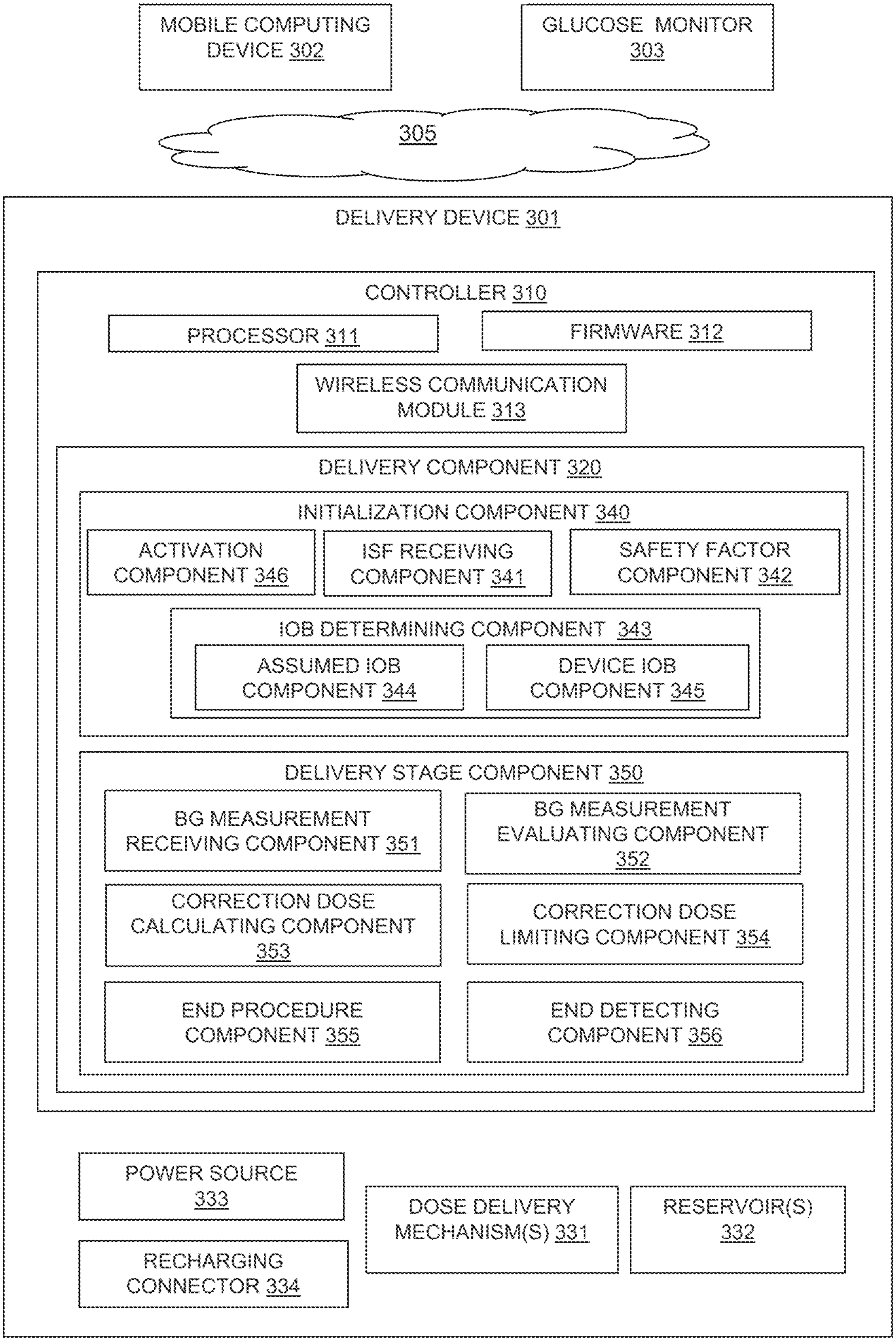
FIG. 3 is a block diagram of a system of controlling delivery of insulin, according to some example embodiments.

An example embodiment of a delivery device 301 comprising controller 232 and delivery device 230 is illustrated by the schematic block diagram of FIG. 3. Referring to FIG. 3, device 301 may include a power source 333 and a recharging connector 334. Device 301 may include a wireless communication module 313 for communication via a wireless network 305 with a continuous glucose monitor (GCM) 303 for receiving glucose measurement of a user. Device 301 may also be configured to communicate via a wireless network 305 with a mobile computing device 302 such as a mobile phone, laptop or desktop computer. In some embodiments, mobile computing device 302 may correspond to mobile computing device 220 of FIG. 2. In some embodiments, glucose monitor 303 may correspond to CGM 205 of FIG. 2.

Controller 310 may include a microcontroller in the form of a processor 311 with firmware 312 that controls the operation of delivery device 301. Firmware 312 may be provided by the components of controller 310. Processor 311 may be a hardware module or a circuit for executing the functions of the described components which may be software units executing on the at least one processor 311. Memory may be configured to provide computer instructions to processor 311 to carry out the functionality of the components.

Controller 310 may include a delivery component 320 that may be in communication with the mobile computing device 302 and/or glucose monitor 303 and determines when and how much to dispense in a dose by means of a dose delivery mechanism 331 of delivery device 301 from a reservoir 332 of the delivery device 301. In some embodiments, reservoir 332 may correspond to reservoir 225 as previously described in connection with delivery device 230. Delivery component 320 may include an initialization component 340 for an initial configuration stage of the delivery component 320 and a delivery stage component 350 for a delivery stage.

In some embodiments, controller 310 may also be configured to cause dose delivery mechanism 331 (or a similar separate mechanism of device 301 for glucagon) to deliver a predetermined and/or calculated amount of glucagon from a respective reservoir (similar to 332) for glucagon based at least in part on blood glucose levels falling below a predetermined low level (e.g., 40 mg/dl) and/or to maintain blood glucose levels above a predetermined safe level during episodes of intense user activity (e.g., exercise).

Initialization component 340 may include an activation component 346 for detecting activation of the delivery device to commence delivery of insulin as described anywhere in this disclosure. Initialization component 340 may include an insulin sensitivity factor (ISF) receiving component 341 for receiving an insulin sensitivity factor from the user or from a doctor and/or for deriving an insulin sensitivity factor from one or more other parameters as described anywhere in this disclosure, such as but not limited to a received total daily basal dose (TDBD) of insulin. Initialization component 340 may include a safety factor component 342 for providing one or more safety factors to parameters on which dose correction is based as described anywhere in this disclosure. Initialization component 340 may include an insulin on board determining component 343 including an assumed insulin on board component 344 for calculating an initial assumed correction bolus dose to correct an initial blood glucose measurement of the user to a target blood glucose, and a device insulin on board component 345 for determining known delivered insulin from delivery device 230 as described anywhere in this disclosure.

Delivery stage component 350 may include a blood glucose (BG) measurement receiving component 351 for periodically receiving blood glucose measurements on which correction bolus doses 130*a*-130*e* for fasting period 102 are based. Delivery stage component 350 may include a measurement evaluating component 352 for smoothing, manipulating, modifying and/or supplementing the received blood glucose measurements to reduce the effect of noise or abrupt perturbations on obtained blood glucose values as described anywhere in this disclosure. In some embodiments, such smoothing, manipulating, modifying and/or supplementing the received blood glucose measurements may also be considered as implementing a safety factor on the received blood glucose measurements and/or as biasing the received blood glucose measurements toward an avoidance of overdosing insulin and/or the attendant hypoglycemic episodes that can otherwise occur during fasting period 104.

Delivery stage component 350 may include a correction dose calculating component 353 for determining the correction bolus doses for a fasting period at one or more blood glucose measurement timepoints to determine when insulin is required to bring the user to a target blood glucose. Correction dose calculating component 353 may be configured to compare a received blood glucose value from measurement receiving component 351 (or a smoothed, manipulated, modified and/or supplemented value from evaluating component 352) to a target blood glucose to obtain a difference that is adjusted by a user insulin sensitivity factor (ISF) and that result compensated (reduced) by a determined insulin on board as described anywhere in this disclosure. Delivery stage component 350 may include a correction dose limiting component 354 for limiting the correction bolus doses for a fasting period to a defined maximum dose given at any time point to minimize sudden corrections as described anywhere in this disclosure. Correction dose limiting component 354 may also be configured to limit the correction bolus doses given at any time point for a fasting period to a minimum dose that is based on the delivery device hardware.

Figure 7:
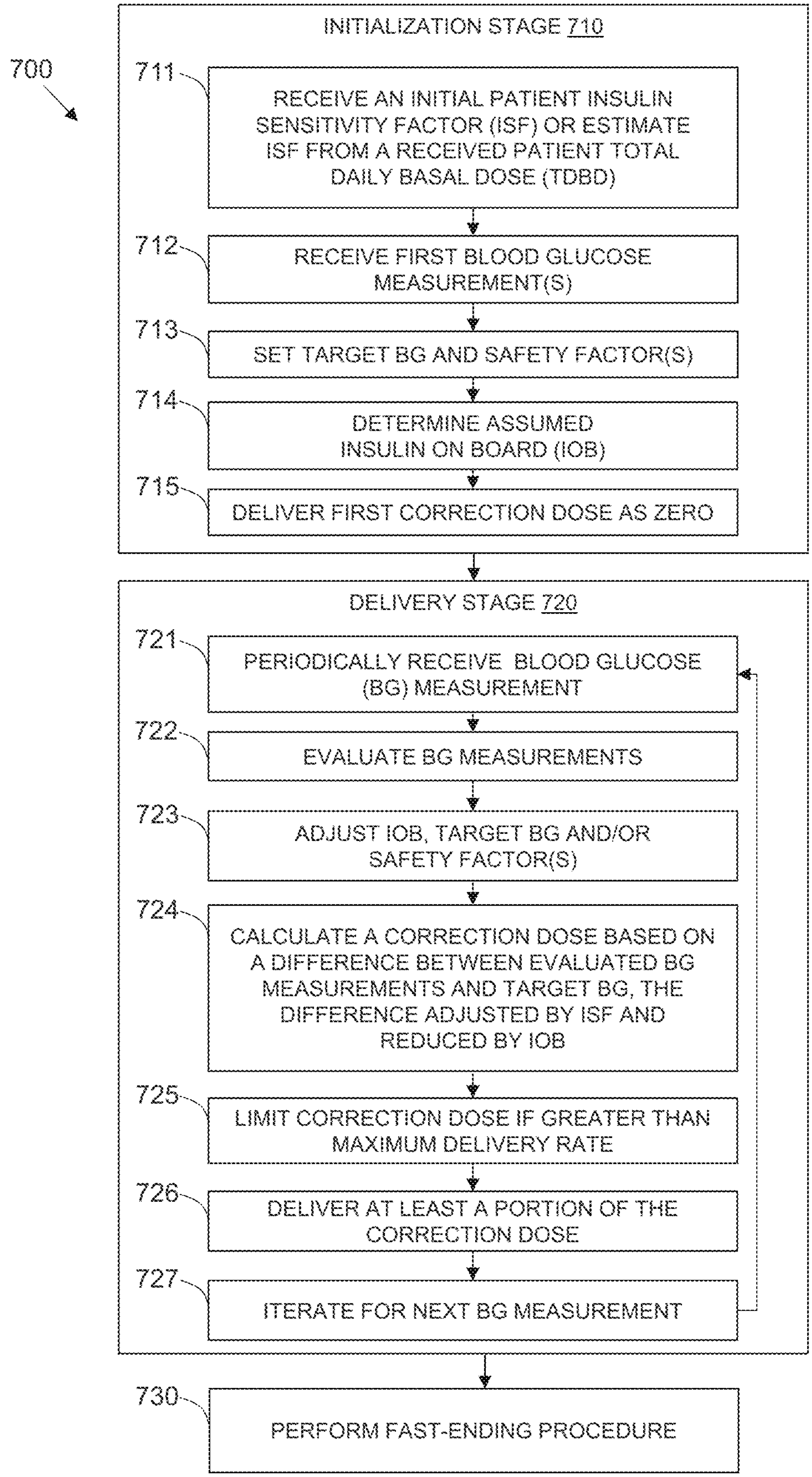
FIG. 7 is a flow diagram of methods of controlling delivery of insulin, according to some example embodiments.
Figure 11:
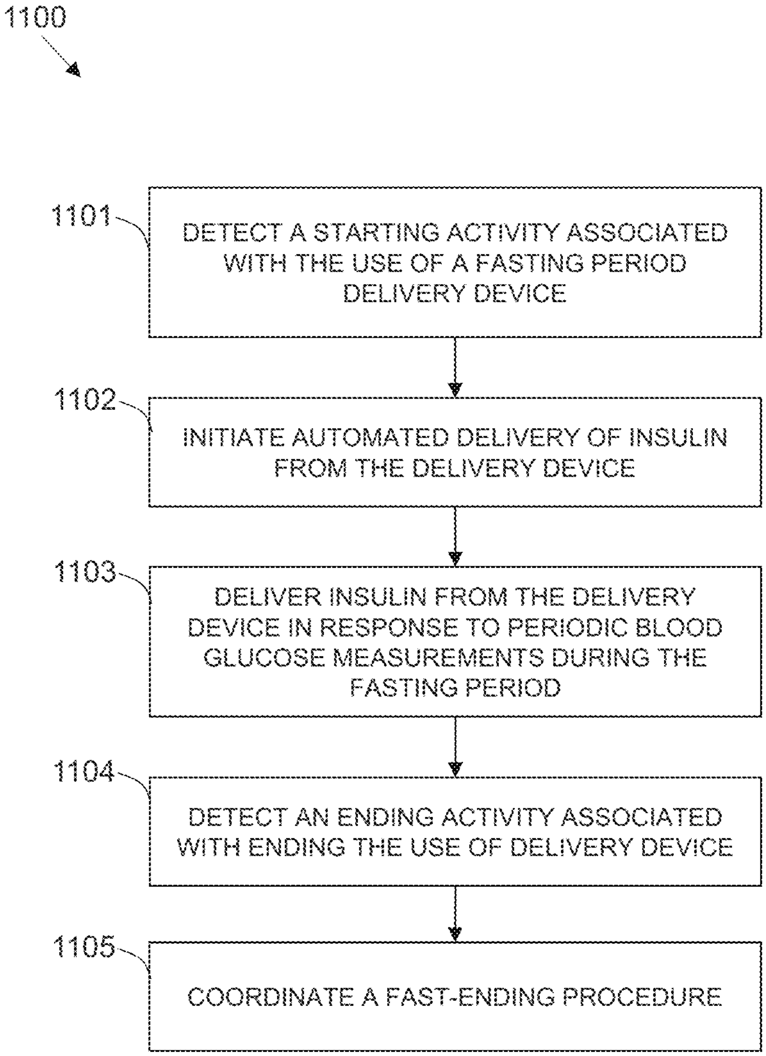
FIG. 11 is a flow diagram of methods of controlling delivery of insulin during a fasting period and/or for coordinating such fasting period insulin management with another therapy modality utilized during a non-fasting period, according to some example embodiments.

Delivery stage component 350 may include an end-procedure component 355 for coordinating an end bolus delivery at the end of the fasting period, for example as shown by dose 130*e* in FIG. 1 and/or as described anywhere in this disclosure (see, e.g., FIGS. 7 and 11). Delivery stage component 350 may also include an end detecting component 356 for detecting an ending activity 150 associated with ending the use of the insulin delivery device 301 as described anywhere in this disclosure. While particular functionality is described or referenced to above for each functional block in FIG. 3, the present disclosure is not so limited and any functionality described in this disclosure may be carried out by one or more of the functional blocks depicted in FIG. 3.

Figure 4:
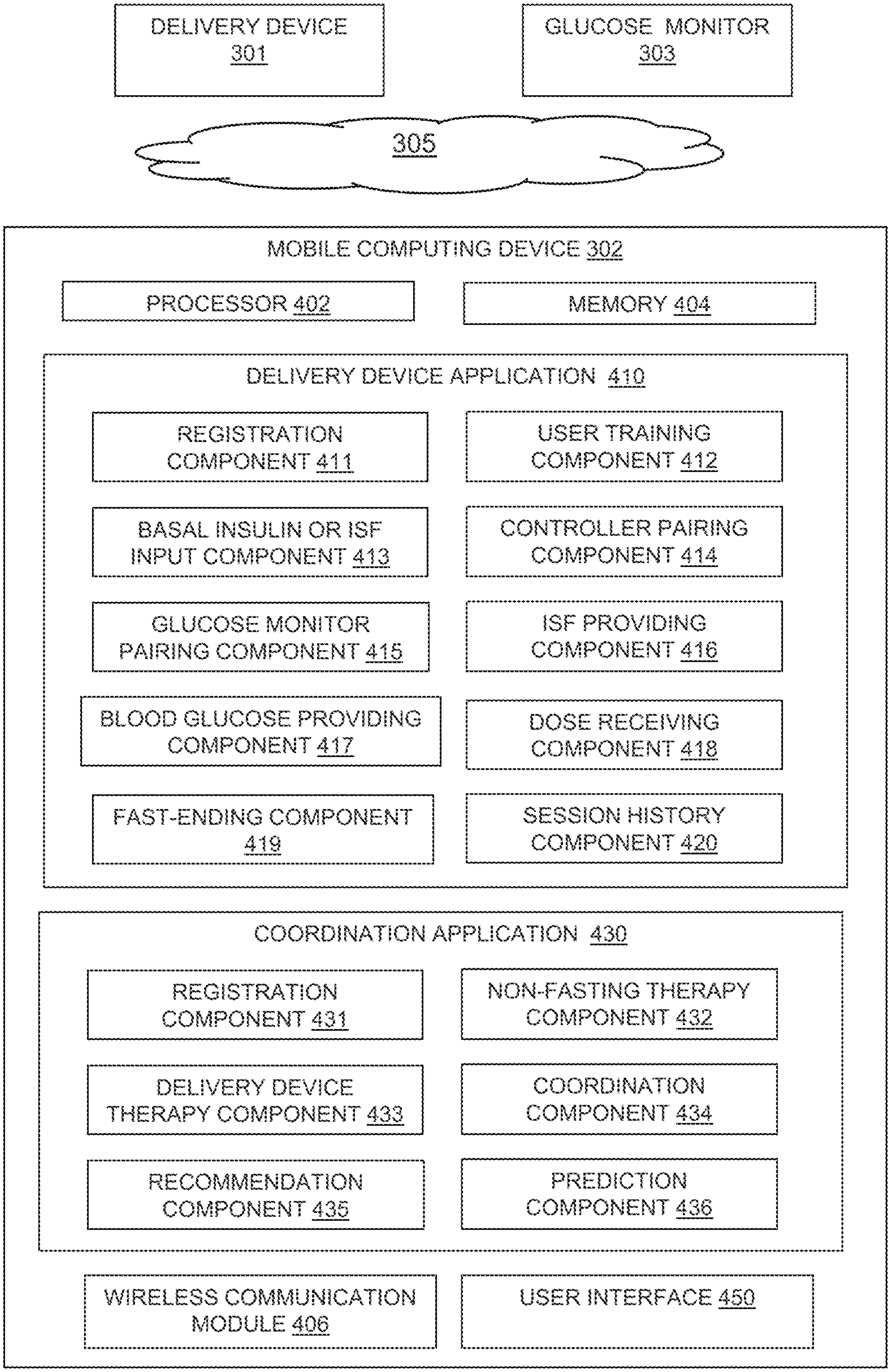
FIG. 4 is a block diagram of a system providing a computer application for interacting with a delivery device for controlling delivery of insulin, according to some example embodiments.

Referring to FIG. 4, a block diagram shows an example embodiment of a system including mobile computing device 302 such as a mobile phone, laptop or desktop computer. The mobile computing device 302 may communicate via wireless network 305 with delivery device 301, which may comprise delivery device 230. Mobile computing device 302 may also communicate via wireless network 305 with glucose monitor 303 for receiving glucose measurement of a user. Mobile computing device 302 may include a wireless communication module 406 configured to facilitate any and all wireless communications with other devices. Mobile computing device 302 may also include a user interface 450 configured to display any indications and/or information to the user and/or receive any information from the user as required, desired and/or described anywhere in this disclosure. In some embodiments, one or more portions or functionalities of the processing of controller 232 including the delivery algorithm may be provided remotely by the mobile computing device 220. In other embodiments, one or more portions or functionalities of the processing of controller 232 including the delivery algorithm may be provided remotely by a cloud server either directly to the controller 232 or in coordination with the mobile computing device 220.

Mobile computing device 302 may include a processor 402 for executing the functions of components described herein, which may be provided by hardware or by software units executing on mobile computing device 302. The software units may be stored in a memory component 404 and instructions may be provided to processor 402 to carry out the functionality of the described components. In some cases, for example in a cloud computing implementation, software units arranged to manage and/or process data on behalf of mobile computing device 302 may be provided remotely. Some or all of the components may be provided by a software application downloadable onto and executable on mobile computing device 302.

A delivery device application 410 may be provided by the hardware or software units for managing the described fasting delivery device as described anywhere in this disclosure. Delivery device application 410 may include a registration component 411 for registering a user of the application as described anywhere in this disclosure. Delivery device application 410 may include a user training component 412 for providing training steps instructing the user how to use a delivery device, including filling from an insulin pen, as described anywhere in this disclosure.

Delivery device application 410 may include a basal insulin input component 413 for prompting and receiving a user input of a total daily basal dose information, e.g., for subsequent use setting an ISF for the user as described anywhere in this disclosure.

Delivery device application 410 may include a controller pairing component 414 for pairing mobile communication device 302 running delivery device application 410 with a controller of delivery device 301. Delivery device application 410 may include a glucose monitor pairing component 415 for pairing mobile communication device 302 running application 410 with blood glucose monitor 303 worn by the user.

Delivery device application 410 may include an ISF providing component 416 for providing the user's ISF to the delivery algorithm of the controller of the delivery device 301 for use in the calculation of the correction doses as described anywhere in this disclosure.

Delivery device application 410 may include a blood glucose providing component 417 for receiving blood glucose measurements as monitored from glucose monitor 303 and sending these to the controller for calculation of correction bolus doses as described anywhere in this disclosure. Application 410 may include a dose receiving component 418 for receiving a record of correction bolus doses given by the delivery device as described anywhere in this disclosure.

Delivery device application 410 may include a fast-ending component 419 for providing a fast-ending procedure in which the delivery device application 410 receives a fast-ending input from the user and may send this input to the controller and may receive details from the controller of a fast-ending bolus dose in order to notify the user with instructions to supplement the delivery device fast-ending dose with their insulin pen or other therapy as described anywhere in this disclosure.

Delivery device application 410 may include a session history component 420 for providing a session history including a display of correction doses given by the delivery device together with the blood glucose measurements and including additional statistics for user information as described anywhere in this disclosure. Session histories for previous sessions may also be provided as described anywhere in this disclosure.

A therapy coordination application 420 may be provided by the hardware or software units for managing the described fasting delivery device. In some embodiments, therapy coordination application 420 may be provided independently of delivery device application 410. In some other embodiments, therapy coordination application 420 may be combined with or interact with delivery device application 410.

Therapy coordination application 430 may include a registration component 421 for registering a user of the application and may record user information relating to the user's insulin requirements as described anywhere in this disclosure. Therapy coordination application 430 may include a non-fasting therapy component 432 for receiving information relating to the non-fasting insulin therapy used by the user in overall period 100 as described anywhere in this disclosure. This may be received from the non-fasting therapy device, such as smart insulin pen 210 (see, e.g., FIG. 1) or from an application governing the use of the non-fasting therapy device. Alternatively, this may be received directly from the user. Therapy coordination application 430 may include a delivery device therapy component 433 for receiving information relating to fasting delivery device 230 delivering correction bolus doses 130*a*-130*e* within fasting period 104 of overall period 100 (see, e.g., FIG. 1) as described anywhere in this disclosure. This information may be received from the controller of the delivery device or from the delivery device application 410.

Therapy coordination application 430 may include a coordination component 434 configured to provide coordination between the non-fasting and fasting therapies and doses as described anywhere in this disclosure. Therapy coordination application 430 may include a recommendation component 435 configured to provide recommendations to the user as described anywhere in this disclosure. Therapy coordination application 430 may include a prediction component 436 configured to provide predictions to the user as described anywhere in this disclosure.

Figure 5:
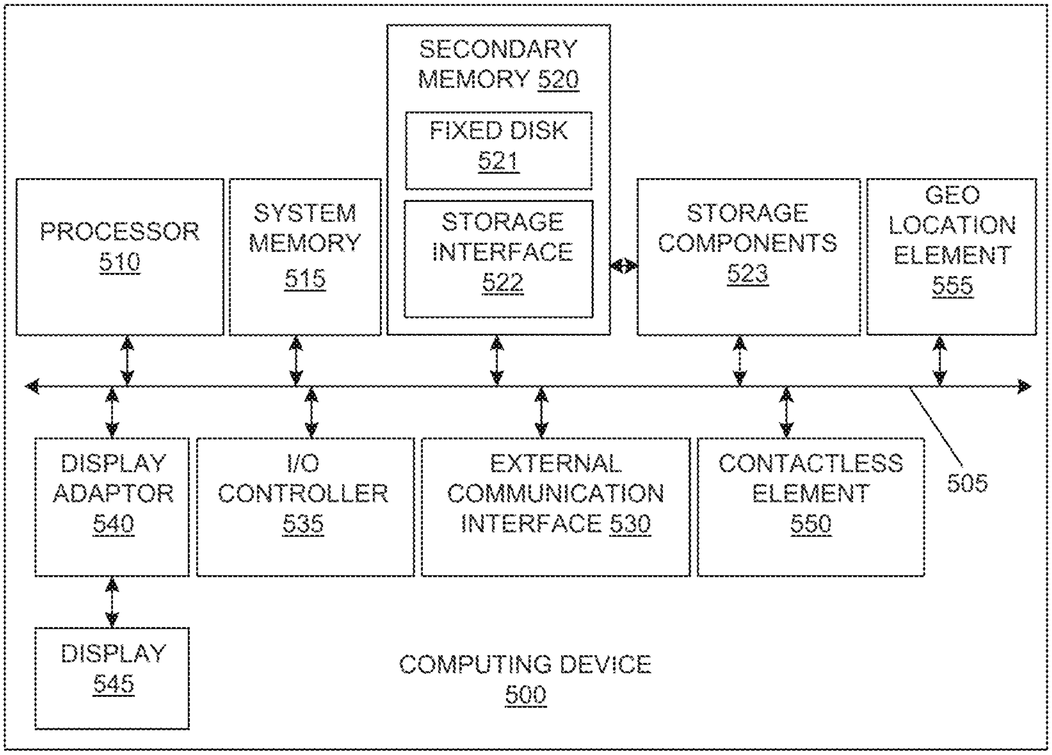
FIG. 5 illustrates an example of a computing device in which various aspects of the disclosure may be implemented, according to some example embodiments.

An example of embodiments where one or more portions or functionalities of controller 232 and/or delivery device 230 are remotely disposed in such an above-mentioned cloud computing system 240 is shown in FIG. 5, as computing device 500. However, the present disclosure is not so limited and FIG. 5 may also illustrate features of controller 232 and/or delivery device 230, of delivery device 301 and/or of mobile computing device 220 or 302 as described anywhere in this disclosure. FIG. 5 illustrates an example of a computing device 500 in which various aspects of the disclosure may be implemented. Computing device 500 may be embodied as any form of data processing device including a personal computing device (e.g. laptop or desktop computer), a server computer (which may be self-contained, physically distributed over a number of locations), a client computer, or a communication device, such as a mobile phone (e.g. cellular telephone), satellite phone, tablet computer, personal digital assistant or the like. Different embodiments of the computing device may dictate the inclusion or exclusion of various components or subsystems described below.

Computing device 500 may be suitable for storing and executing computer program code. The various participants and elements in the previously described system diagrams may use any suitable number of subsystems or components of computing device 500 to facilitate the functions described herein. Computing device 500 may include subsystems or components interconnected via a communication infrastructure 505 (for example, a communications bus, a network, etc.). Computing device 500 may include one or more processors 510 and at least one memory component in the form of computer-readable media. The one or more processors 510 may include one or more of: CPUs, graphical processing units (GPUs), microprocessors, field programmable gate arrays (FPGAs), application specific integrated circuits (ASICs) and the like. In some configurations, a number of processors may be provided and may be arranged to carry out calculations simultaneously. In some implementations various subsystems or components of computing device 500 may be distributed over a number of physical locations (e.g. in a distributed, cluster or cloud-based computing configuration) and appropriate software units may be arranged to manage and/or process data on behalf of remote devices.

The memory components may include system memory 515, which may include read only memory (ROM) and random access memory (RAM). A basic input/output system (BIOS) may be stored in ROM. System software may be stored in the system memory 515 including operating system software. The memory components may also include secondary memory 520. Secondary memory 520 may include a fixed disk 521, such as a hard disk drive, and, optionally, one or more storage interfaces 522 for interfacing with storage components 523, such as removable storage components (e.g. magnetic tape, optical disk, flash memory drive, external hard drive, removable memory chip, etc.), network attached storage components (e.g. NAS drives), remote storage components (e.g. cloud-based storage) or the like.

Computing device 500 may include an external communications interface 530 for operation of computing device 500 in a networked environment enabling transfer of data between multiple computing devices 500 and/or the Internet. Data transferred via the external communications interface 530 may be in the form of signals, which may be electronic, electromagnetic, optical, radio, or other types of signal. External communications interface 530 may enable communication of data between computing device 500 and other computing devices including servers and external storage facilities. Web services may be accessible by and/or from computing device 500 via communications interface 530.

External communications interface 530 may be configured for connection to wireless communication channels (e.g., a cellular telephone network, wireless local area network (e.g. using Wi-Fi™), satellite-phone network, Satellite Internet Network, etc.) and may include an associated wireless transfer element, such as an antenna and associated circuitry. The external communications interface 530 may include a subscriber identity module (SIM) in the form of an integrated circuit that stores an international mobile subscriber identity and the related key used to identify and authenticate a subscriber using computing device 500. One or more subscriber identity modules may be removable from or embedded in computing device 500.

External communications interface 530 may further include a contactless element 550, which is typically implemented in the form of a semiconductor chip (or other data storage element) with an associated wireless transfer element, such as an antenna. Contactless element 550 may be associated with (e.g., embedded within) computing device 500 and data or control instructions transmitted via a cellular network may be applied to contactless element 550 by means of a contactless element interface (not shown). The contactless element interface may function to permit the exchange of data and/or control instructions between computing device circuitry (and hence the cellular network) and contactless element 550. Contactless element 550 may be capable of transferring and receiving data using a near field communications capability (or near field communications medium) typically in accordance with a standardized protocol or data transfer mechanism (e.g., ISO 14443/NFC). Near field communications capability may include a short-range communications capability, such as radio-frequency identification (RFID), Bluetooth™, infra-red, or other data transfer capability that can be used to exchange data between computing device 500 and an interrogation device. Thus, computing device 500 may be capable of communicating and transferring data and/or control instructions via both a cellular network and near field communications capability.

The computer-readable media in the form of the various memory components may provide storage of computer-executable instructions, data structures, program modules, software units and other data. A computer program product may be provided by a computer-readable medium having stored computer-readable program code executable by central processor 510. A computer program product may be provided by a non-transient or non-transitory computer-readable medium, or may be provided via a signal or other transient or transitory means via communications interface 530.

Interconnection via communication infrastructure 505 allows the one or more processors 510 to communicate with each subsystem or component and to control the execution of instructions from the memory components, as well as the exchange of information between subsystems or components. Peripherals (such as printers, scanners, cameras, or the like) and input/output (I/O) devices (such as a mouse, touchpad, keyboard, microphone, touch-sensitive display, input buttons, speakers and the like) may couple to or be integrally formed with the computing device 500 either directly or via an I/O controller 535. One or more displays 545 (which may be touch-sensitive displays) may be coupled to or integrally formed with computing device 500 via a display or video adapter 540.

Computing device 500 may include a geographical location element 555 which is arranged to determine the geographical location of computing device 500. Geographical location element 555 may for example be implemented by way of a global positioning system (GPS), or similar, receiver module. In some implementations the location element 555 may implement an indoor positioning system, using for example communication channels such as cellular telephone or Wi-Fi™ networks and/or beacons (e.g. Bluetooth™ Low Energy (BLE) beacons, iBeacons™, etc.) to determine or approximate the geographical location of the computing device 500. In some implementations, geographical location element 555 may implement inertial navigation to track and determine the geographical location of the communication device using an initial set point and inertial measurement data.

Several embodiments of embodiments contemplated by this disclosure. will now be described in connection with one or more FIGS.

Figure 6:
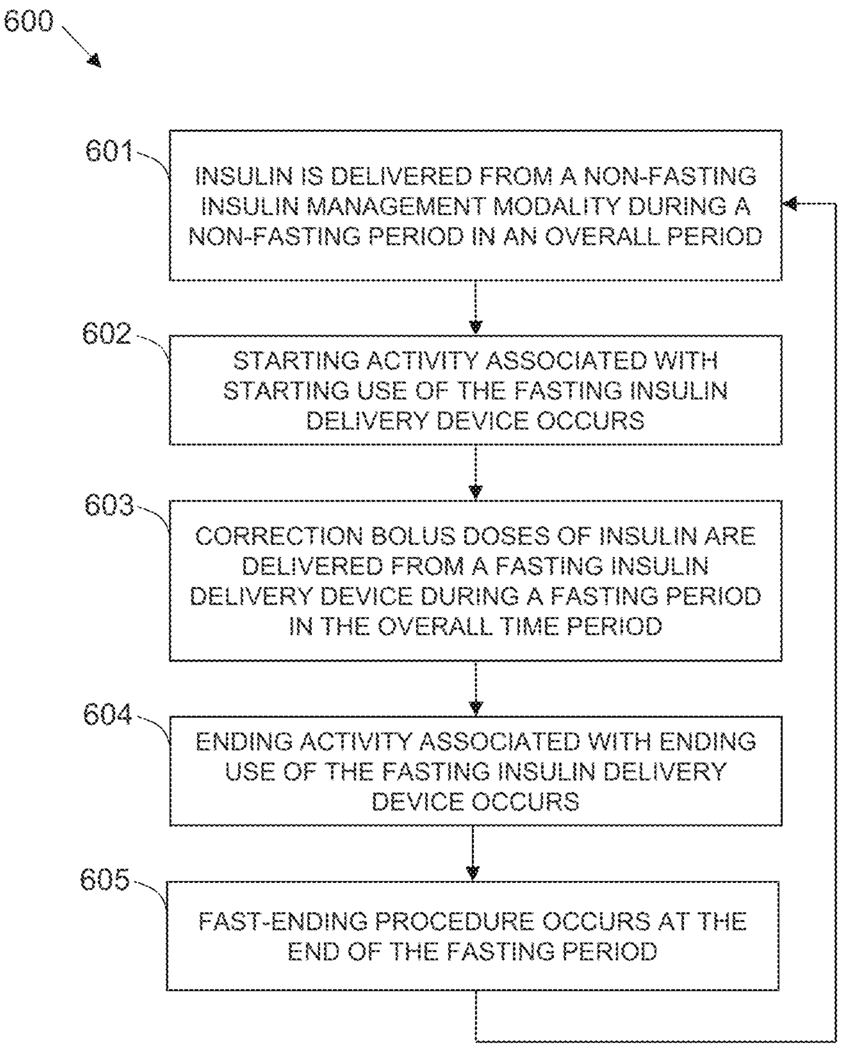
FIG. 6 illustrates a flowchart of an overall process for managing insulin delivery using differing modalities during non-fasting and fasting periods of an overall time period, according to some example embodiments.

FIG. 6 illustrates a flowchart 600 of an overall process for managing insulin delivery using a first modality during non-fasting period 102 and using a second modality during fasting period 104 of overall time period 100 of FIG. 1, according to some example embodiments. All other processes described in this disclosure relate, in one way or another, to this overall process.

At block 601, insulin is delivered from a non-fasting insulin management modality during a non-fasting period in an overall period. For example, as previously described in connection with one or more of FIGS. 1-5, a user may deliver slow-acting basal insulin once every 24 hours **110*a* (or twice every 12 hours 110*a* and 110*b*, based on configuration) via, for example, an insulin pen 210 during non-fasting period 102 of overall period 100 as shown in FIG. 1**.

At block 602, a starting activity associated with starting use of the fasting insulin delivery device occurs. For example, as will be described in more detail below, starting activities 140 may include but are not limited to physical activities carried out by the user in relation to the delivery device, physical changes to the delivery device, activity level of the user satisfying predetermined criteria, and/or occurrence of a pre-set time of the day. The user carrying out such starting activities, and/or detection of such starting activities by one or more devices and/or device components as described herein may play a role in one or more processes for managing insulin delivery using differing modalities during the non-fasting period compared to the fasting period as described anywhere in this disclosure.

At block 603, correction bolus doses of insulin are delivered from a fasting insulin delivery device during a fasting period within the overall time period. For example, as previously described in connection with one or more of FIGS. 1-5, fasting-time wear delivery device 230 may be configured to deliver fast-acting correction doses **130*a*-130*e* during non-fasting period 102 of overall period 100 of FIG. 1. As will be described in more detail below, proprietary delivery algorithms employ the estimation of a quantity termed "assumed insulin on board" and the application of one or more safety factors to one or more of the variables utilized to determine correction doses 130*a*-130*e* to, thereby, enable fasting insulin delivery delivery device 230 to administer insulin in a way that effectively guides the user's blood glucose toward a target range and then maintains blood glucose near the target during fasting period 104 of overall period 100**, while guarding against over-delivery of insulin and attendant hypoglycemia, without the need for information relating to basal insulin rates, carbohydrate ratios, or insulin action times.

At block 604, ending activity associated with ending use of the fasting insulin delivery device occurs. For example, as will be described in more detail below, ending activities may include but are not limited to removal of the wearable insulin reservoir from the body, completion of a predetermined time period of less than a defined time period (for example, 24, 12, 10, 8 or 6 hours), and/or return of the durable portion of the delivery device 230 to charger (e.g., charging station) 231 (see, e.g., FIG. 2). The user carrying out such ending activities, and/or detection of such ending activities by one or more devices and/or device components as described herein may play a role in one or more processes for managing insulin delivery using differing modalities during the non-fasting period compared to the fasting period as described anywhere in this disclosure.

At block 605, a fast-ending procedure occurs at the end of the fasting period. For example, a fast-ending procedure for the user's discontinued use of the insulin delivery device may deliver at least a portion of a fast-ending bolus at the end of the session (e.g., correction dose 130*e* in FIG. 1). By way of example and not limitation, a user may wake with elevated glucose because the delivery of correction doses was conservative, operating under an assumption that the user would still sleep for several more hours, in which case, a final fast-ending correction bolus not associated with a meal (or a portion of such a correction dose comprising the remaining insulin in the delivery device) may be administered. Alternatively, such a final fast-ending correction bolus may be a hybrid corrective and meal bolus, administered at or near the end of fasting period 104 to both correct waking elevated glucose and, further, in expectation of a meal being eaten during the subsequent non-fasting period 102 after fasting period 104 has ended.

As overall period 100 is a recurring period (e.g., a 24-hour period in some cases), block 605 advances back to block 601 at the initiation of the non-fasting period 102 of the next overall period 100 that immediately follows the fasting period 104. Moreover, the recurring nature of overall period 100 necessitates a transition from the non-fasting period 102 and its associated mode of insulin administration (e.g., MDIs) to the fasting period 104 and its automatic administration of correction doses 130*a*-130*e*, as well as another transition back to the next non-fasting period 102 and its associated mode of insulin administration at the end of fasting period 104. Accordingly, some methods, devices and systems configured for integrating a supplementary method of insulin administration outside fasting period 104 may include coordination of one or more correction doses 130*a*-130*e* provide by delivery device 230 during fasting period 104 with one or more basal doses 110*a*, 110*b* or meal doses 120*a*-120*d* provided via the non-fasting modality (e.g., insulin pen 210 of FIG. 2) during non-fasting period 102.

Example Correction Dose Calculating Method

Example embodiments of a method of calculating one or more correction doses 130*a*-130*e* are described below. In general, insulin correction dose calculation is determined at least in part utilizing equation (1) below and, in some cases, further applying one or more safety factors to one or more of the variables utilized therein, as described anywhere in this disclosure, to effectively guide a user's blood glucose toward a target range and then maintain the user's blood glucose at or near the target during fasting period 104 of overall period 100.

$$\text{Dose\_Calculation}=[(\text{Current\_BG}-\text{Target\_BG})/\text{ISF}]-\text{IOB} \quad (1)$$

The Dose_Calculation is a calculated amount of additional insulin needed to decrease a user's current blood glucose level to a target blood glucose level as described anywhere in this disclosure.

The Current_BG is a measured blood glucose value of the user that may be evaluated before applying in equation (1) as described anywhere in this disclosure.

The Target_BG is a target for the user's blood glucose level.

ISF (insulin sensitivity factor) is a user-specific factor indicating how many milligrams per deciliter (mg/dl) one unit of insulin is expected to lower the user's blood glucose.

IOB comprises the sum of two subtypes of IOB: (1) assumed IOB, which is an amount of externally administered insulin that would be needed to correct the user's actual initial BG to the Target_BG and that is assumed to have already been delivered to the user; and (2) delivered IOB, which is calculated based on insulin actually delivered to the user by the fasting period delivery device 230 as described herein. Since insulin in metabolized over time, IOB is adjusted over time based on known duration of insulin action (DIA). DIA is how long a bolus of insulin takes to finish lowering blood glucose. The DIA time starts when a bolus is given and ends when the bolus is no longer lowering blood glucose levels. An accurate DIA minimizes insulin stacking and low blood sugar (hypoglycemia), which can happen when boluses are given too close together.

In some embodiments, a fixed setting for DIA may be used to remove the opportunity for significant DIA error due to incorrect estimation. For example, the pharmacokinetics/pharmacodynamics (PK/PD) of rapid acting insulin has been well-characterized as having a PK/PD peak at approximately 65 min, which correlates to a DIA of 6 hours. Accordingly, DIA may be fixed at a value between about 5 and 7 hours because the delivery device only uses fast-acting insulin, preferably fixed at a DIA of 6 hours. In some embodiments, this may be combined with a fixed time constant (of about 60-70 minutes) for IOB calculation, as will be described in more detail below, to avoid insulin stacking.

The result of the above equation, Dose_Calculation, is an insulin correction dose which may be divided into smaller amounts in the form of delivery portions (e.g., correction doses 130*a*-130*e* in FIG. 1) based on a maximum delivery rate over a predetermined or predefined time interval (e.g., no more than 0.1, 0.2, 0.3, 0.4, 0.5, 0.6, 0.7, 0.8 units of insulin per, e.g., 5, 10, 15 minutes or per number of intervals at which glucose data is being received from a CGM).

According to equation (1) above, needed insulin yet to be delivered is ultimately determined based on a difference, between a representation of the user's actual real-time blood glucose levels (or sufficiently temporally recent, e.g., within 5 minutes) and a target blood glucose, that is then scaled according to a representation of the user's insulin sensitivity and further reduced by an amount of insulin that is calculated to already (or still) be active in the user's body. But a central focus of disclosed methods for calculating and/or controlling the delivery of one or more correction doses of insulin to a user during the fasting period 104 is to guard against over-delivering, or calculating to over-deliver, insulin and to guard against the attendant hypoglycemia, especially because the user is expecting to be sleeping during a large portion of fasting period 104 and will not be eating to provide any exogenous counter balance to an insulin overshoot into hypoglycemia. This makes effectively steering blood glucose toward a safe and healthy target in a suitable timeframe difficult because many unknown factors can affect a user's actual blood glucose levels and short-term dynamics. For example, user's short-term blood glucose readings can include fast, and sometimes aberrant, swings that do not always accurately reflect a long-term trend in the user's current blood glucose levels, or the amount of actual insulin on board still acting on those blood glucose levels. Compounding the difficulty, the user's insulin sensitivity can vary by time of day and, certainly, based on other physiological factors that are difficult to account for individually and directly including but not limited to stress (e.g., cortisol release).

Accordingly, methods for calculating and/or controlling the delivery of one or more correction doses of insulin to a user during the fasting period 104, and devices and/or systems configured to carry out such methods, solve various technical problems at least in part by utilizing a user's initial condition(s) (e.g., the user's initial blood glucose levels) to determine an amount of insulin that is assumed to still be active in the user's system (assumed IOB) from the prior non-fasting period 102. This assumption of initial insulin sufficiency in the face of initially elevated blood glucose levels prevents insulin stacking at the beginning of the fasting period 104 that would result from inappropriately dosing insulin in response to initially above-target blood glucose levels for which insulin has already been administered.

Moreover, insulin has a finite speed of action decreasing blood glucose levels. In other words, it takes a non-negligible period of time for delivered insulin to decrease blood glucose levels. Accordingly, even the most accurate current blood glucose levels are not necessarily accurate indicators of what actual blood glucose levels will be even a short period of time in the future without knowledge of actual insulin already on board for a particular user. And over time the body metabolizes insulin on board, decreasing its effectiveness at lowering blood glucose levels. Accordingly, even the most accurate current blood glucose levels and actual insulin on board are not necessarily accurate indicators of what actual blood glucose levels will be even a short period of time in the future without knowledge of actual determined insulin action (DIA) times for a particular user. For at least these reasons, utilizing the most accurate actual blood glucose levels at each time point (e.g., each CGM BG reading) may not necessarily best accomplish a goal of guarding against over-delivering insulin or guarding against calculating to over-deliver insulin. Rather, guarding against over-delivering insulin or guarding against calculating to over-deliver insulin may be better achieved by utilizing a processed, evaluated and/or filtered proxy of the user's actual blood glucose levels that more accurately represents the long-term trends of the user's actual blood glucose levels in a way that biases against the over-delivery of insulin, while also attenuating, eliminating or otherwise filtering out short-term noise and/or aberrations. Such processed, evaluated and/or filtered proxies of actual blood glucose may be called evaluated blood glucose herein.

Such methods, devices and/or systems also solve various technical problems at least in part by utilizing one or more safety factors to dynamically adjust (e.g., scale and/or translate) one or more of the variables utilized to determine insulin dosing (e.g., target blood glucose level, ISF and/or the assumed and/or delivered portions of IOB) to guard against over-delivering, or calculating to over-deliver, insulin and to guard against the attendant hypoglycemia.

Referring to FIG. 7, a flow diagram 700 shows an example embodiment of a method of controlling the delivery of insulin from a fasting-time wear delivery device, for example, delivery device 230 of FIG. 2. The method may be utilized to deliver insulin during a fasting period 104 from delivery device 230 intended to be utilized only during fasting period 104. No basal doses of insulin are given by delivery device 230. Such a method may solve a problem of accounting for insulin on board from non-fasting delivery modalities without any user interaction or input, and without any prior, or direct knowledge of the amount of insulin actually administered to the user from such non-fasting delivery modalities. Such a method may be carried out at and/or by a controller, such as controller 232 of delivery device 230 shown in FIG. 2, at and/or by delivery device 301 or mobile computing device 302 as shown in FIGS. 3 and/or 4, and/or remotely at and/or by a server, computing device, or the like, such computing device 500 shown in FIG. 5, instructions then being sent to the controller. In some embodiments, certain steps may be carried out by such an above-described controller of the delivery device and/or with some of the steps carried out remotely to the controller. Accordingly, in some embodiments, such methods may be carried out in cooperation with such an above-described controller with a user application provided on a user's mobile computing device, for example mobile computing device 301.

While not shown in flowchart 700, such a method may include delivery device 230 detecting its own activation, for example and not limitation, when the user starts to wear device 230. Alternatively, where one or more steps and/or calculation procedures are carried out remotely by another device, such as mobile device 220 or remote cloud device 240, such a method may include detection or receiving notification, by the other device, of such activation of delivery device 230. For example, in some embodiments, activation component 336 of delivery device 301 of FIG. 3 may be configured to perform such detection.

The method may include an initialization stage 710 in which various parameters and safety factors are set-up for the delivery algorithm, a delivery stage 720 in which correction dose(s) (see, e.g., 130*a*-130*e* in FIG. 1) are calculated and/or delivered to the user, and a fast-ending procedure 730 in which any appropriate fast-ending bolus may be determined and/or delivered to the user. In some embodiments, some steps, or safety factors, of the initialization stage 710 may be updated during the delivery stage 720 and/or the fast-ending procedure 730. In some embodiments, initialization component 330 of delivery device 301 of FIG. 3 may be configured for initialization stage 710 and delivery stage component 350 may be configured for delivery stage 720.

In initialization stage 710, block 711 includes receiving an initial patient insulin sensitivity factor (ISF) or estimating ISF from a received patient total daily basal dose (TDBD). In some embodiments, the controller may receive this initial patient ISF from the patient, from a doctor, or from a connected device, such as a user application or another insulin therapy device, such as smart insulin pen 210 of FIG. 2. In some such embodiments, initial patient ISF may be the only patient input other than periodic blood glucose measurements, which greatly simplifies user interaction with devices and systems of this disclosure. In some embodiments, ISF receiving component 331 of delivery device 301 of FIG. 3 may be configured to perform the functions of block 711.

In some embodiments, the ISF may, instead, be derived from total daily basal dose (TDBD) information, or how much basal insulin the patient took over the last 24 hours, as TDBD is typically constant from day to day for a particular user. Such an example period is shown as overall period 100 in FIG. 1. The TDBD information may be provided by the user or a doctor via a user application or by a smart insulin pen, such as pen 210 of FIG. 2. In such embodiments, block 711 may include receiving TDBD (e.g., the sum of MDIs 110*a*, 110*b* in FIG. 1) and estimating ISF from the received TDBD. For example, strong relationships exist between TDBD, total daily dose (TDD), and ISF, as set forth by formulas (2)-(4) below:

$$ISF=800/TDBD \quad (2)$$

$$TDBD=0.47\times TDD \quad (3)$$

$$ISF=1700/TDD \quad (4)$$

In some embodiments, ISF may be determined based at least in part on a body weight of the user. In some embodiments, the ISF of the user may be learned during use of the delivery device 230. In some embodiments, an ISF profile may vary over time as a user's ISF may vary for different times of the day, for example, many people are more insulin resistant in the morning, which requires a stronger correction factor. The ISF profile may use a learning algorithm configured to set and/or adjust the ISF during a delivery session or in advance for a next delivery session.

Block 712 includes receiving a first blood glucose measurement. For example, blood glucose measurements may be received periodically from a glucose monitor (e.g., CGM 205 in FIG. 2). In some embodiments, BG receiving component 351 of delivery device 301 of FIG. 3 may be configured to perform the functions of block 712. As will be described in more detail below, an initial blood glucose measurement, or set of initial blood glucose measurements, at or sufficiently temporally near the beginning of fasting period 104 may be utilized to determine an assumed IOB, and in some cases one or more safety factors for variables utilized in determining correction dosing, in subsequent steps.

Block 713 includes setting the blood glucose target and one or more safety factors. For example, as stated above, target blood glucose may be set and then any one or more of target blood glucose, ISF and IOB may be adjusted by applying a safety factor to, thereby, ultimately steer or bias insulin dosing, or calculation of such dosing, to guard against over-delivery and inducement of hypoglycemia. In some embodiments, safety factor component 332 of delivery device 301 of FIG. 3 may be configured to perform the functions of block 713. For example, an additional 20 mg/dL safety factor or bias above the typical 120 mg/dL BG target may be implemented such that dose calculations are performed based on a 140 mg/dL fixed target to further safeguard against hypoglycemia. In some embodiments, such safety factors may be based at least in part on a difference between this first blood glucose measurement and the target blood glucose. In some embodiments, such safety factors may be a percentage adjustment, such as 5%, 10%, 15% or 20%, from a baseline value. In some embodiments, the target glucose is also fixed and cannot be modified by the user and may have an additional safety factor.

For example, in some embodiments, target blood glucose may be set a predetermined or constant value for all users, or at a respective one of a plurality of constant values for each of a plurality of classifications of user, at the beginning of fasting period 104. In some embodiments, target blood glucose is set based at least in part on the first blood glucose measurement received in block 712, for example, initially setting or adjusting target blood glucose higher for higher first blood glucose measurements and relatively lower for relatively lower first blood glucose measurements. In some embodiments, a fixed or constant valued glucose target means the method does not allow the user to manually input or modify the glucose target value.

Regarding application of a safety factor to target blood glucose, in some embodiments, target glucose levels may be elevated compared to standard clinical recommendations (for example, by applying a scaling factor that adds 5, 10, 20, 25% to standard recommended 100-120 mg/dL (e.g., 130-180 mg/dL)). Such a safety factor may help account for expected BG variability due to sensor noise, basal drift, and dosing accuracy. In some embodiments, target glucose levels may begin at an initial value, as here, and adjust over fasting period 104 as will be described in more detail in connection with block 723 below.

In some embodiments, a safety factor (e.g., of 5, 10, 15, 20, 25%) may be applied to the ISF, which results in more conservative calculation of insulin delivery amounts. In some embodiments, ISF may be initially set at a conservative default and/or predetermined value (e.g., a relatively high ISF that is biased toward lower insulin dosing) and adjusted and/or personalized over time, for example, based on a difference between actual or evaluated blood glucose measurements and expected blood glucose.

As will be described in more detail below, safety factors may also be applied to actual blood glucose measurements in the form of filtering and/or any other modification thereto as described anywhere in this disclosure. However, such adjustments are largely discussed as evaluating blood glucose measurements at block 722. Similarly, application of any safety factor to the calculated resultant correction dose may be applied at block 725 by limiting the correction dose based on a maximum delivery rate.

Block 714 includes determining insulin on board (IOB) including assumed IOB. In some embodiments, assumed IOB component 344 of delivery device 301 of FIG. 3 may be configured to perform the functions of block 714. During initialization stage 710, at block 714, insulin on board is assumed to have been provided by the non-fasting insulin therapy in the non-fasting period 104 prior to fasting period 104 and is assumed to have been provided in sufficient quantity to reduce the actual blood glucose of the user from the first blood glucose measurement, or set of first blood glucose measurements, to the target blood glucose over fasting period 104.

An assumed external IOB is based on a hypothetical, or assumed, amount of external insulin needed to correct the user's hyperglycemia based on a comparison of current BG (or current evaluated BG) to target BG according to equation (6), as derived from equation (5) below:

$$[(\text{Current\_BG}-\text{Target\_BG})/\text{ISF}]-\text{IOB}=0 \tag{5}$$

$$\text{Assumed IOB}=[(\text{Current\_BG}-\text{Target\_BG})/\text{ISF}] \tag{6}$$

The assumed external IOB may be calculated from a difference, between current blood glucose (or current evaluated blood glucose as described anywhere in this disclosure) and the target blood glucose, scaled by the ISF, as set at block 711 and/or as adjusted at block 713 and not derived from known external insulin. In some embodiments, the first blood glucose value(s) on which the assumed IOB is based may be averaged over a set of first blood glucose measurements to filter transient and/or acute changes. In some embodiments, such a set of first blood glucose measurements may be filtered to exclude outlier values and/or excluding such outlier values from being used in such a rolling average. As described above, accounting for an assumed initial IOB sufficiency means the controller does not need to accept or use a known amount of external IOB info from the user. Accordingly, the correction dose calculation may be accomplished without any external IOB input or knowledge whatsoever. The assumed IOB for at least an initial period does not include insulin input from any previous dosing. An initial assumed IOB determined from equation (5) above is also simpler for the user and reduces user error.

Moreover, assumed IOB may also function as a safety factor in that the IOB in equation (5) is initially assumed, or set, equal to assumed IOB. In this way, when such a safety factor is embodied as an assumed external IOB that decays over time, any dose calculation over 0 going forward (or a minimum threshold that delivery device 230 is configured to deliver, such as 0.1 units of insulin) represents an unexpected BG, or incomplete external IOB, which may be safely compensated for by delivering the difference (e.g., 0.1 unit insulin).

The use of MDI (or any other insulin therapy) during non-fasting period 102 implies the existence of external IOB. Therefore, delivery devices functioning without assumed IOB or without a known IOB, would be high risk as it would be uninformed by the external insulin amount. In some embodiments, IOB may be known from the first therapy used during non-fasting period 102. Accordingly, in such embodiments, an assumed IOB calculation may not be required.

Block 715 includes delivering the first correction dose having zero units. For example, as stated above, assumed IOB is initially determined based the assumption of initial IOB sufficiency. Accordingly, the first correction dose, during and/or at the end of initialization stage 710, would not include any insulin delivery. Delivery stage 720 follows.

During the delivery stage 720, at block 721, blood glucose measurements are periodically received, for example, from a glucose monitor such as CGM 205 in FIG. 2. In some embodiments, BG measurement receiving component 351 of delivery device 301 of FIG. 3 may be configured to perform the functions of block 721.

As stated above, guarding against over-delivering insulin or guarding against calculating to over-deliver insulin may be better achieved by utilizing a processed, evaluated and/or filtered proxy of the user's actual blood glucose levels that more accurately represents the long-term trends of the user's actual blood glucose levels while also attenuating, eliminating or otherwise filtering out short-term noise and/or aberrations. Accordingly, at block 722, the periodically received blood glucose measurements (or a subset thereof) are evaluated. For example, the periodically received blood glucose measurements may be processed and/or filtered as described below or anywhere else in this disclosure in order to obtain a proxy of the user's actual blood glucose levels that more accurately represents the long-term trends of the user's actual blood glucose levels while also attenuating, eliminating or otherwise filtering out short-term noise and/or aberrations.

Accordingly, at block 722, received blood glucose measurements are evaluated. While such evaluation may be carried out by delivery device 230 (e.g., controller 232), mobile device 220 and/or computing device 500, in some embodiments, such evaluation of blood glucose measurements as described anywhere in this disclosure, or portions thereof, may be carried out by CGM 205. In some embodiments, BG measurement evaluating component 352 of delivery device 301 of FIG. 3 may be configured to perform the functions of block 722.

In some embodiments, evaluating comprises smoothing received blood glucose measurements utilizing a low pass filter to reduce the effect of noise and abrupt perturbations. For example, one or more received blood glucose measurements may each be replaced by a rolling average of the received blood glucose measurement and a predetermined number of prior blood glucose measurements.

In some embodiments, evaluating received blood glucose measurements comprises filtering increasing blood glucose values while not filtering decreasing blood glucose values. For example, a true CGM value may be used if it is less than a rolling average of the true CGM value and a predetermined number of prior CGM values, so decreasing BG values are accounted for immediately, but the rolling average may be used where the GM value is greater than the rolling average to avoid basing insulin dosing on localized blood glucose peaks. Peak filtering provides a double-sided safety on CGM values used for decision making by providing additional filtering/smoothing for increasing glucose values than for decreasing glucose values. Such double-sided safety can also be useful when determining or adjusting IOB, as will be described below, because if an actual IOB is lower than estimated, delivering insulin is safe; however, if an actual IOB is higher than estimated, no insulin will be delivered.

In some embodiments, evaluating received blood glucose measurements comprises adjusting for a long-term downward trend over a period of hours in the fasting period 104. For example, when true BG values are trending downward over time (e.g., for 6 hours), the true blood glucose value may be adjusted downward based on and to reflect the forward projection of the downward trend, effectively reducing insulin dosing where BG is already drifting downward, protecting against inappropriate over-delivery of insulin and, thereby, guarding against inducing hypoglycemia. This provides correction for basal drift caused by incorrectly titrated basal insulin dosing, meal bolus dosing, and/or other physiological factors in that it compensates for (backs out) insulin effect to account for trend adjustments.

However, adjusting for long-term drift during fasting period 104 may, in some approaches, require determination of an appropriate slope of the drift to be compensated. One way in which this slope may be determined is through a linear regression analysis of a least mean squares fit for all or a subset of true, or evaluated, blood glucose measurements from the timeframe during which the drift slope is desired. Several additional ways to evaluate received blood glucose measurements are described in connection with FIGS. 8-10 at the end of the discussion of FIG. 7.

At block 723, IOB, target blood glucose, and/or one or more of the above-mentioned safety factors may be adjusted. For example, assumed IOB varies based on time elapsed from initialization of the delivery device and the duration of insulin action (DIA) so that the assumed IOB should, generally, decrease over fasting period 104. In some embodiments, correction dose calculating component 353 of delivery device 301 of FIG. 3 may be configured to perform the functions of block 723.

Similar to as described above, assumed IOB may function as a safety factor in that the IOB in equation (1) is assumed equal to assumed IOB, decayed based on DIA time courses, +any active device IOB still in the user's system, with the active device IOB being the amount of insulin delivered since the beginning of use of delivery device 230 in the current fasting period 104 (e.g., those of correction doses 130*a*-130*e* of FIG. 1 that have already been administered to the user), also decayed based on DIA time courses. In this way, when the safety factor is embodied as IOB that decays over time, any dose calculation over 0 (or a minimum threshold that delivery device 230 is configured to deliver, such as 0.1 units of insulin) represents an unexpected BG, or incomplete external IOB, which is safely compensated for by delivering the difference (e.g., 0.1 unit insulin).

In some embodiments, assumed IOB may be compared with actual duration of insulin action (DIA) calculated from actual BG (or from an evaluated representation of actual BG as described anywhere in this disclosure). In other embodiments, the actual BG is compared with an expected BG calculated from DIA. These values and/or their comparisons may be used to create, calculate, determine, set, reset and/or select safety factors for any variable utilized in the calculation of correction doses 130*a*-130*e*, or to learn from the user's experience of previous safety factor values in an effort to bias insulin dose calculation toward delivery of less insulin in the context of any unknowns that can affect blood glucose.

As stated above, an operating assumption is that assumed IOB is sufficient to bring initial blood glucose measurements back down to the blood glucose target over time. Accordingly, in some embodiments, if blood glucose measurements received within a predetermined interval of time after the start of fasting period 104 (or their evaluated proxies) rise, rather than fall, from their level during the initiation phase 710 (when assumed IOB was initially set), assumed IOB may be recalculated and/or adjusted upwards at block 723 based on the increased blood glucose measurement(s) and/or the evaluated proxy(ies) thereof. Such adjusting upward, or recalculating, of assumed IOB effectively reduces prospective insulin dosing where initial blood glucose measurements received during initialization phase 710 underrepresented the actual upward trajectory of the blood glucose for which insulin may have already been administered during the prior non-fasting period 102 utilizing the non-fasting modality. In some embodiments, IOB determining component 433 and/or Assumed IOB component 344 of delivery device 301 of FIG. 3 may be configured to perform one or more functions of block 723.

In some embodiments, target glucose levels are varied over time based at least in part on time elapsed from initialization of the delivery device. Accordingly, the target glucose level may be decreased over time during fasting period 104 (see, e.g., FIG. 1). In some embodiments, a rate at which the target glucose is decreased may be based at least in part on an assumption and expectation that glucose levels are currently being lowered by remaining assumed IOB.

In some embodiments, ISF varies over time. For example, many people are more insulin resistant in the morning, making a lower ISF desirable in the morning portion of fasting period 104. Accordingly, in some embodiments, ISF may be set or reset at block 723 based on the time of day. The ISF profile may use a learning algorithm configured to adjust the ISF based at least in part on histories of effective ISF, blood glucose measurements and/or blood glucose target(s) for the user during one or more prior fasting periods 104. In some embodiments, ISF may be initially set at a conservative default and/or predetermined value (e.g., a relatively high ISF) and adjusted/personalized over time based at least in part on comparisons between Actual and Expected BG trends/profiles in the context of correction doses 130*a*-130*e* that have already been delivered to the user during the fasting period 104.

At block 724, a correction dose is calculated based on a difference between an evaluated blood glucose measurement and a target blood glucose, the difference adjusted by the user ISF and reduced by a determined insulin on board. In some embodiments, correction dose calculating component 353 of delivery device 301 of FIG. 3 may be configured to perform the functions of block 724. For example, as previously described, a correction dose for insulin delivery may be calculated utilizing equation (1), as reproduced below:

$$\text{Dose\_Calculation}=[(\text{Current\_BG}-\text{Target\_BG})/\text{ISF}]-\text{IOB} \quad (1)$$

As described above, the evaluated blood glucose measurement may be an output or result of applying one or more evaluations, filters and/or processing steps, as described anywhere in this disclosure, on one or more true blood glucose measurements received for example from CGM 205 (see, e.g., FIG. 2), and/or on one or more blood glucose measurements that have already been evaluated and are already an output or result of applying one or more evaluations, filters and/or processing steps, as described anywhere in this disclosure. In other words, multiple evaluations may be performed on blood glucose measurements, as described anywhere in this disclosure, to ultimately arrive at the evaluated blood glucose measurement utilized in equation (1) above. Further, also as described above, any one or more of the target blood glucose, ISF and/or IOB may have values that were set and/or adjusted based at least in part on application and/or setting of one or more safety factors as described above.

Based at least in part on equation (1) above, a dose calculator following a process described by and/or related to process 700 may compare the evaluated blood glucose value to the target blood glucose to obtain a difference. And the difference may be adjusted, e.g., scaled, by a user insulin sensitivity factor. Adjusting or scaling this difference by the user insulin sensitivity factor serves a function of transforming the difference, having units of blood glucose concentration, into a value having units corresponding to an insulin dose and, specifically, an estimated insulin dose forecasted to reduce the difference substantially to zero for that user. As described above, this resultant dose amount is compensated, or reduced, by an amount of insulin determined to already be on board to arrive at an actual insulin dose that may be delivered to the user over a period of time to effectively guide the user's blood glucose toward the target during fasting period 104 of overall period 100, while guarding against over-delivery of insulin and attendant hypoglycemia. Such compensation, or reduction, serves a function of transforming the above-described resultant dose, e.g., a total hypothetical correction insulin dose, into the portion thereof that is determined yet to be introduced to the user's system, in other words, transforming a hypothetical correction insulin dose that is specific to the user's actual insulin sensitivity and to the user's actual blood glucose level (but not specific to the user's actual insulin levels) into an actual correction insulin dose to be dispensed to the user over time that is specific to the user's actual insulin sensitivity, the user's actual blood glucose level, and the user's actual insulin levels (i.e., the user's current insulin on board).

At block 725, the correction dose is limited if greater than a maximum delivery rate. In some embodiments, correction dose limiting component 354 of delivery device 301 of FIG. 3 may be configured to perform the functions of block 725. For example, the correction dose may be divided into portions 130*a*-130*e* comprising up to a maximum amount of insulin to be delivered over a given time period. In some embodiments, the given time period may be an interval at which blood glucose measurements are received.

Block 726 comprises delivering at least a portion of the correction dose. In some embodiments, dose delivery mechanism 331 of delivery device 301 of FIG. 3 may be configured to perform the functions of block 726. For example, in reference to FIGS. 1 and 2, correction dose 130*a* may be delivered to the user by delivery device 230. If the correction dose is greater than the maximum per delivery period, correction dose 130*a* may comprise just a portion of the calculated correction dose that is equal to the maximum per delivery period.

Block 727 comprises continuously iterating for the next blood glucose measurement during the delivery stage 720 to accommodate periodically received blood glucose measurements. In one embodiment, a correction dose may be divided into a number of smaller portions to meet the maximum for delivery and one of the smaller portions may be given. When a next received blood glucose measurement is received, the method may include determining whether to deliver the next divided portion or whether to adjust the dose based on an updated calculation, thereby, providing a gradual correction that is more likely to avoid hypoglycemia risk.

The method may further include a fast-ending procedure 730 for accommodating a fast-ending bolus as described anywhere in this disclosure. For example, a fast-ending procedure for the user's discontinued use of the insulin delivery device may deliver at least a portion of a fast-ending bolus at the end of the session (e.g., correction dose 130*e* in FIG. 1).

By way of a use case example and not limitation, a user may wake with elevated glucose because the delivery of correction doses was conservative, operating under an assumption that the user would still sleep for several more hours, in which case, a final fast-ending correction bolus not associated with a meal (or a portion of such a correction dose comprising the remaining insulin in the delivery device) may be administered.

By way of another, alternative use case example, such a final fast-ending correction bolus may be a hybrid corrective and meal bolus, administered at or near the end of the fasting period 104 to both correct waking elevated glucose and, further, in expectation of a meal being eaten during the subsequent non-fasting period 102 after the fasting period 104 has ended, for example as described in more detail in connection with FIGS. 14-16.

Figure 8:
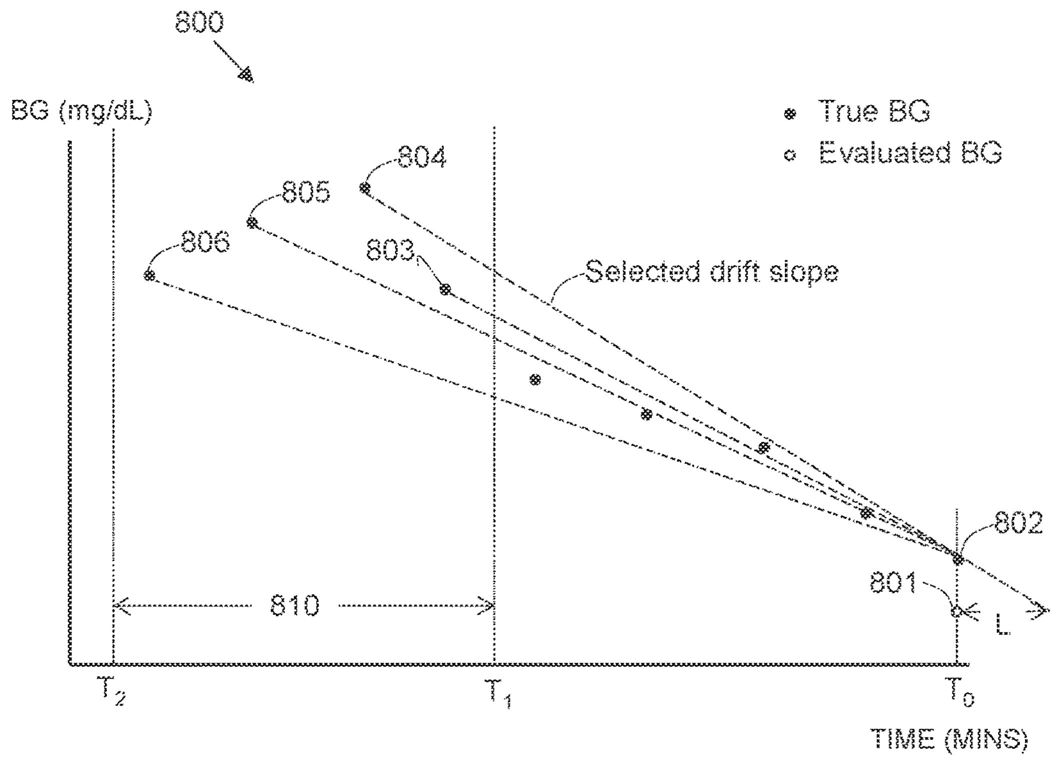
FIG. 8 is a graph illustrating a use case for determining drift slope of blood glucose measurements over a given in a timeframe, according to some example embodiment.
Figure 9A:
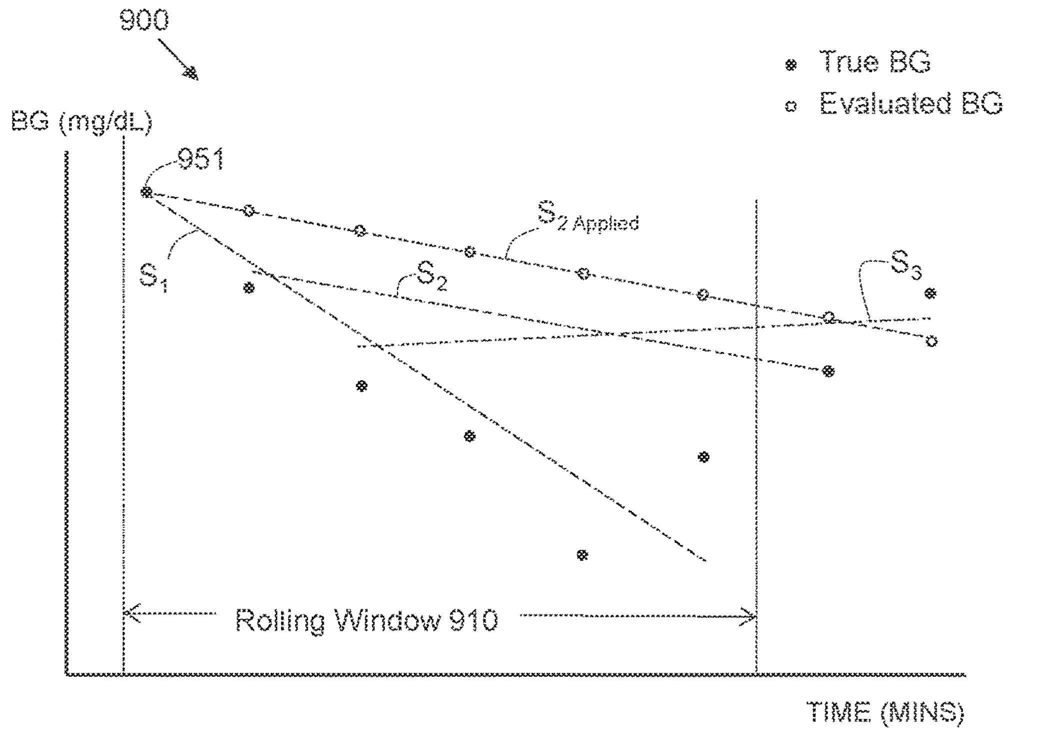
FIG. 9A is another graph illustrating a use case for determining a trend in blood glucose measurements over a given timeframe, according to some example embodiment.
Figure 9B:
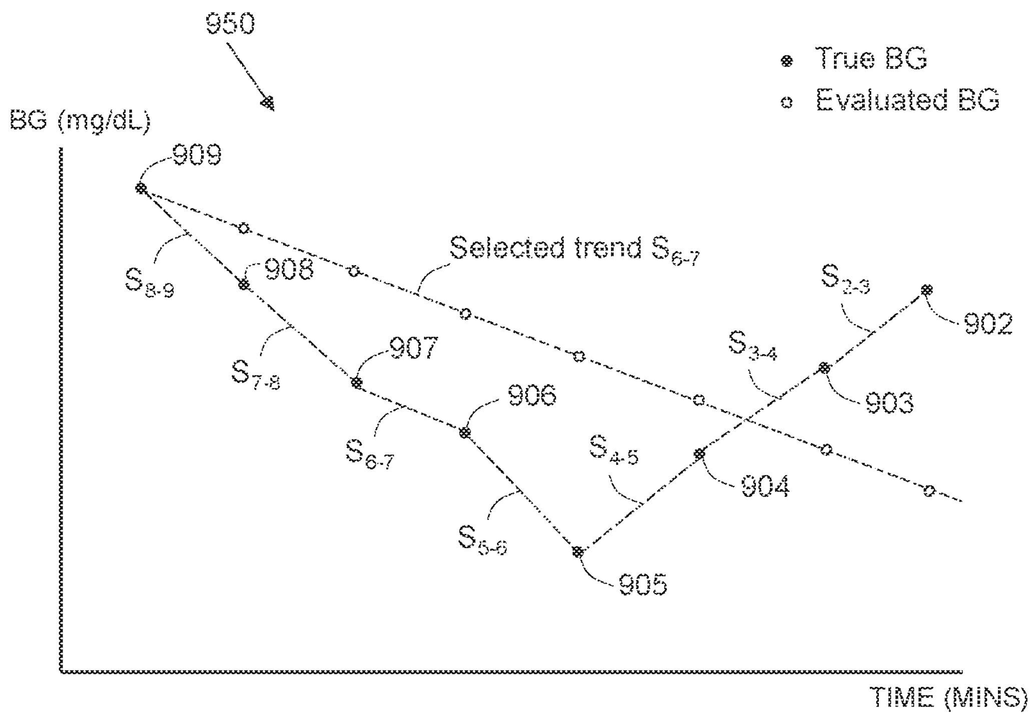
FIG. 9B is another graph illustrating a use case for determining a trend in blood glucose measurements over a given timeframe, according to some example embodiment.
Figure 10:
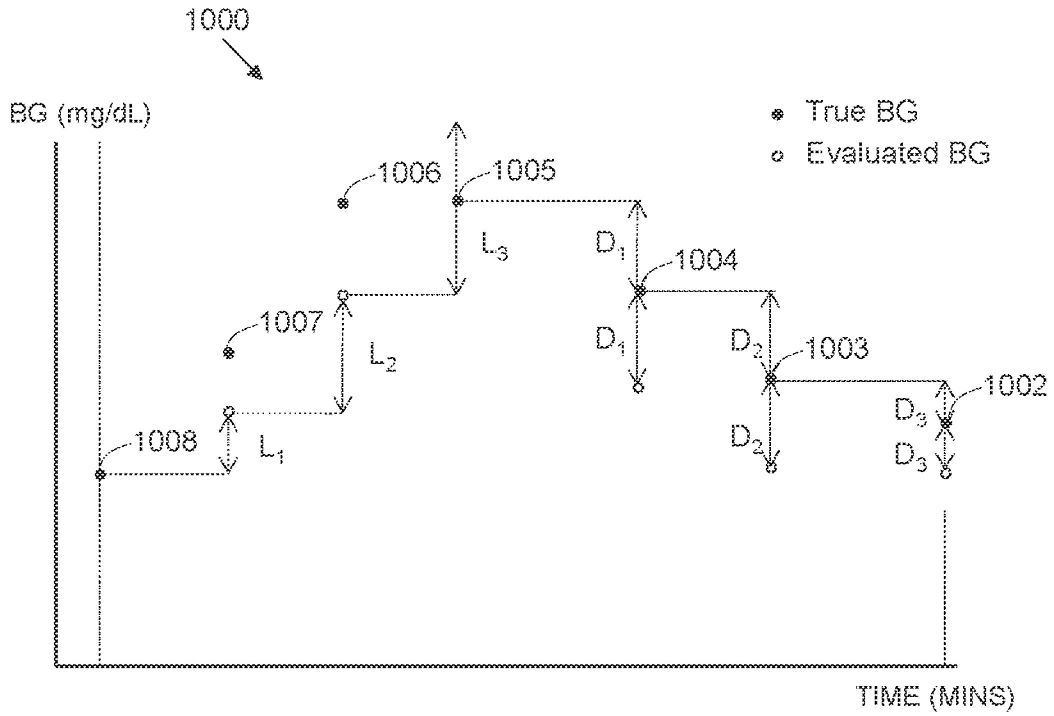
FIG. 10 is another graph illustrating another use case for determining a trend in blood glucose measurements over a given timeframe, according to some example embodiment.

Description regarding ways in which blood glucose measurements may be evaluated, for example, according to block 722 in FIG. 7 is continued below in connection with FIGS. 8-10. Each of these may also be considered methods of implementing a safety factor that allows for biasing toward less insulin delivery in the context of any unknowns that may affect blood glucose values. Another way to determine such a slope for drift compensation is described in connection with FIG. 8, which illustrates a use case where a drift slope is to be determined for a plurality of true or evaluated blood glucose measurements in a timeframe 800. In some embodiments, timeframe 800 may comprise a portion of fasting period 104 of FIG. 1. In some embodiments, a predetermined timeframe 810 (e.g., occurring $T_1$ or more time before $T_0$ reference and $T_2$ or less time before $T_0$, where $T_2>T_1$) prior to a reference (e.g., most recent or last) blood glucose measurement 802 is established, for example, between $T_1$ to $T_2$ is 15 to 30 minutes or 30 to 60 minutes before reference measurement 802. A slope is determined for each straight line connecting one of the blood glucose values 803-806 within predetermined timeframe 810 with reference measurement 802, the largest slope is selected as representative of the drift over the timeframe 800, and an amount of downward adjustment is determined based on the selected slope and a length L of a prospective period during which the downward drift is to be extended (e.g., reference 802 reduced by an amount equal to the product thereof to evaluated value 801). Selecting the largest slope from glucose values a sufficient time before reference measurement 802 solves a problem of underestimating blood glucose drift and, thereby overestimating insulin requirements, by preemptively adjusting true glucose values downward based on the fastest indication of long-term decline in blood glucose during the predetermined timeframe to account for future drift.

In some embodiments, evaluating received blood glucose measurements comprises filtering the received blood glucose measurements as described in connection with FIG. 9A, which illustrates a use case where a drift slope is to be determined for a plurality of true or evaluated blood glucose measurements in a timeframe 900. In some embodiments, timeframe 900 may comprise a portion of fasting period 104 of FIG. 1. In some embodiments, a linear regression fit slope, e.g., $S_1$, is determined for all blood glucose measurements in a rolling window 910 of a predetermined interval (e.g., a 60-minute window from a first blood glucose measurement to a last blood glucose measurement in the window). Rolling window 910 is advanced by one or more blood glucose measurements and the linear regression fit slope, e.g., $S_2$, $S_3$, is redetermined for all blood glucose measurements in the advanced rolling window 910. Accordingly, for each blood glucose value rolling window 910 advances, one prior blood glucose value used in the prior regression fit will fall outside the back of the window and one next blood glucose value not yet used in the prior regression fit will enter the front of the window. In some embodiments, for each of those slopes (e.g., $S_1$, $S_2$, $S_3$) a rolling average may be determined by averaging the value of each slope and a predetermined number of prior, or immediately adjacent, slopes. This serves the function of smoothing out smaller variations in how quickly the slopes change (e.g., reduces volatility of the change). Then a median value of the initial slopes (e.g., $S_1$, $S_2$, $S_3$), or of the rolling averages of each of those slopes, in timeframe 900 is selected (e.g., slope $S_2$) as representative of a trend for blood glucose values over timeframe 900, and the true blood glucose values (black dots) are filtered, or adjusted, to match the selected trend line extending from the first blood glucose value 951 of timeframe 900 (e.g., see white dots with black outline). Selecting the median slope (e.g., $S_2$) from among the regression fit slopes (e.g., $S_1$, $S_2$, $S_3$) of blood glucose values within rolling window 910, or in some cases from among the rolling averages of the regression fit slopes, ensures the value selected as indicative of the blood glucose trend over timeframe 900 is not driven by any extreme perturbation in either direction occurring within timeframe 900. This solves the problem of overdelivering insulin in the context of any unknown variables that may affect blood glucose values by limiting the rate of change of glucose variations based on a moderate representative slope of received blood glucose values within a timeframe of interest.

In some embodiments, evaluating received blood glucose measurements comprises filtering the received blood glucose measurements as described in connection with FIG. 9B, which illustrates a plurality of true and/or evaluated blood glucose measurements 903-909 from a recent timeframe 950 over which a blood glucose trend may be determined. A slope is determined for a line connecting each pair of neighboring glucose measurements, e.g., $S_{2\text{-}3}$, $S_{3\text{-}4}$, $S_{4\text{-}5}$, $S_{5\text{-}6}$, $S_{6\text{-}7}$, $S_{7\text{-}8}$, $S_{8\text{-}9}$. In some embodiments, a rolling average of those slopes may be determined by averaging the value of each slope and a predetermined number of prior, or immediately adjacent, slopes. This serves the function of smoothing out smaller variations in how quickly the glucose measurements change (e.g., reduces volatility of the change). Then a median value of the initial slopes, or of the rolling averaged slopes, in timeframe 950 is selected (e.g., slope $S_{6\text{-}7}$) as representative of a trend for blood glucose values over timeframe 950, and the true blood glucose values 902-909 (black dots) are filtered, or adjusted, to match the selected trend line extending from the first blood glucose value of timeframe 950 (e.g., see white dots with black outline). Selecting the median slope from among the individual slopes between adjacent true blood glucose values, or in some cases from among the rolling averages of the individual slopes between adjacent true blood glucose values glucose, may allow for representation of a trend in blood glucose over timeframe 950 that will better guard against over delivery of insulin while still effectively guiding the user's blood glucose toward a target range and then maintaining blood glucose near the target during fasting period 104. This solves the problem of overdelivering insulin in the context of any unknown variables that may affect blood glucose values by limiting the rate of change of glucose variations based on a moderate slope between adjacent received blood glucose values within a timeframe of interest.

In some embodiments, evaluating received blood glucose measurements comprises filtering the received blood glucose measurements as described in connection with FIG. 10, which illustrates a plurality of true or evaluated blood glucose measurements 1003-1008 from a recent timeframe 1000 over which a blood glucose trend may be determined. You will notice that blood glucose measurements 1008, 1007, 1006 follow an increasing trend that then flattens out with measurement 1005 and then begins to fall with measurements 1004, 1003, 1002. In some embodiments, evaluation of true received blood glucose measurements comprises imposing a progressively increasing limit (e.g., $L_1$, $L_2$ and $L_3$) on how much a next blood glucose value can increase compared to the previous value when the true blood glucose values are increasing (e.g., when the slope between adjacent true blood glucose values is positive, evaluation resulting in a deviation from true BG measurements shown for measurements 1006 and 1007) but amplifying a decrease (e.g., $D_1$, $D_2$, and $D_3$) between a blood glucose value and a next blood glucose value when the true blood glucose values are decreasing (e.g., when the slope between adjacent true blood glucose values is negative, evaluation resulting in a deviation from true BG measurements shown for measurements 1002, 1003 and 1004). For example, while each true blood glucose value is greater than or equal to the prior one within timeframe 1000, if a next true blood glucose value is more than a predetermined amount (e.g., $L_1$, $L_2$ and $L_3$) greater than a prior evaluated blood glucose value, the next evaluated blood glucose value is set only the predetermined amount greater than the prior evaluated blood glucose value, the predetermined amount is increased and the evaluation is repeated for the next true blood glucose value. However, when the next true blood glucose value is less than the prior true blood glucose value, the next evaluated blood glucose value is set a multiple (e.g, any decimal value greater than one, 2× shown) of the difference (e.g., $D_1$, $D_2$, and $D_3$) between the next and prior true blood glucose values below the prior evaluated blood glucose value. This solves a problem of overdelivering insulin in the context of any unknown variables that may affect blood glucose values by allowing evaluated received blood glucose measurements to merge slowly with a rising CGM line that is rounding a taller and broader peak than would typically be smoothed by rolling averages of blood glucose measurements but to merge quickly with a falling CGM line, thereby allowing for representation of a trend in blood glucose over timeframe 1000 that will better bias against over delivery of insulin while still effectively guiding the user's blood glucose toward a target range and then maintaining blood glucose near the target during fasting period 104.

Example Method(s) of Controlling Insulin Delivery Using Starting/Ending Activities and/or for Coordinating Fasting Period Insulin Management with Another Therapy Modality During a Non-Fasting Period Discussion now turns to methods of controlling insulin delivery using starting and/or stopping activities indicative of a need, desire, or appropriateness to initiate and/or terminate automated delivery of insulin from an insulin delivery device, respectively. Such aspects may also, or alternatively be employed for coordinating fasting period 104 insulin management with another therapy modality during non-fasting period 102. Such aspects may solve a problem of accounting for insulin on board from non-fasting delivery modalities without any user interaction or input, and without any prior, or direct knowledge whatsoever of the amount of insulin actually administered to the user from such non-fasting delivery modalities.

Initiation of a fasting period insulin management protocol may be caused by a user carrying out, and a device detecting the carrying out of, one or more starting activities 140 as described herein. Such terminating may be caused by the user carrying out, and a device detecting the carrying out of, one or more ending activities 150 as described herein.

Referring to FIG. 11, a flow diagram 1100 shows an example embodiment of a method of managing insulin by a delivery device, for example, such as delivery device 230 of FIG. 2. Such a method may be carried out at and/or by a controller, such as controller 232 of delivery device 230 shown in FIG. 2, at and/or by delivery device 301 or mobile computing device 302 as shown in FIGS. 3 and/or 4, and/or remotely at and/or by a server, computing device, or the like, such computing device 500 shown in FIG. 5, instructions then being sent to the controller. In some embodiments, certain steps may be carried out by such an above-described controller of the delivery device and/or with some of the steps carried out remotely to the controller. Accordingly, in some embodiments, such methods may be carried out in cooperation with such an above-described controller with a user application provided on a user's mobile computing device, for example mobile computing device 301 of FIGS. 3 and 4, or on another computing device, for example computing device 500 of FIG. 5.

Block 1101 includes detecting a starting activity associated with the use of a fasting period delivery device. For example, delivery device 230 is attachable to a user's body for a duration of fasting period 104 within overall time period 100 (see, e.g., FIG. 1). Such a starting activity 140 may be any activity indicative of a need, desire, or appropriateness to initiate automated delivery of insulin from the insulin delivery device 230. Automated delivery may be initiated without explicit instructions from the user. For example, in some embodiments, such a starting activity 140 may be any activity that is not a direct action to automate delivery, for example pressing a power button, but is, instead, an activity that commonly occurs or would be expected to commonly occur before or substantially at the beginning of fasting period 104. In this way, such starting activities have a primary function other than initiating automated delivery of insulin from the insulin delivery device 230 such that those starting activities are used for their primary function and also, simultaneously reused to effectively and accurately indicate of a need, desire, or appropriateness to initiate automated delivery of insulin because the starting activities are also activities who's occurrence has a significantly higher correlation with the start of fasting period 104. This solves at least the problem of transition complexity for transient use by providing a simplified system that allows for ease of transition between two different diabetes management modalities.

By way of example and not limitation, removal of delivery device 230 from charger 231 has a primary function of discontinuing charging of delivery device 230, not initiating a fasting period 104. However, since device 230 is worn by the user during fasting period 104, discontinuation of charging, removal from charger 231, and/or detecting the physical acceleration of device 230 during such an action, has a significantly higher correlation with the start of a fasting period 104 and, so may be reused for a purpose different than its primary purpose and to indicate initiating a fasting period 104.

Similarly, insulin pen 210 or mobile device 220 coming into a predetermined distance (e.g., proximity) of device 230 has a primary function of physically moving insulin pen 210 or mobile device 220, not initiating a fasting period 104. However, since insulin pen 210 and/or mobile device 220 may be utilized during non-fasting period 102, or to fill an insulin reservoir of device 230 immediately before fasting period 104, such an action, has a significantly higher correlation with the start of a fasting period 104 and, so may be reused for a purpose different than its primary purpose and to indicate initiating a fasting period 104.

Similarly, insertion of the insulin reservoir or of a prefilled insulin cartridge into device 230 has a primary function of coupling the insulin reservoir or cartridge to device 230, not initiating a fasting period 104. However, the insulin reservoir and/or cartridge must be inserted into device 230 to be usable during fasting period 104, such an action, has a significantly higher correlation with the start of a fasting period 104 and, so may be reused for a purpose different than its primary purpose and to indicate initiating a fasting period 104.

Similarly, an activity level falling to levels indicative of rest has a primary function of the user resting, not initiating a fasting period 104. However, since fasting period 104 is the timeframe during which the user is expected to sleep, occurrence of the user's activity level falling to or near resting rates has a significantly higher correlation with the start of a fasting period 104 and, so may be reused for a purpose different than its primary purpose and to indicate initiating a fasting period 104. Several additional examples of starting activities 140, each having a primary function other than initiating automated delivery of insulin from the insulin delivery device 230 such that those starting activities are used for their primary function and also, simultaneously reused to effectively and accurately indicate of a need, desire, or appropriateness to initiate automated delivery of insulin because the starting activities are also activities who's occurrence has a significantly higher correlation with the start of fasting period 104.

In some embodiments, a combination of two or more starting activities are required for insulin delivery to initiated. In some embodiments, a confirmation is requested or required, responsive to one or a plurality of starting activities, on a user interface, or the like. In some embodiments, the initiation of insulin delivery is responsive to a series of starting activities following predetermined criteria.

In some embodiments, such starting activity 140 may comprise arrival of a pre-set time of the day and/or an activity level of the user indicative of a period of rest. Detection of such a starting activity 140 may include various different forms of detection of preparing the delivery device prior to a readiness to deliver insulin, for example detecting one or more physical activities carried out by the user in relation to the delivery device, and/or detecting physical changes of the delivery device.

Examples of such physical activities carried out by the user in relation to the delivery device (starting activities 140) may include one or more of: removing controller 232 of delivery device 230 from charger 231 (see, e.g., FIG. 2), the attachment of dispensing unit 233 to controller 232 or installation of a pre-filled insulin cartridge (e.g., reservoir 225), application of delivery device 230 to a user's body, removal of applicator 235 from controller 232, completion of a manual priming sequence, or sound and/or voice commands from the user to controller 232.

Examples of such physical changes of the delivery device (starting activity 140) may include one or more of: detecting a movement of controller 232 by an accelerometer in controller 232, a proximity or pairing of controller 232 to user computing device 220 (e.g., a smart phone) on which user application(s) 221, 222 is/are provided, detecting a proximity or pairing of smart pen 210 when filling dispensing unit 233, detecting a connection of dispensing unit 233 or cartridge (e.g., reservoir) 225 to controller 232, detecting a fill level of insulin reservoir 225 by controller 232 indicative of a sufficiently filled insulin reservoir for initiating the automated delivery of insulin, detecting a removal of applicator 235 from controller 232, detecting removal of controller 232 from base 233, detecting movement of plunger 226 in dispensing unit 233, detecting an auto-priming of delivery device 230. Any of these examples of detecting a starting activity 140 may serve a function of transforming one or more physical activities of the user and/or physical changes of the delivery device into one or more electrical signals and/or physical configurations of one or more electrical components indicative of a need, desire, or appropriateness for initiating automated delivery of insulin from the insulin delivery device.

Block 1102 includes initiating automated delivery of insulin from the delivery device. For example, initiating automated delivery in response to the detected activity may include priming delivery device 230 to be ready to deliver insulin. In some embodiments, initiating automated delivery may also include any step, process and/or procedure described in connection with the FIG. 7 for controlling the delivery of insulin from a fasting-time wear delivery device.

Block 1103 includes delivering insulin (in the form of correction bolus doses) in response to the received blood glucose measurements during the fasting period. Such delivery of correction bolus doses 130*a*-130*e* is accomplished while refraining from administering any background basal doses of insulin. For example, such delivering insulin (in the form of correction bolus doses 130*a*-130*e*) is carried out in response to the received blood glucose measurements during the fasting period and may include any step, process and/or procedure described in connection with the FIG. 7 for controlling the delivery of insulin from a fasting-time wear delivery device.

Block 1104 includes detecting an ending activity associated with ending the use of the insulin delivery device. For example, delivery device 230 and/or mobile device 220 may be configured to detect such an ending activity 150, which may be any activity indicative of a need, desire, or appropriateness to terminate automated delivery of insulin from the insulin delivery device 230. For example, in some embodiments, such an ending activity 150 may be any activity that is not a direct action to stop automate delivery, for example pressing a power button to turn delivery device 230 off, but is, instead, an activity that commonly occurs or would be expected to commonly occur substantially at the end of fasting period 104. In this way, such ending activities have a primary function other than initiating stopping automated delivery of insulin from the insulin delivery device 230 such that those ending activities are used for their primary function and also, simultaneously reused to effectively and accurately indicate of a need, desire, or appropriateness to terminate automated delivery of insulin because the ending activities are also activities who's occurrence has a significantly higher correlation with the end of fasting period 104. This solves at least the problem of transition complexity for transient use by providing a simplified system that allows for ease of transition between two different diabetes management modalities.

Such an ending activity may include: detection of the removal of the wearable insulin reservoir from device 230, detection of removal of device 230 from the body, completion of a predetermined time period of less than a defined time period (for example, 24, 12, 10, 8 or 6 hours), or a returning of the durable portion of delivery device 230 to charger 231.

By way of example and not limitation, removal of the insulin reservoir of delivery device 230 has a primary function of disconnecting the insulin reservoir from delivery device 230, for example, to fill the reservoir, not terminating a fasting period. However, since the insulin reservoir must be properly disposed within delivery device 230 in order for proper function, removal of the insulin reservoir has a significantly higher correlation with the end of a fasting period 104 and, so may be reused for a purpose different than its primary purpose and to indicate terminating of fasting period 104.

Similarly, reconnecting device 230 to charger 231 has a primary function of charging delivery device 230, not terminating a fasting period 104. However, since device 230 is worn by the user during fasting period 104, reconnecting it to charger 231 has a significantly higher correlation with the end of a fasting period 104 and, so may be reused for a purpose different than its primary purpose and to indicate a desire to terminate a fasting period 104.

Similarly, removal of delivery device 230 from the user's body has a primary function of decoupling device 230 from the user's body, not terminating a fasting period. However, since the delivery device 230 must be properly worn by the user for proper function, removal of delivery device 230 from the user has a significantly higher correlation with the end of a fasting period 104 and, so may be reused for a purpose different than its primary purpose and to indicate terminating of fasting period 104.

Similarly, an activity level rising significantly above resting levels has a primary function of the user being active, not terminating a fasting period 104. However, since fasting period 104 is the timeframe during which the user is expected to sleep, occurrence of the user's activity level rising significantly above resting levels has a significantly higher correlation with the end of a fasting period 104 and, so may be reused for a purpose different than its primary purpose and to indicate terminating a fasting period 104.

In some embodiments, a combination of two or more ending activities are required for insulin delivery to initiated. In some embodiments, a confirmation is requested or required, responsive to one or a plurality of ending activities, on a user interface, or the like. In some embodiments, the initiation of insulin delivery is responsive to a series of ending activities following predetermined criteria.

Any example of detecting an ending activity 150 may serve a function of transforming one or more physical activities of the user or physical changes of the delivery device into one or more electrical signals and/or physical configurations of one or more electrical components indicative of a need, desire, or appropriateness for initiating a fast-ending procedure and/or for the user's discontinued use of insulin delivery device 230.

Block 1105 includes coordinating a fast-ending procedure for the user. For example, in response to detection of such an ending activity 150, delivery device 230 and/or mobile device 220 may be configured to coordinate and/or perform a fast-ending procedure, such as described in connection with block 730 of FIG. 7. For example, it is possible that a user wakes up with elevated glucose because the delivery of correction doses 130*a*-130*e* were conservative, assuming the user would still sleep for several more hours. As previously described in connection with at least FIG. 7, the delivery algorithm(s) disclosed herein may have numerous safeguards to avoid overdelivering insulin during fasting period 104. Accordingly, once the user is awake, a final fast-ending bolus (e.g., dose 130*e* in some embodiments), which is not necessarily associated with a meal, may be required. Calculation of such a final fast-ending bolus may be determined as previously described in connection with FIG. 7. In some other embodiments, such a fast-ending bolus may be administered near or at the end of fasting period 104 in expectation of a meal being eaten after fasting period 104 has ended, as also described in connection with at least FIG. 14. In some embodiments, such a final fast-ending bolus may comprise the remaining insulin in delivery device 230. Where the remaining insulin is less than the calculated fast-ending bolus, the amount delivered by device 230 may be only part of the required fast-ending bolus and the coordination of block 1105 may also include coordinating administration of the remainder of the fast-ending bolus by the user utilizing the non-fasting insulin modality (e.g., MDI pen 210 of FIG. 2) as will be described in more detail in connection with at least FIG. 14.

Figure 12:
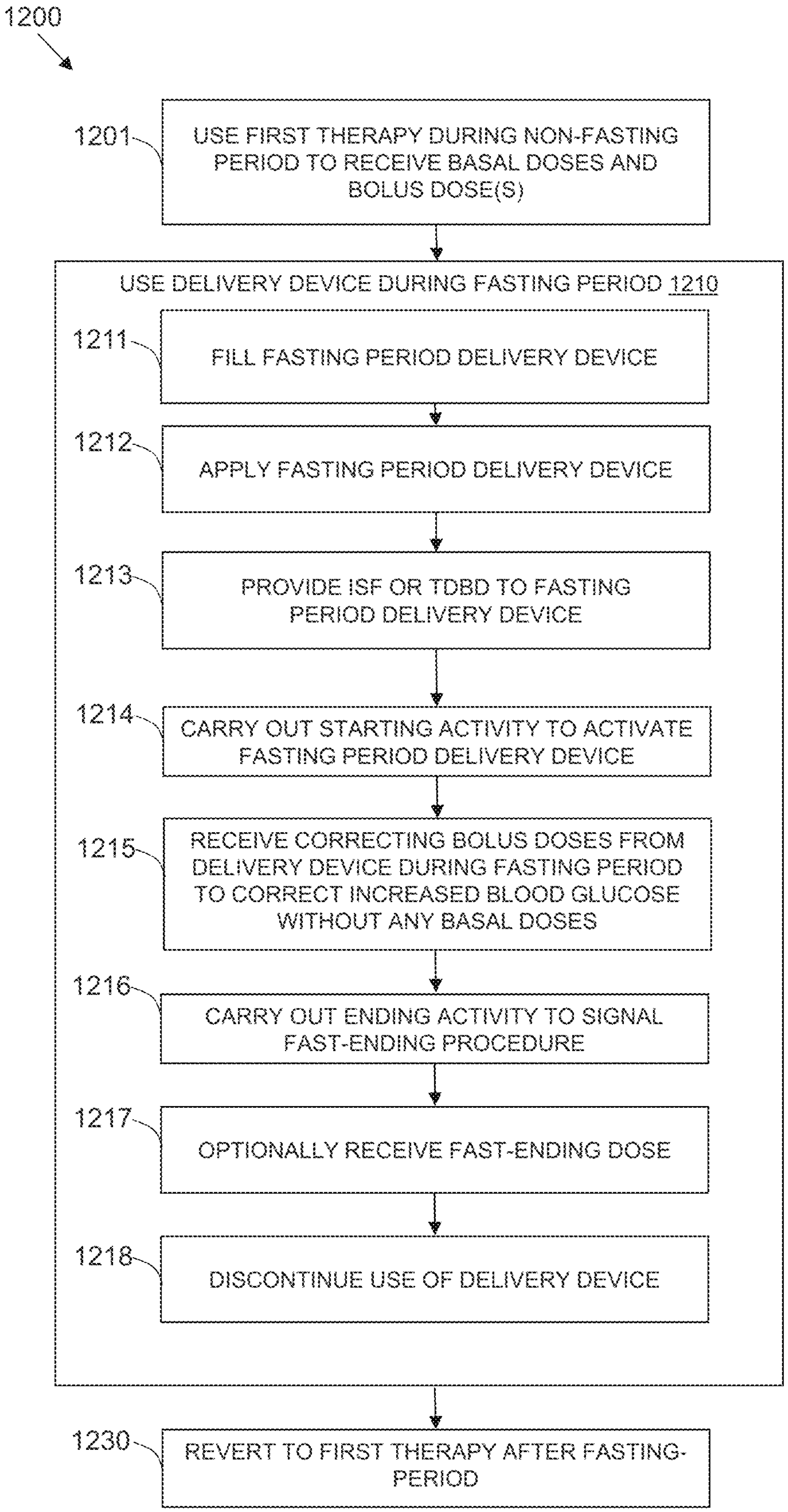
FIG. 12 is a flow diagram of methods of use of a device for controlling delivery of insulin and/or for coordinating such fasting period insulin management with another therapy modality utilized during a non-fasting period, according to some example embodiments.

Referring to FIG. 12, a flow diagram 1200 shows an example embodiment of a method of managing insulin by a user of a delivery device, for example, such as the delivery device 230 of FIG. 2.

Block 1201 includes a user using a first therapy during a non-fasting period within an overall time period to receive basal doses of insulin and bolus doses of insulin. For example, a user may use such a first therapy during non-fasting period 102 within overall time period 100 to receive basal dose(s) 110*a*-110*b* of insulin and bolus doses 120*a*-120*d* of insulin (see, e.g., FIG. 1). The first therapy, a non-fasting insulin management modality, may include any mode, method, device process, therapy, or the like that is used as an intervention in diabetes therapy, including but not limited to a pump delivery of insulin (other than fasting period delivery device 230), MDI pen or syringe injections of insulin, inhaled insulin, oral insulin, or any form of insulin management used when the user is awake. The non-fasting insulin management modality may also include diet and exercise where insulin is managed, at least some of the time, without medicinal intervention. In some embodiments, the non-fasting insulin management modality may also, or alternatively, include any oral medication for type 1 or type 2 diabetes, for example and not limitation, GLP-1 and metformin.

Block 1210 includes the user using a fasting insulin delivery device during a fasting period within the overall time period as an adjunctive therapy to the first therapy. For example, the user may use fasting insulin delivery device 230 during fasting period 104 within overall time period 100

(see, e.g., FIG. 1) as an adjunctive therapy to MDI therapy, for example utilizing pen 210 shown in FIG. 2. As described anywhere in this disclosure, fasting insulin delivery device 230 may be an automatic insulin delivery device, attachable to a user's body for the duration of fasting period 104 that delivers correction bolus doses 130*a*-130*e* in response to received blood glucose measurements and refrains from administering any background basal doses of insulin, (as well as meal bolus doses in some embodiments). The user is not required to interact with delivery device 230 for correction of bolus insulin during fasting period 104, when the user is typically asleep. In some embodiments, the time period of intended fasting (e.g., the extent of fasting period 104) may be from up to about 2 hours before the user goes to sleep and until about 2 hours after waking.

While not illustrated in flowchart 1200, prior to block 1211, a user may remove delivery device 230 from charger 231. As delivery device 230 is only utilized by the user during fasting periods 104, it can be charged during non-fasting periods 102, for example, during the daytime. Moreover, as described elsewhere in this disclosure, removing delivery device 230 from charger 231 may be an example of a starting activity 140 indicative of a need, desire, or appropriateness for initiating automated delivery of insulin from the insulin delivery device 230.

Block 1211 includes the user filling the fasting insulin delivery device with insulin before use during the fasting period. For example, the user may fill delivery device 230 with insulin before use during fasting period 104 using the insulin available from the first therapy (e.g., from pen 210 of FIG. 2), for example as described in more detail in connection with FIGS. 13A-13L below. This provides a continuity of use of insulin from the first therapy into the second therapy that enables a total insulin use to be monitored as the insulin is coming from a single source. Alternatively, the user may fill delivery device 230 from a separate source, particularly if a different type of insulin is used in delivery device 230 compared to the first therapy. Filling may be carried out by inserting a pre-filled cartridge or a cartridge that is partially-filled from a previous use session. Alternatively, or in addition, filling may be carried out from a vial, syringe, pen or other insulin dosing apparatus.

Block 1212 includes the user applying the fasting period delivery device to their body. For example, the user may apply delivery device 230 to their body for use during fasting period 104, as described anywhere in this disclosure, for example, as described in more detail in connection with FIGS. 13A-13I below. In some embodiments, application of delivery device 230 may occur immediately after a last meal of non-fasting period 102 or within a few hours thereof. For example, the user may apply the delivery device before bedtime or after finishing their daily meals. The user may determine when to apply and remove delivery device 230 based on personal day and night cycles. Accordingly, the duration and time in the day of fasting period 104 may vary from use to use for the same user. In some embodiments, the user may be assisted in the use and application of delivery device 230 by user application 222 provided on the user's mobile computing device 220, for example, a smart phone (see, e.g., FIG. 2). For example, user application 222 may be configured to provide coordination between use of delivery device 230 during fasting period 104 and the first therapy (e.g., MDIs utilizing pen 210) during non-fasting period 102 as described anywhere in this disclosure including but not limited to FIG. 16. In some such embodiments, user application 222 may also be configured to recommend a time for application of delivery device 230 and/or a time for removal of delivery device 230.

Block 1213 includes the user providing at least one of ISF and TDBD to the fasting period delivery device. For example, the user may provide at least one of their ISF and TDBD directly to fasting period delivery device 230, or indirectly through a user interface of user application 220 on mobile computing device 220. This ISF and/or TDBD information may be utilized to set up delivery device 230, for example as previously described in connection with FIG. 7. This information may be a once-off requirement when a user first uses delivery device 230. In some embodiments, this information may be provided via the first therapy (e.g., from pen 210 of FIG. 2) with or without user involvement. For example, smart insulin pen 210 may provide this information directly to delivery device 230 or via a user application, e.g., user application(s) 221 and/or 222. In some embodiments, a method according to flowchart 1200 may not allow the user to provide to delivery device 230 information relating to one or more of the following parameters: an amount of insulin to be delivered; a duration of insulin action; a target blood glucose; a basal rate of insulin administration (i.e., a rate of administration of, specifically, basal, background and/or baseline insulin required to maintain blood glucose at a target not including meal bolus doses); an IOB; and an insulin to carbohydrate ratio. In some embodiments, a method according to flowchart 1200 may not allow the user to provide such parameters by not including any input means for the parameters to delivery device 230 and/or user application 221 and/or 222.

Block 1214 includes the user carrying out a starting activity associated with preparation of use of the insulin delivery device used during the fasting period. For example, the user may carry out any starting activity 140 that is associated with preparation and/or use of delivery device 230 during fasting period 104 as described anywhere in this disclosure. For example, and not limitation, such starting activities 140 may include arrival of a pre-set time of the day and/or an activity level of the user indicative of a period of rest, one or more physical activities carried out by the user in relation to the delivery device, and/or detecting physical changes of the delivery device as described anywhere in this disclosure.

Block 1215 includes the user receiving correction doses of insulin from the fasting period delivery device during a fasting period to correct increased blood glucose. Such correction of increased blood glucose is accomplished without administration of any basal doses of insulin during fasting period 104. For example, the user may receive correction doses 130*a*-130*e* from delivery device 230 during fasting period 104 to correct increased blood glucose as described anywhere in this disclosure, especially FIG. 7.

In some embodiments of flowchart 1200, block 1216 includes the user carrying out an ending activity to signal a fast-ending procedure. For example, the user may carry out any ending activity 150 as described anywhere in this disclosure. For example, and not limitation, such ending activities 150 may include indication from the user of a desire to transition out of fasting period, removal of any portion of delivery device 230 from the user's body, completion of a predetermined time period of less than a defined time period (for example, 24, 12, 10, 8 or 6 hours) within fasting period 104, or a returning of the durable portion of delivery device 230 to charger 231. as described anywhere in this disclosure.

In some embodiments of flowchart 1200, block 1217 includes optionally receiving a fast-ending dose. For example, once it is determined that fasting period 104 is to be transitioned out of, the user may receive any fast-ending bolus, for example, from delivery device 230 as described anywhere in this disclosure. For example, and not limitation, a user may wake with elevated glucose because the delivery of correction doses was conservative, operating under an assumption that the user would still sleep for several more hours, in which case, a final fast-ending correction bolus not associated with a meal (or a portion of such a correction dose comprising the remaining insulin in the delivery device) may be received by the user from delivery device 230. Alternatively, the user may receive such a final fast-ending correction bolus as a hybrid corrective and meal bolus, administered at or near the end of the fasting period 104 to both correct waking elevated glucose and, further, in expectation of a meal being eaten during the subsequent non-fasting period 102 after the fasting period 104 has ended.

Block 1218 includes discontinuing use of the delivery device. For example, once the user is no longer in fasting period 104, use of delivery device 230 is discontinued until the next fasting period 104. In some embodiments, discontinuing use may comprise removing delivery device 230 from the user's body at the end of fasting period 104. In some embodiments, discontinuing use merely means discontinuing delivery of insulin via delivery device 230. In some embodiments, the user may remove delivery device 230 before or after an initial fast-ending meal following fasting period 104, e.g., after or within about 2 hours of waking up. In some embodiments, the user may remove delivery device 230 after determining an amount of additional insulin needed to cover the fast-breaking meal as described further in relation to FIG. 13. Though not illustrated in flowchart 1200, the user may return delivery device 230 to charger 231.

Block 1230 includes the user reverting to the first therapy after the fasting period. For example, the user may revert to their preferred first therapy method during non-fasting period 102. According to the above, it is not essential that the delivery device is removed before the first therapy is recommenced. The reservoir 225 of delivery device 230 may only hold an amount of insulin needed for fasting period 104 and therefore may be almost or completely empty as fasting period 104 expires. Moreover, as stated previously, any residual amount in reservoir 225 may be used for a fast-ending bolus or portion thereof.

In some embodiments, the user does not enter and cannot modify any of the following parameters or information into delivery device 230 and/or mobile device 220: an amount of insulin to be delivered; a duration of insulin action; a target blood glucose; a rate of basal insulin administration; an IOB; and an insulin to carbohydrate ratio. Accordingly, in such embodiments, the amount of insulin to be delivered by delivery device 230 cannot be modified by the user other than by removing delivery device 230 from their body. To remove the opportunity for significant DIA error due to incorrect estimation, in such embodiments, a fixed setting is used. In some embodiments, the target glucose is also fixed and cannot be modified by the user and may have an additional safety factor. Since no meals bolus doses are delivered during fasting period 104, except embodiments where an optional fast-ending bolus is administered to specifically account for an upcoming meal to be eaten at the beginning of the next non-fasting period 102, insulin to carbohydrate ratio is not needed from the user.

Figure 13A:
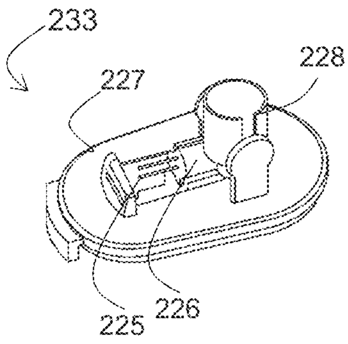
FIGS. 13A to 13L are a series of schematic diagrams illustrating an example embodiment of aspects of a delivery device, according to some example embodiments.

Referring to FIGS. 13A to 13L, an example embodiment of delivery device 230, shown in a series of illustrations of a user filling and applying delivery device 203 as described anywhere in this disclosure. The packaging arrangement (kit) 250 of delivery device 230 and associated apparatus is illustrated in FIG. 2, where it was shown that a durable portion of delivery device 230, in the form of controller 232, is provided with multiple sealed packages 251, for example, blister-packs, each containing a disposable dispensing unit 233. As shown in FIG. 13A, dispensing units 233 each include a reservoir 225 and a plunger 226 supported on a base 227 with plunger 226 provided for controlled delivery of insulin from reservoir 225 to the user via a cannula (not shown). Dispensing units 233 are provided with a coupler 228 attached and dispensing units 233 may be provided without any insulin in their reservoirs 225 for filling from an MDI therapy pen 210 or syringe by using coupler 228 to properly position pen 210 or the syringe. Packaging arrangement 250 also includes applicator 235 and charger 231 with charging cable 235 (see, e.g., FIG. 2). Alternative embodiments may be configured to received pre-filled cartridges in place of reservoir 225.

Figure 13B:
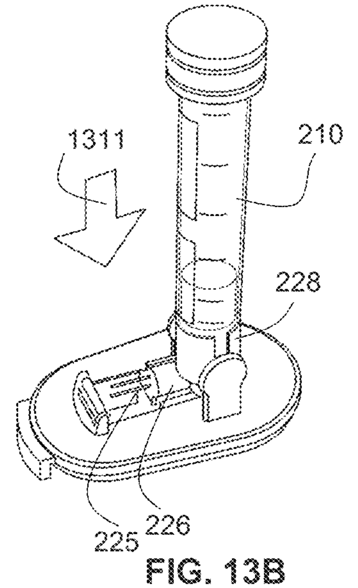
Figure 13C:
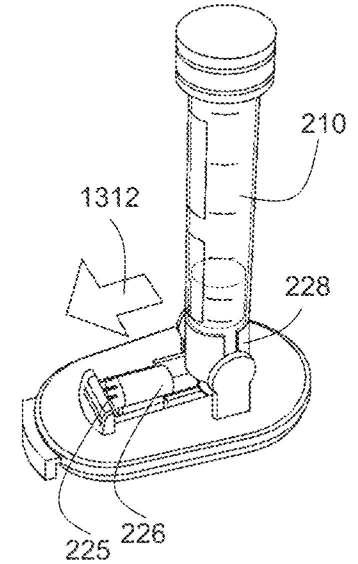
Figure 13D:
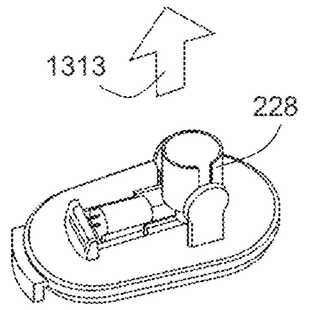
Figure 13E:
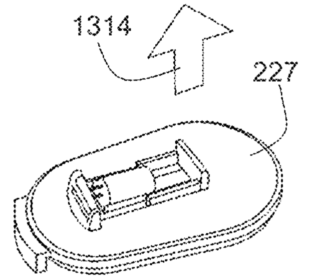
Figure 13F:
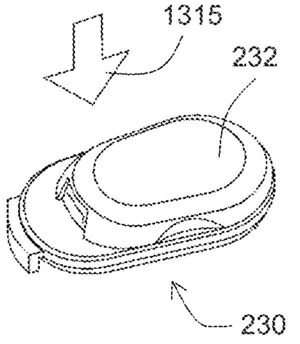

Dispensing unit 233 is provided in sealed package 251, which is opened by the user to extract dispensing unit 233 supported on base 227 as shown in FIG. 13A. Dispensing unit 233 includes coupler 228 for attachment 1311 of insulin pen 210 as shown in FIG. 13B to fill reservoir 225. During filling of reservoir 225, plunger 226 is pushed backwards 1312 as shown in FIG. 13C. Plunger 226 may be colored to allow the user to see the movement of plunger 226. Insulin pen 210 is removed 1313 as shown in FIG. 13D either together with, or followed by, the removal 1314 of coupler 228 as shown in FIG. 13E, leaving dispensing unit 233. Controller 232 is attached 1315 to dispensing unit 233 to form delivery device 230 as shown in FIG. 13F.

Figure 13G:
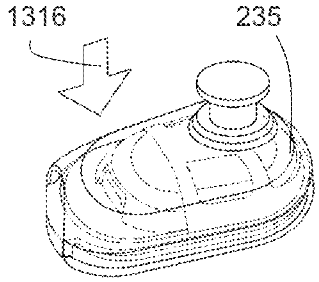
Figure 13H:
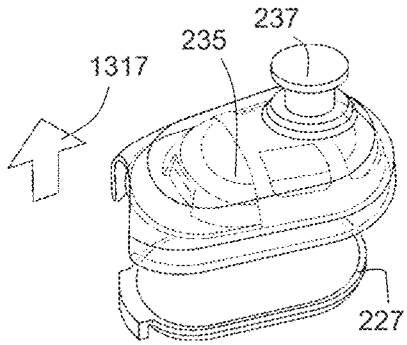
Figure 13I:
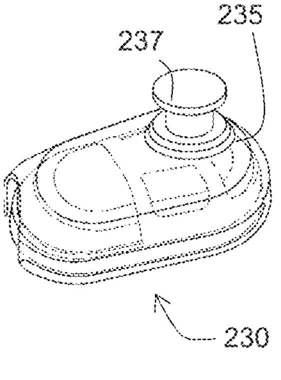
Figure 13J:
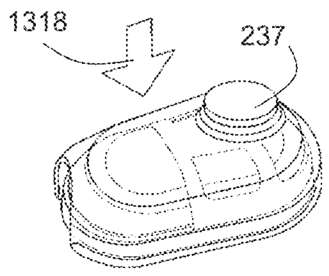
Figure 13K:
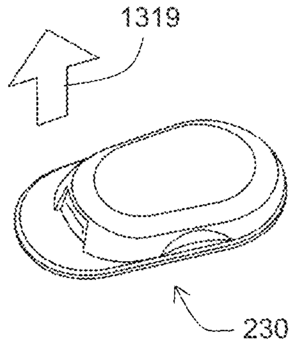
Figure 13L:
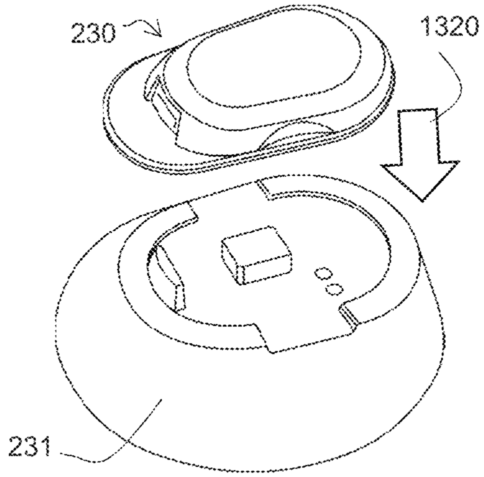

Push applicator 235 is configured to attach 1316 to an upper portion of delivery device 230 as shown in FIG. 13G to allow delivery device 230 to be removed 1317 from base 227 as shown in FIG. 13H. Delivery device 230, held within applicator 235, is positioned on the user's body as shown in FIG. 13I. The applicator's push button 237 is pushed down 1318 as shown in FIG. 13J to exert a push force by the user via applicator 235 to adhere delivery device 230 to the user's body by an adhesive attachment. Applicator 235 is removed 1319 from delivery device 230 as shown in FIG. 13K and delivery device 230 is then ready to deliver the correction doses during fasting period 104 (see, e.g., FIG. 1). At the end of fasting period 104, delivery device 230 is removed from the user's body as shown in FIG. 13L and returned 1320 to power charger 231.

Applicator 235 may surround and hold an upper portion of delivery device 230 such delivery device 230 can be removed from base 227 and positioned on the user's body with a single hand. Push button 237 of applicator 235 may cause a suitable force to detach delivery device 230 from applicator 235 and push it onto the user's skin such that an adhesive surface on the underside of delivery device 230 attaches to the user's skin and the cannula on the underside of delivery device 230 pierces the user's skin ready for delivery of insulin.

In some embodiments, reservoir 225 of delivery device 230 may be filled before wear and the user does not refill it during the wearing time. Accordingly, delivery algorithms described herein do not require reservoir 225 to be filled during use. In some embodiments, the delivery of insulin is totally automated except by removal of the wearable device, with no user control. Accordingly, in some such embodiments, alerts or alarms are not required with the delivery device.

Figure 14:
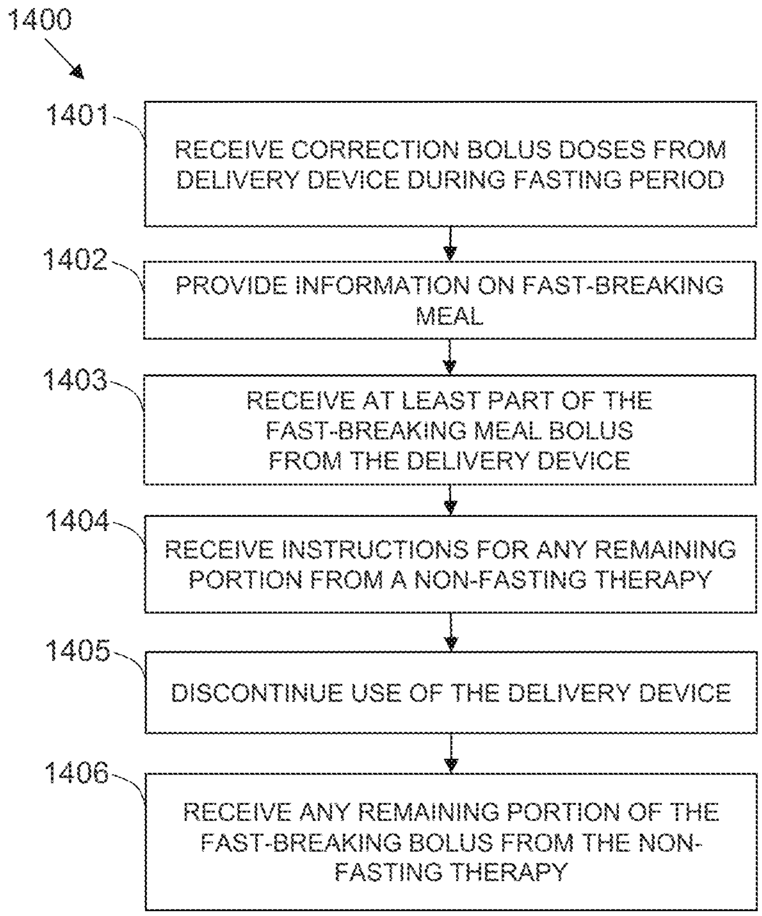
FIG. 14 is a flow diagram of methods of use of a device for controlling delivery of insulin and/or for coordinating such fasting period insulin management with another therapy modality utilized during a non-fasting period, according to some example embodiments.

FIG. 14 illustrates a flowchart 1400 related to a fast-ending or fast-breaking procedure in which at least part of a fast-ending meal bolus may be provided from the remaining insulin in the reservoir of delivery device 230 in expectation of a meal being eaten in the upcoming non-fasting period 102.

Block 1401 includes the user receiving correction bolus doses from the fasting period delivery device during the fasting period. For example, the user may receive correction doses 140*a*-130*d* from delivery device 230 during fasting period 104 as shown in FIG. 1. In some embodiments, block 1401 may be substantially the same activity as described in connection with block 1215 of FIG. 12.

Block 1402 includes the user providing information relating to a fast-breaking meal that requires a meal bolus. For example, a user eating some amount of carbohydrates typically requires insulin administration to avoid resulting elevated glucose. At the end of fasting period 104, the user may provide information relating to a fast-breaking meal, for example to delivery device 230 or mobile device 220 through user input, through wirelessly connected insulin pen 210, and/or from a user software application such as application(s) 221, 222 (see, e.g., FIG. 2). In some embodiments, the information may include meal information in the form of carbohydrates.

In some embodiments, as previously described in connection with the fast ending procedure of block 730 in FIG. 7, device 230, mobile device 220, insulin pen 210 and/or another remotely located computer 500 (see, e.g., FIG. 2) may be configured to determine an amount of bolus insulin estimated to account for rises in blood glucose that will be caused by a meal matching the provided meal information, as well as any remaining elevation of blood glucose at the end of fasting period 104. In some embodiments, when the user ends fasting period 104 in a target blood glucose range, device 230, mobile device 220, insulin pen 210 and/or another remotely located computer 500 drives a delivery recommendation (e.g., a recommendation to deliver the first meal bolus in non-fasting period 102 immediately following fasting period 104 (see, e.g., FIG. 1). When the user ends the fasting period 104 with an elevated glucose, the recommendation may include additional units of insulin to neutralize the elevation.

Block 1403 includes the user receiving at least part of the fast-breaking meal bolus from the delivery device. For example, in some embodiments, the user may receive an amount of insulin from delivery device 230 based on an amount of insulin available in delivery device 230 at the end of fasting period 104. If delivery device 230 does not include the full fast-breaking meal bolus, the dose may be split into a first portion and second portion, which together add up to the total calculated recommended insulin bolus amount.

Figure 15:
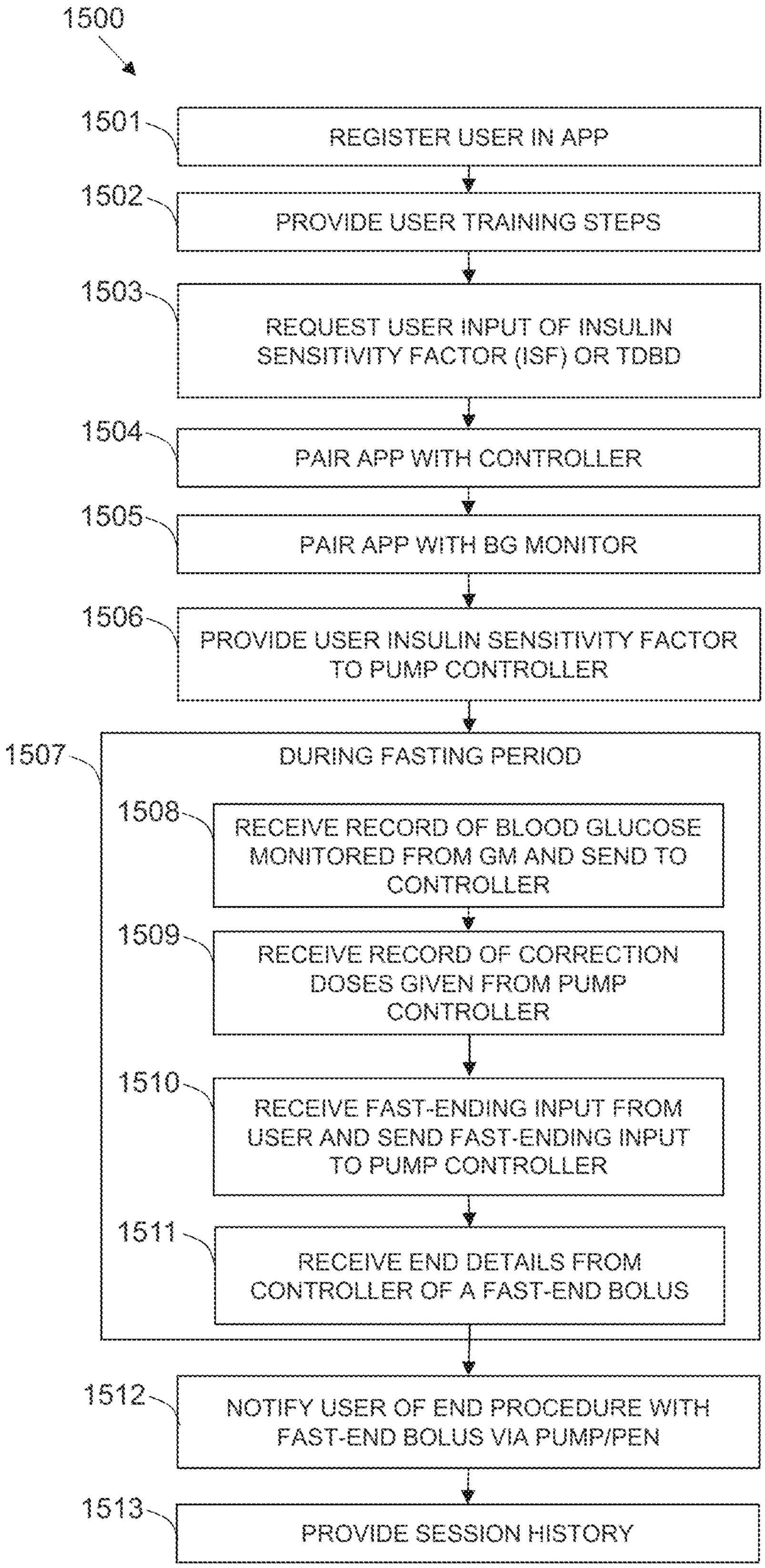
FIG. 15 is a flow diagram of example methods provided by a computer application for interacting with a delivery device for controlling delivery of insulin during a fasting period and/or for coordinating such fasting period insulin management with another therapy modality utilized during a non-fasting period, according to some example embodiments, according to some example embodiments.
Figure 16:
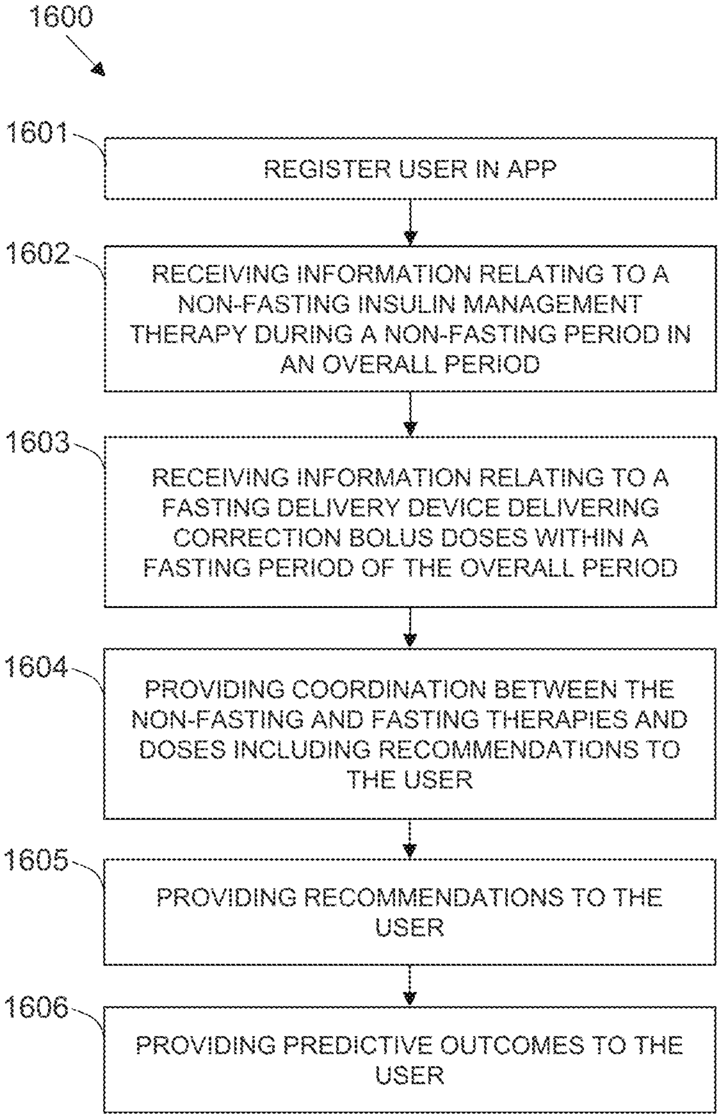
FIG. 16 is another flow diagram of example methods provided by a computer application for interacting with a delivery device for controlling delivery of insulin during a fasting period and/or for coordinating such fasting period insulin management with another therapy modality utilized during a non-fasting period, according to some example embodiments, according to some example embodiments.

The first portion may be determined based on the amount of insulin remaining in reservoir 225 of delivery device 230, which may be known, measured, and automatically dispensed by delivery device 230 and then confirmation provided, for example, from user application 222 as described further in relation to FIG. 15 or 16. Alternatively, the user may press a button on mobile app 222 or on delivery device 230 to receive remaining insulin up to a maximum required for the recommended meal bolus amount. For example, if 4 units of insulin are left in the reservoir of the delivery device, this is not wasted when removing the patch, rather the remainder can first be delivered to the user.

The second portion, being the difference between the recommended meal bolus and the amount of insulin remaining in reservoir 225 of delivery device 230, may be provided by another form of insulin therapy modality at the beginning of the immediately following non-fasting period 102 (e.g., insulin pen 210 of FIG. 2). For example, if the recommended meal bolus is 8 units, 4 units may be provided from a remainder in the reservoir, and 4 units may be delivered by insulin pen 210.

Accordingly, block 1404 includes receiving instructions to administer the second portion via the non-fasting therapy. Alternatively, in some embodiments, such instructions may be automatically sent to the therapy device, e.g., smart insulin pen 210. Instructions to deliver the second portion with the first therapy may be delivered to the user via a connected device, such as insulin pen 210 or user application 222 of mobile device 220. IOB may also be sent to user application 222 or to smart insulin pen 210 for continuity of insulin delivery. Such coordination and/or delivery of instructions to the user may be carried out via the user application described further in relation to FIG. 15 or via a separate therapy coordination user application described further in relation to FIG. 16.

Block 1405 includes the user discontinuing use of the delivery device. For example, once any final fast-ending dose is received by the user from delivery device 230, use of delivery device 230 is discontinued, as the fasting period 104 has ended. In some embodiments, the user may remove delivery device 230 if not already removed.

Block 1406 includes the user receiving any second (remaining) portion from the non-fasting therapy. For example, the user may receive the second portion of the fast-ending meal bolus dose from the first therapy, e.g., insulin pen 210 of FIG. 2. Since use of delivery device 230 has been discontinued and fasting period 104 has ended, the user receives this second portion via pen 210 at the beginning of the immediately following non-fasting period 102 (see, e.g., FIG. 1).

Referring to FIG. 15, a flow diagram 1500 shows an example embodiment of a method for managing delivery of insulin during a fasting period 1004 from delivery device 230 worn for fasting period 1004 (see, e.g., FIGS. 1-2). The method is carried out by a computer software application provided at, e.g., mobile computing device 220, such as a smart phone or tablet (e.g., mobile device 302 in FIG. 4). The computer software application may be an application for managing fasting period delivery device 230 and the function thereof as described anywhere in this disclosure.

Block 1501 includes registering a user of the application. For example, and not limitation, registration component 411 of mobile computing device 302 (FIG. 4) may be configured to perform one or more processes or procedures involved in registering a user.

Block 1502 includes providing training steps instructing the user how to use a delivery device including filling from an insulin pen. For example, and not limitation, user training component 412 of mobile computing device 302 (FIG. 4) may be configured to provide training steps to user interface 450 (e.g., visual display, audio speaker(s)) and, so, to the user, instructing the user how to use delivery device 230 including filling from insulin pen 210, for example as previously described in connection with at least FIGS. 13A-13L. This may be carried out when a user first uses delivery device 230.

Block 1503 includes requesting user input of an insulin sensitivity factor or total daily basal dose information. For example, and not limitation, basal insulin or ISF input component 413 of mobile computing device 302 (FIG. 4) may be configured to request and receive user input of an insulin sensitivity factor or total daily basal dose information from the user. Such requesting may include requesting a type of long-acting insulin used by the user and how many units of long-acting insulin are usually taken per 24 hours. The user may update this information if this changes. This TDBD information may be used to set an ISF for the user as described anywhere in this disclosure. Where ISF is requested and provided, calculation of ISF may not be needed.

To set up delivery device 230 for fasting period 104, block 1504 may include pairing the mobile communication device running the application with a controller of the delivery device. For example, and not limitation, controller pairing component 414 of mobile computing device 302 (FIG. 4) may be configured to pair mobile device 302 running the application with controller 232 of delivery device 230. The pairing may be via a near field communication technology, for example, using Bluetooth™. The application may include instructions for pairing.

Block 1505 includes pairing the mobile communication device running the application with a blood glucose monitor worn by the user. For example, and not limitation, glucose monitor pairing component 415 of mobile computing device 302 (FIG. 4) may be configured to pair mobile device 302 running the application with blood glucose monitor 205 worn by the user. The pairing may be via a near field communication technology, for example, using Bluetooth™. The application may include instructions for pairing.

Block 1506 includes providing the user's ISF to the delivery algorithm of the controller of the delivery device for use in the calculation of the correction doses. For example, and not limitation, ISF providing component 416 of mobile computing device 302 (FIG. 4) may be configured to provide the user's ISF (either as input by the user, calculated based on TDBD, and/or adjusted by a safety factor as described anywhere in this disclosure) to the delivery algorithm of controller 232 of delivery device 230 for use in the calculation of correction doses 130*a*-130*e*, for example as described in connection with at least FIG. 7.

During fasting period 104 (e.g., encompassing block 1507), block 1508 includes receiving a record of blood glucose measurements as monitored from the glucose monitor and sending them to the controller for calculation of correction bolus doses. For example, and not limitation, blood glucose providing component 417 of mobile computing device 302 (FIG. 4) may be configured to receive a record of blood glucose measurements as monitored from glucose monitor 205 and send them to controller 232 for calculation of correction bolus doses 130*a*-130*e*. Alternatively, these may be sent directly from glucose monitor 205 to controller 232. In another alterative, as previously discussed, glucose monitor 205 may be integrated into delivery device 230 and provided within controller 232. Evaluation of the blood glucose measurements (e.g., filtering and/or projecting as described anywhere in this disclosure) may be carried out at the application in order to send evaluated blood glucose values to controller 232 for use in the delivery algorithm, for example as described in connection with at least FIG. 7.

During fasting period 104 (e.g., encompassing block 1507) block 1509 includes receiving a record of correction bolus doses delivered by the delivery device. For example, and not limitation, dose receiving component 418 of mobile computing device 302 (FIG. 4) may be configured to receive a record of correction bolus doses 130*a*-130*e* delivered by delivery device 230.

Flowchart 1500 may also include a fast-ending or fast-breaking procedure as described anywhere in this disclosure. Block 1510 includes receiving a fast-ending input from the user and sending this input to the pump controller. For example, and not limitation, fast-ending component 419 of mobile computing device 302 (FIG. 4) may be configured to receive a fast-ending input from the user, for example, information on a fast-breaking meal expected to be eaten at the beginning of an upcoming non-fasting period 102 as described in connection with at least FIG. 14, and sending this input to pump controller 232.

Block 1511 includes receiving details from the controller of a fast-ending bolus dose. For example, and not limitation, fast-ending component 419 of mobile computing device 302 (FIG. 4) may be configured to receive details of a fast-ending bolus dose (e.g., in some cases 130*e* in FIG. 1) from controller 232.

Block 1512 includes notifying the user of the end procedure with instructions to supplement the delivery device fast-ending dose with their insulin pen. For example, and not limitation, fast-ending component 419 of mobile computing device 302 (FIG. 4) may be configured to notify the user of the end procedure with instructions to supplement the fast-ending dose from delivery device 230 with a remaining portion of the dose to be delivered from insulin pen 210, for example as described anywhere in this disclosure.

Block 1513 includes providing a session history including a display of correction doses given by the delivery device together with the blood glucose measurements and including additional statistics for user information. For example, and not limitation, session history component 420 of mobile computing device 302 (FIG. 4) may be configured to provide a session history including a display of correction doses given by delivery device 230 together with the blood glucose measurements and including additional statistics for user information, for example as described anywhere in this disclosure. Session histories for previous sessions (e.g., previous fasting periods 104) may also be provided.

Referring to FIG. 16, a flow diagram 1600 shows an example embodiment of a method for managing delivery of insulin during a fasting period 104 from delivery device 230 worn for fasting period 1004 (see, e.g., FIGS. 1-2). The method is carried out by a computer software application provided at, e.g., mobile computing device 220, such as a smart phone or tablet (e.g., mobile device 302 in FIG. 4). The computer software application may be a coordination application for coordination of the use of fasting delivery device 230 with a non-fasting insulin therapy, such as an MDI therapy using smart insulin pen 210.

Block 1601 includes registering a user of the application and may include recording user information relating to their insulin requirements. For example, and not limitation, registration component 431 of mobile computing device 302 (FIG. 4) may be configured to register a user of a coordination application, which may include recording user information relating to their insulin requirements (e.g., diabetic type, body weight, TDBD, ISF, etc).

Block 1602 includes receiving information relating to the non-fasting insulin therapy used by the user in an overall period. For example, and not limitation, non-fasting therapy component 432 of mobile computing device 302 (FIG. 4) may be configured to receive information relating to the non-fasting insulin therapy used by the user in non-fasting period 102 of overall period 100 (FIG. 1), in some embodiments, from the non-fasting therapy device, such as smart insulin pen 210 or an application governing the use of the non-fasting therapy device. Alternatively, this may be received from the user and/or from a doctor.

Block 1603 includes receiving information relating to the fasting delivery device delivering correction bolus doses within a fasting period of the overall period. For example, and not limitation, delivery device therapy component 433 of mobile computing device 302 (FIG. 4) may be configured receive information relating to delivery device 230 delivering correction bolus doses 130*a*-130*e* within fasting period 104 of overall period 100 (FIG. 1). This information may be received from controller 232 of delivery device 230 or from a separate application governing the user of delivery device 230.

Block 1604 includes providing coordination between the non-fasting and fasting therapies and doses. For example, and not limitation, coordination component 434 of mobile computing device 302 (FIG. 4) may be configured to provide coordination between the non-fasting and fasting therapies and doses to the user, for example by providing instructions to the user on when and how to apply, utilize and remove delivery device 230 and/or when and how to deliver basal and/or meal bolus doses utilizing the non-fasting mode of insulin therapy as described or intimated anywhere in this disclosure. Such coordination may include providing an ISF for delivery device 230 based on the use of the non-fasting therapy. The coordination may include providing an ISF at the end of the use of delivery device 230 during fasting period 104. The coordination may provide additional parameter information for coordination between the therapies, including insulin on board at the time of transition between the therapies and/or basal drift.

Block 1605 includes providing recommendations to the user. For example, and not limitation, recommendation component 435 may be of mobile computing device 302 (FIG. 4) may be configured to provide recommendations to the user. Such recommendations may include daily basal dose optimization to help the user tune their basal insulin in a subsequent non-fasting period 102 (FIG. 1). Such recommendations of an adjustment to basal insulin delivery during non-fasting period 102 may in some cases be based on a learned value of DIA. Such recommendations may include analyzing prior blood glucose data from prior fasting periods 104 to detect a long-term drift and/or trend and provide a recommendation to adjust basal dosing and/or meal bolus dosing during non-fasting period 102 and/or to adjust ISF for calculation of correction doses 130*a*-130*e* in a future fasting period 104 in order to attenuate or eliminate such drift. Such recommendations may include indicating an amount of insulin to fill in delivery device 230 for fasting period 104. Such recommendations may include whether and when to use delivery device 230 within overall time period 100, including a timing of when to apply delivery device 230 in overall time period 100. Such recommendations may include an adjustment of a therapy or of a therapy parameter including but not limited to recommendations to exercise at a certain time or for an amount of time.

Block 1606 includes providing predictive outcomes associated with an adjustment of a therapy or therapy parameters of the non-fasting therapy and the fasting delivery device (for example, an improved time in range), where the adjustment is represented by a hypothetical scenario. For example, and not limitation, prediction component 436 of mobile computing device 302 (FIG. 4) may be configured to provide predictive outcomes associated with an adjustment of a therapy or therapy parameters of the non-fasting therapy and fasting delivery device 230. For example, a scenario may be predicted if the user wears the delivery device at night, between X and Y hours, what their blood glucose levels may be. As another example, a scenario may be predicted if the user does not wear delivery device 230 for a night, what their blood glucose levels may be and/or other possible outcomes. As a further example, a scenario may be predicted if the user changes a daily basal amount of insulin from A units to B units, what their blood glucose levels may be and/or other possible outcomes.

In some embodiments, a user's data can be uploaded and analyzed to determine the relative benefit of delivery device 230 to an existing non-fasting therapy, for example, based on an increase time in range (TIR) when utilizing delivery device 230 compared to the existing non-fasting therapy.

Figure 17:
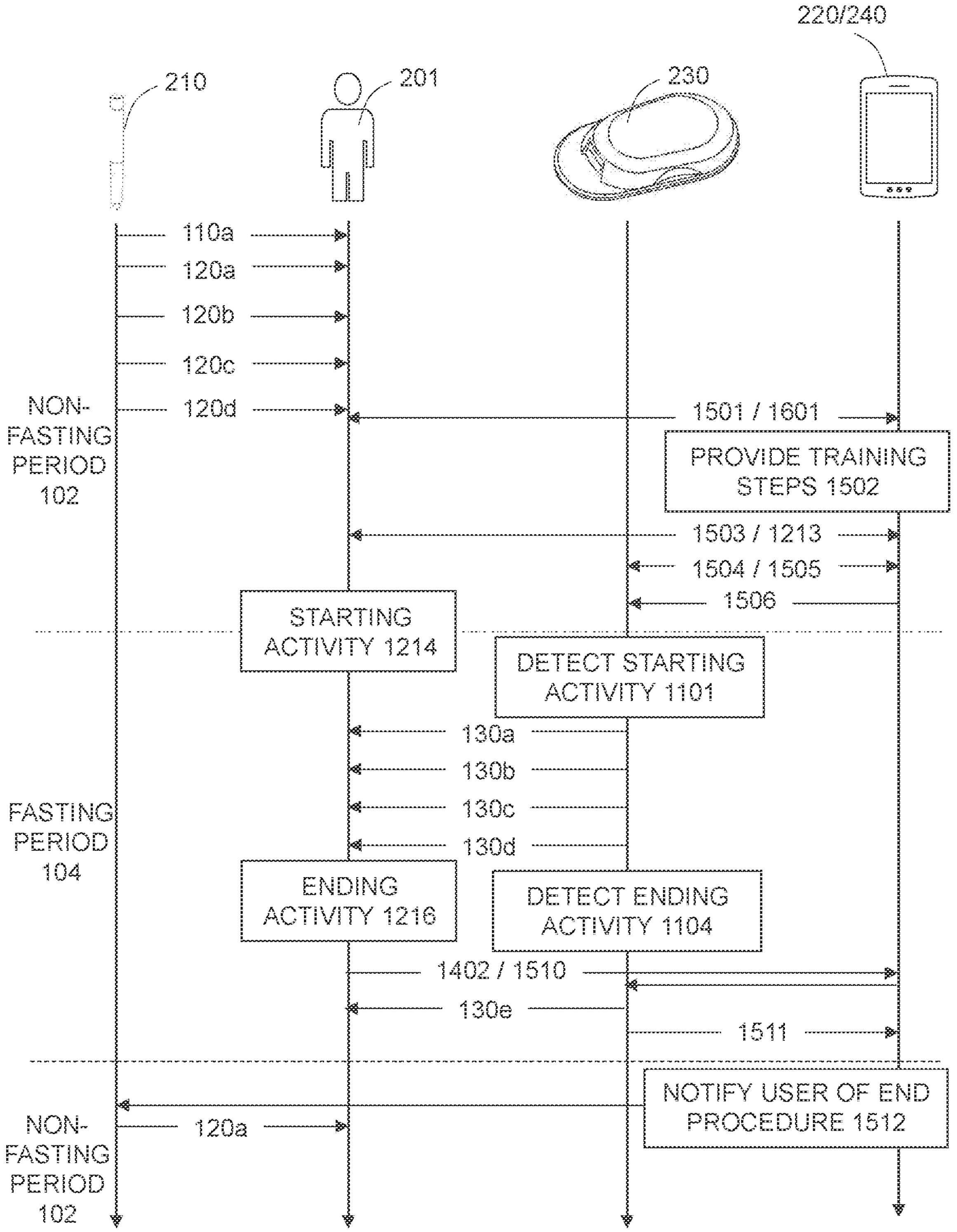
FIG. 17 is a graph illustrating an example use case for controlling delivery of insulin during a fasting period and/or for coordinating such fasting period insulin management with another therapy modality utilized during a non-fasting period, according to some example embodiments.

FIG. 17 illustrates a use case with time extending vertically from top to bottom of the figure and interactions shown as horizontal lines with arrows extending between devices and/or entities involved in methods of insulin management for delivering insulin during fasting period 104 and/or coordination of such fasting period 104 insulin management with another therapy modality utilized during non-fasting period 102, in accordance with some example embodiments.

FIG. 17 illustrates a non-limiting, example use case including user 201, insulin pen 210, delivery device 230 and mobile device 220, as previously described in connection with FIG. 2 or anywhere else in this disclosure. In a non-limiting example, user 201 may be a type 1 diabetic, requiring consistent insulin therapy during both non-fasting periods 102 and during fasting periods 104.

As illustrated, user 201 is first operating non-fasting period 102, during which user 201 may self-administer a 24-hour slow-acting basal insulin dose 110*a* and fast-acting meal bolus doses 120*a*-120*d*, for example, utilizing different insulin pens, e.g., insulin pen 210.

At some time during non-fasting period 102 the user may interact with mobile device 220, for example, running a coordination application for use of fasting delivery device 230 with a non-fasting insulin therapy to register the user 1501, 1601 with the app. Upon registration, the coordination app may be configured to provide user training steps 1502 instructing the user how to use delivery device 230 including filling from insulin pen 210. The coordination app may then pair (e.g., wireless communications pairing) with the controller of delivery device 230 and with the CGM (e.g., shown as integral with delivery device 230 but could also be a separate device).

Once registration and pairing are complete, the coordination app may request 1503 and the user may provide 1213 ISF or TDBD to mobile device 220 for determination of ISF as described anywhere in this disclosure, for example FIG. 7. Where it is determined rather than provided by the user, mobile device 220 may determine ISF as described anywhere herein and provide the ISF to delivery device 230 (e.g., pump controller 232).

The user may then perform 1214 a starting activity 140 as described anywhere in this disclosure. In some embodiments, this may include filling delivery device 230 with insulin as described in connection with at least FIGS. 13A-13L (e.g., blocks 1211 and 1212 in FIG. 12).

Upon detection 1101 of starting activity 140, delivery device 230 calculates and delivers correction doses 130*a*-130*d* to the user 201 in response to actual and/or evaluated blood glucose values of the user during fasting period 104 (see e.g., block 1215 in FIG. 12), for example as described anywhere in this disclosure and especially in connection with FIG. 7.

At some point the user performs 1216 an ending activity 150 to signal a fast-ending procedure at the end of fasting period 104. Upon detection 1104 of this ending activity 150, the fast ending procedure may be entered. In some embodiments where the user's blood glucose is at target or within a target range after initiation of the fast ending procedure, no final correction dose 130*e* may be delivered to the user. However, if the user's blood glucose is above target, e.g., for reasons as described anywhere in this disclosure, delivery device 230 may deliver a fast ending bolus 130*e* to the user (see, e.g., block 1217 in FIG. 12).

In yet other embodiments, the user intends to eat a meal at the beginning of the upcoming non-fasting period 102. In such embodiments, the user provides information 1402 on the expected upcoming fast-breaking meal (e.g., carbohydrate information, etc) to mobile device 220 and mobile device 220 provides 1510 such details to delivery device 230.

Based on the meal information and current blood glucose levels, delivery device 230 determines a fast-breaking meal bolus and delivers it to the user as bolus 130*e*. As stated previously, in some cases the calculated fast-breaking meal bolus is larger than an amount of insulin remaining in delivery device 230. In such cases, bolus 130*e* comprises the remainder of the insulin in delivery device 230 and then delivery device 230 sends, and mobile device 220 receives 1511 details of fast-ending bolus 130*e*, which may include how much insulin is yet to be delivered via smart pen 210. The remainder of the calculated fast-breaking meal bolus is delivered manually, in non-fasting period 102, by the user via smart insulin pen 210. For example, mobile device 220 may notify the user of an end procedure in which the user delivers the fast-ending bolus, in non-fasting period 102, via smart pen 210. In some embodiments, mobile device 220 may be configured to send instructions and/or dosing information for this fast-ending bolus to smart pen 210 such that smart pen 210 may be pre-set to deliver this fast-ending bolus.

Following is an example use case related to a user utilizing a fasting-period insulin delivery device as described anywhere in this disclosure. For example, with respect to FIGS. 1 and 2, User A administers a 24-hour basal insulin dose of slow-acting insulin during non-fasting period 102 of overall period 100. User A also eats multiple meals during non-fasting period 102 and administers an appropriate amount of fast-acting insulin via insulin pen 210. At the end of non-fasting period 102, User A prepares delivery device 230 for use and then applies delivery device 230 to his or her body, as described anywhere in this disclosure. In some embodiments, preparing and/or applying delivery device 230 may constitute a starting activity 140 as described anywhere in this disclosure. However, the user may also or alternatively carry out any other suitable starting activity 140 as described anywhere in this disclosure. At the beginning of fasting period 104, glucose monitor 205 determines User A's blood glucose levels to be 200 mg/dL. Glucose monitor 205 is configured to provide blood glucose measurements to delivery device 230 as described anywhere in this disclosure. User A provides his or her insulin sensitivity factor (ISF) or total daily basal dose (TDBD) from a prior 24-hour period, from which ISF may be calculated as described herein. Based on received blood glucose measurements from monitor 205, delivery device 230 sets a target blood glucose of 120 mg/dL and safety factors as appropriate and determines an assumed IOB calculated to bring User A's blood glucose from the current 200 mg/dL down to the target of 120 mg/dL over the course of fasting period 104. Since assumed IOB accounts for all initial blood glucose elevation, delivery device delivers the first correction dose as zero. Over the remainder of fasting period 104, delivery device 230 periodically receives blood glucose measurements from glucose monitor 205, evaluates them as described anywhere herein, adjusts IOB, target BG and/or safety factors accordingly, and calculates correction doses based on differences between evaluated blood glucose values and the target blood glucose, adjusting the difference by the user's ISF and then reducing the result by IOB. For at least one such correction dose calculation, with a User A's ISF of 20 mg/dL per unit, the dose is calculated to be 4 units (e.g., (200−120)/20)=4), but delivery device 230 has a set limit to deliver no more than 0.5 units in any 5 minute period (e.g., the period between received glucose measurements) and, accordingly, divides or limits the initially calculated dose of 4 units to a correction dose for delivery of 0.5 units. This ensures User A's blood glucose does not crash too quickly based on the larger 4 unit dose. Delivery device 230 then iterates through the calculation process as additional glucose measurements are received and evaluated as necessary. As a result of the above interactions and insulin delivery, User A wakes near the end of fasting period 104 with a blood glucose level of 150 mg/dL, which is elevated compared to the target of 120 mg/dL. In some cases, this elevation is caused by conservative insulin dosing during fasting period 104 specifically designed to avoid over-delivering insulin when the user is sleeping and not eating. Based on User A selecting to initiate a fast-ending procedure, or based on delivery device 230 detecting such selection as an ending activity 150 (or detecting any other ending activity 150 described herein), delivery device 230 calculates a final bolus dose to be delivered to User A in fasting period 104 based on the current blood glucose of 150 mg/dL, the target of 120 mg/dL, User A's ISF of 20 mg/dL per unit, and any remaining IOB. A dose of 0.5 is determined and delivered by delivery device 230 and fasting period 104 ends. User A may then begin the following non-fasting period 102, injecting him or herself with slow acting basal insulin 110*a* and/or fast acting meal bolus doses 120*a*-120*d* via insulin pen 210 to manually control his or her blood glucose during non-fasting period 102.

As another use case building upon the prior paragraph's use case, delivery device 230 (or a mobile computing device 220, see, FIG. 2) may be configured to detect starting activities 140 associated with the use of device 230. As stated above, User A filling delivery device 230 with insulin and/or attaching delivery device 230 to his or her body may be detected as such a starting activity 140 and initiate automated delivery of insulin from delivery device 230 as described in the previous use case (or anywhere else in this disclosure). Upon waking near the end of fasting period 104, such waking and/or movement of User A may be detected as an ending activity 150 as described anywhere herein and, responsive to such detection, delivery device 230 may coordinate the fast-ending procedure described in the prior use case, where the final correction dose of 0.5 units is delivered to User A at the end of fasting period 104 in expectation this dose will bring User A's blood glucose down to the target.

As yet another use case building upon the prior paragraphs' use cases, at the end of fasting period 104, upon waking, User A's blood glucose is 150 mg/dL as previously described. However, in this use case, User A intends to eat breakfast in, perhaps the next 15 minutes and, so, provides details of this intended breakfast meal (e.g., carbohydrate content, etc) to delivery device 230 and delivery device 230 calculates a fast-breaking bolus of insulin sufficient to both counteract the expected upcoming meal and the current elevation in User A's blood glucose as described anywhere in this disclosure. This fast-acting bolus is calculated to be 4 units of insulin, however delivery device 230 only has 1 unit of insulin remaining in its reservoir. Based on this deficiency, delivery device delivers the remaining 1 unit of insulin to User A and fasting period 104 ends. Delivery device 230 (and/or mobile device 220 running an insulin management application as described anywhere herein) then provides instructions to User A on how to provide the remaining 3 units of insulin manually, during the non-fasting period 102, using insulin pen 210. In some cases, delivery device 230 (and/or mobile device 220 running an insulin management application as described anywhere herein) also provides recommendations and/or predictive outcomes to User A regarding his or her insulin management. For example, delivery device 230 or mobile device 220 may provide User A with a recommendation to adjust his or her basal insulin dosing using pen 210 in the non-fasting period 102 in order to better control glucose drift as described anywhere herein, alone with a prediction of what User A's waking blood glucose might be if the recommendation is followed.

FIGS. 18A to 18E are graphs that illustrate exemplary storylines of users using the fasting-time delivery method during a session of a fasting period 1004, for example, overnight. While the axis labels blood glucose as represented by the graphs of FIGS. 18A-18E, the lines may represent either BG or IOB (of course having different labels and values for IOB) because one may be derived from the other. Actual BG and Expected BG may be derived from Actual IOB and Assumed IOB and vice versa, as may be appreciated by a person skilled in the art.

Figure 18A:
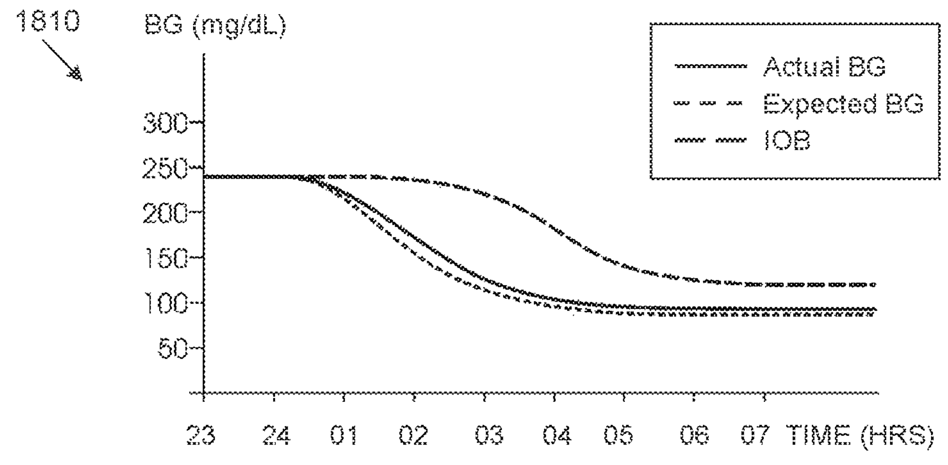
FIGS. 18A to 18E are graphs illustrating example patient storylines during a method of controlling delivery of insulin, according to some example embodiments.

FIG. 18A is a graph 1810 that represents blood glucose over time during a fasting wear session. The solid line represents Actual BG trend/profile over time as measured by a CGM. The line of small dashes represents Expected BG trend/profile based on an Assumed External IOB profile over time as calculated at the start of the session based on assumed insulin sufficiency as described above. The line of larger dashes represents IOB calculated both from assumed IOB and from insulin delivery device 230 delivered.

Figure 18B:
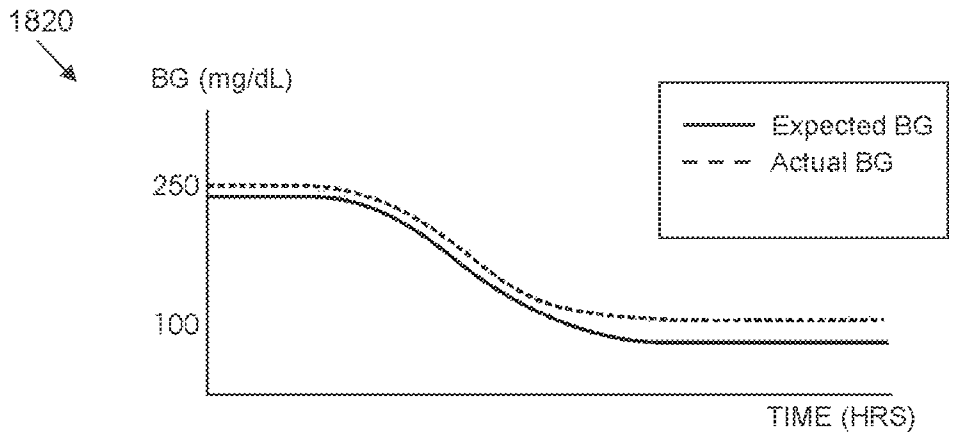

FIG. 18B is a graph 1820 that represents blood glucose over time during a fasting wear session. The line of small dashes represents Actual BG trend/profile over time as measured by a CGM. The solid line represents Expected BG trend/profile based on Assumed IOB. In this example of a wear session, the Actual BG/IOB matches the Expected/Assumed BG/IOB so the assumption of external insulin sufficiency was true and no device insulin needed to be delivered. Notably, without the use of safety factors and/or biasing toward less insulin delivery in the context of any unknowns that may affect blood glucose values as described herein, especially calculation and utilization of assumed IOB, a device would have delivered insulin incorrectly at the start of session if uninformed by external insulin, which would have resulted in a dangerous overnight hypoglycemic event.

Figure 18C:
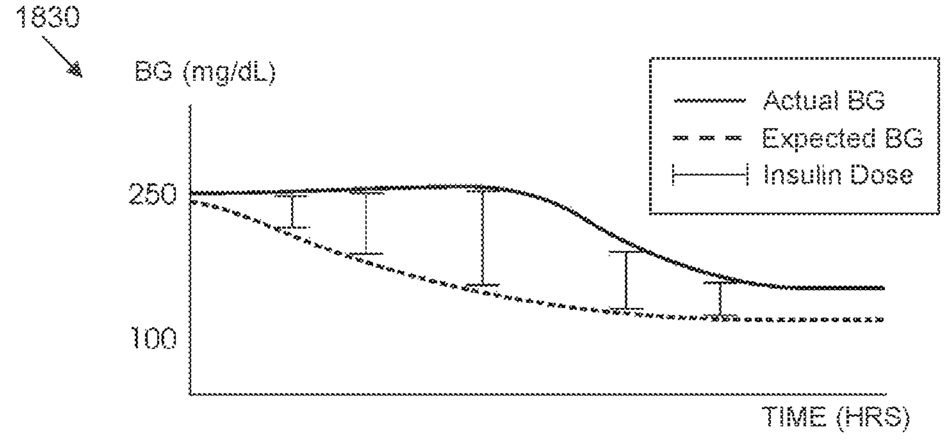

FIG. 18C is a graph 1830 that represents blood glucose over time during a session. The solid line represents Actual BG trend/profile over time as measured by a CGM, showing an example of where actual glucose does not trend downward as expected, meaning the user likely did not take sufficient meal bolus at dinnertime (e.g., bolus 120*d* in FIG. 1) or before applying delivery device 230 and starting fasting period 104. The line of small dashes represents Expected BG trend/profile based on Assumed External IOB profile over time as calculated at the start of the session based on assumed insulin sufficiency as described above. The vertical lines schematically represent the time period(s) during which insulin was delivered in small correction doses 130*a*-130*e*. Notably, although the Assumed External IOB was not true to the actual, the algorithm was able to quickly learn that External IOB was not sufficient and was able to deliver correction insulin to ensure the user woke up in the target range.

Figure 18D:
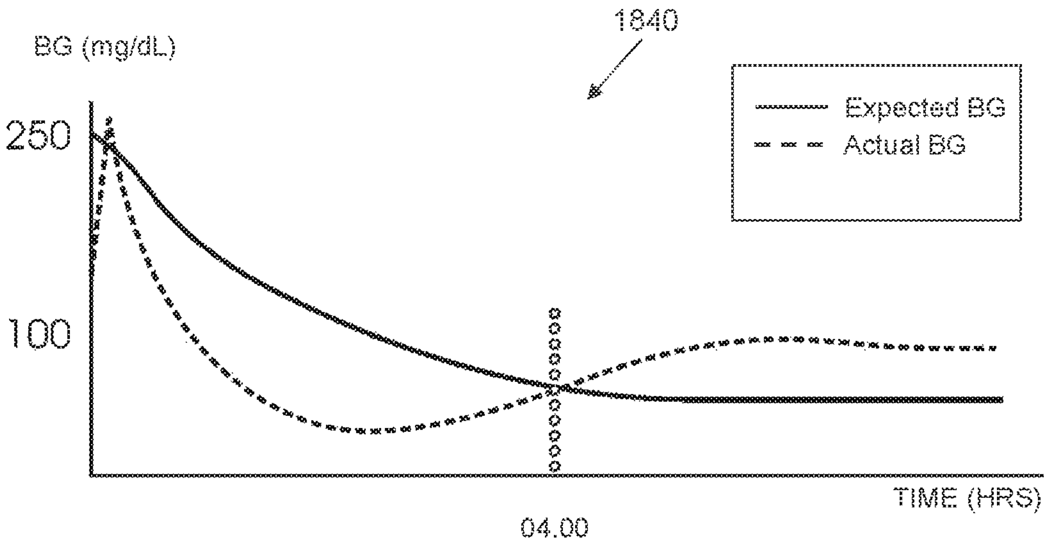

FIG. 18D is a graph 1840 that represents blood glucose over time during a session where the BG drops below expected overnight. The dashed line represents Actual BG trend/profile over time as measured by a CGM, showing an example of where actual glucose dropped downward unexpectedly toward hypoglycemia early during the session, meaning the user took too much meal bolus insulin at dinnertime (e.g., bolus 120*d* in FIG. 1) or before applying the delivery device. The solid line represents Expected BG trend/profile based on Assumed External IOB profile over time as calculated at the start of the session based on assumed insulin sufficiency as described above. Notably, the delivery device did not deliver insulin at the start of the session despite being above target because of the implementation of a safety factor and/or biasing toward less insulin delivery in the context of any unknowns that may have affected blood glucose values as described herein. This use case also displays the benefit of upward adjustment to assumed IOB when initial blood glucose levels rise at the beginning of fasting period 104 (FIG. 1), as previously described in connection with at least FIG. 7. By adjusting assumed IOB upward to account for such an initial rise in blood glucose instead of dosing insulin, a potentially dangerous hypoglycemic event was further avoided. If insulin had been delivered responsive to the initial glucose being higher than a standard clinical target, the result would have been an even more severe overnight hypoglycemic event.

Figure 18E:
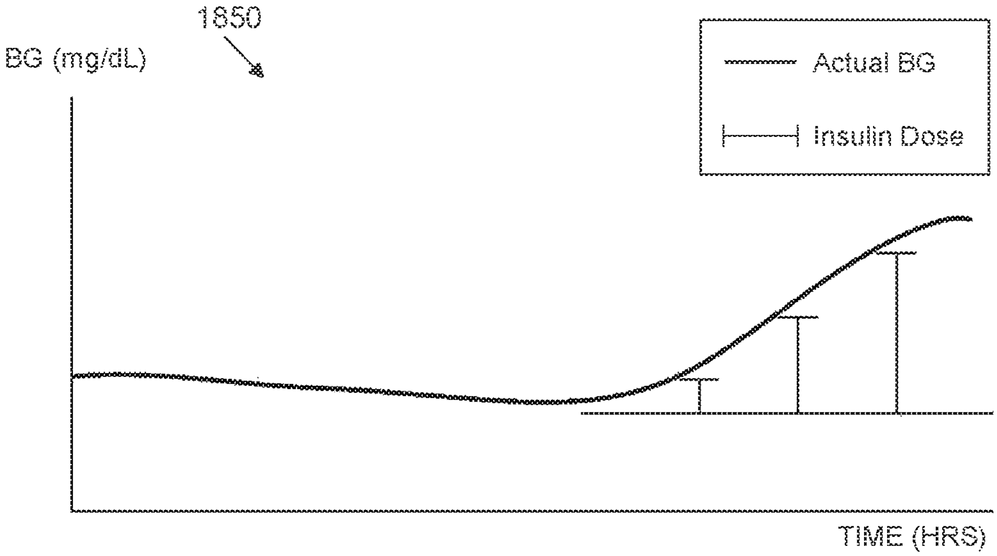

FIG. 18E is a graph 1850 that represents blood glucose over time during a session illustrating a session wherein Actual BG rises slowly towards end of session (e.g., dawn effect). The solid line represents Actual BG trend/profile over time as measured by a CGM, showing an example of where the actual glucose rose upward toward the end of the session (dawn effect), which could be caused by external basal insulin or other physiological factors. The vertical lines generally represent time period(s) during which correction doses of insulin were delivered by the delivery device dose calculation. Notably, because the safety factor decreases over time based on the assumption reduction in likelihood of external insulin, the delivery device delivered sufficient insulin to reduce the "dawn effect" otherwise experienced by some MDI users. Advantageously, the delivery algorithm allows for daytime MDI diabetes management users to benefit from nighttime continuous AID wear, increasing time in range without increasing hypoglycemia risk.

Glucagon Delivery Embodiments

Figure 19:
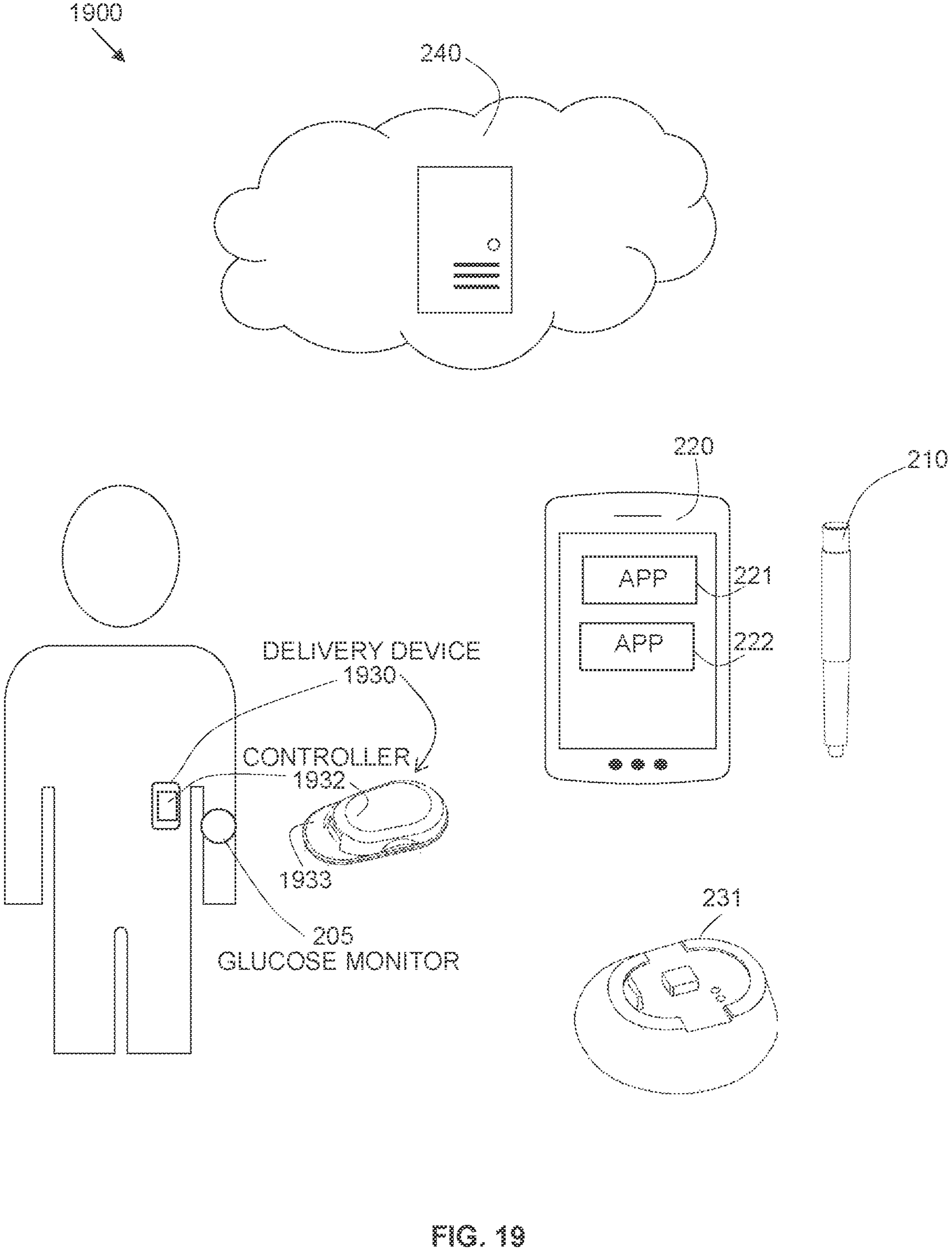
FIG. 19 is a schematic diagram illustrating an example embodiment of an overall therapy arrangement, according to some example embodiments.

FIG. 19 is a schematic diagram which illustrates an example embodiment of an overall therapy arrangement 1900 in which described glucagon management methods of a delivery device in the form of a pump 1930 is used, for example by user 201 as previously described anywhere in this disclosure.

Pump 1930 may be utilized at any time of day or night. Delivery device 1930 is configured to deliver glucagon in one or more small correction doses based at least in part on periodic blood glucose measurement from CGM 205 (see, e.g., FIG. 2). In some embodiments, CGM 205 may be incorporated into delivery device 1930. In other embodiments, CGM 205 may be a separate CGM worn by the user day and night.

As with delivery device 230, in some embodiments, delivery device 1930 may be provided in a kit (not shown). Delivery device 1930 comprises a durable unit into which a disposable dispensing unit 1933 containing the glucagon is fitted. Delivery device 1930 may have an applicator (not shown but similar to applicator 235) for use while filling delivery device 1930 with glucagon and/or for applying delivery device 1930 to the user's body, for example as described for delivery device 230 anywhere in this disclosure. Charger 231 may also be configured to charge the durable unit of delivery device 1930.

The durable unit of delivery device 1930 includes a controller 1932 for controlling the delivery of glucagon from delivery device 1930 according to a delivery algorithm. The delivery algorithm may be provided entirely on controller 1932. This may be provided in the form of software and/or hardware components. In a first alternative, the delivery algorithm may be provided remotely instructing the delivery amounts to the controller 1932. This may be provided remotely from: cloud computing system 240; computer application 222 on user's mobile computing device 222; or another form of computing device or system. In a second alternative, the delivery algorithm may be distributed between any two or more of: the controller 1932; cloud computing system 240; computer application 222 on a user's mobile computing device 220; and another form of computing device or system.

Figure 20:
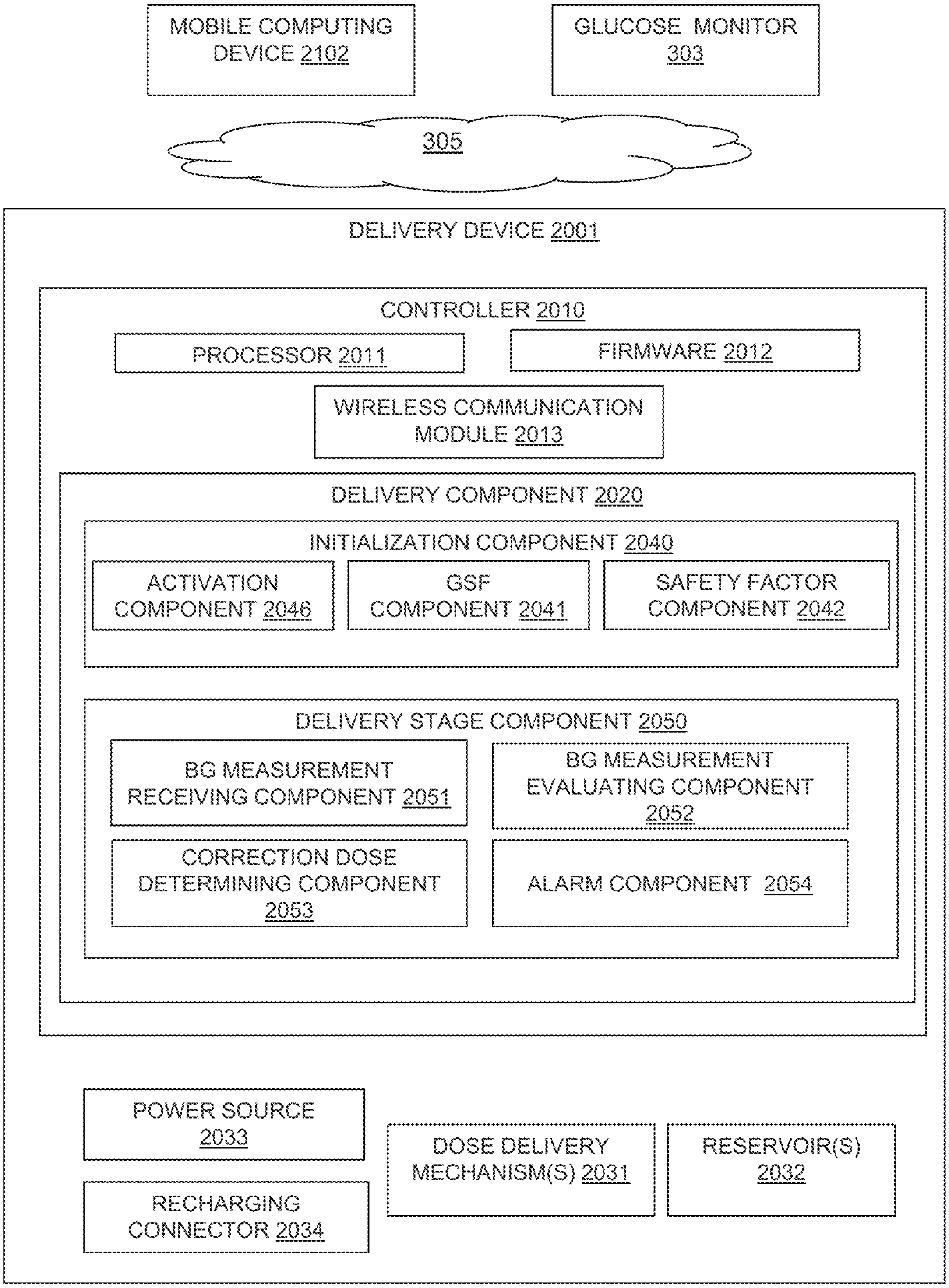
FIG. 20 is a block diagram of a system of controlling delivery of glucagon, according to some example embodiments.

An example embodiment of a delivery device 2001 comprising controller 1932 and delivery device 1930 is illustrated by the schematic block diagram of FIG. 20. Referring to FIG. 20, device 2001 may include a power source 2033 and a recharging connector 2034. Device 2001 may include a wireless communication module 2013 for communication via a wireless network 2005 with a continuous glucose monitor (GCM) 303 for receiving glucose measurement of a user. Device 2001 may also be configured to communicate via a wireless network 305 with a mobile computing device 2102 such as a mobile phone, laptop or desktop computer. In some embodiments, mobile computing device 2102 may correspond to mobile computing device 220 of FIG. 2. In some embodiments, glucose monitor 303 may correspond to CGM 205 of FIG. 2.

Controller 2010 may include a microcontroller in the form of a processor 2011 with firmware 2012 that controls the operation of delivery device 2001. Firmware 2012 may be provided by the components of controller 2010. Processor 2011 may be a hardware module or a circuit for executing the functions of the described components which may be software units executing on the at least one processor 2011. Memory may be configured to provide computer instructions to processor 2011 to carry out the functionality of the components.

Controller 2010 may include a delivery component 2020 that may be in communication with mobile computing device 2102 and/or glucose monitor 303 and determines when and how much to dispense in a dose by means of a dose delivery mechanism 2031 of delivery device 2001 from a reservoir 2032 of the delivery device 2001. Delivery component 2020 may include an initialization component 2040 for an initial configuration stage of the delivery component 2020 and a delivery stage component 2050 for a delivery stage.

In some embodiments, controller 2010 may also be configured to cause dose delivery mechanism 2031 to deliver a predetermined and/or calculated amount of glucagon from reservoir 2032 based at least in part on blood glucose levels falling below a predetermined low level (e.g., 40 mg/dl, 50 mg/dl, 60 mg/dl, 70 mg/dl) and/or to maintain blood glucose levels above a predetermined safe level (e.g., 60 mg/dl, 70 mg/dl, 80 mg/dl) during episodes of intense user activity (e.g., exercise).

Initialization component 2040 may include an activation component 2046 for detecting activation of the delivery device to commence delivery of glucagon as described anywhere in this disclosure. In some but not all embodiments, initialization component 2040 may include a glucagon sensitivity factor (GSF) component 2041 for receiving a glucagon sensitivity factor from the user or from a doctor and/or for deriving or otherwise determining a glucagon sensitivity factor from one or more other parameters. For example, in some embodiments, default amounts of glucagon may be based on a doctor's prescription, input by a user, or may be based on the user's age and/or weight from a look up table. In embodiments where a GSF is utilized, GSF component 2041 may be configured to determine, adjust and/or adapt GSF, or an effective GSF, based on one or more of a variety of factors, including but not limited to prior and/or current blood glucose values, IOB, patient history, knowledge of whether the user is awake and/or aware of the event, e.g., via interaction with a UI of mobile device 2102. Initialization component 2040 may include a safety factor component 2042 for providing one or more safety factors to parameters on which dose correction is based as described anywhere in this disclosure, for example, evaluating blood glucose values and/or target blood glucose as described anywhere in this disclosure.

Delivery stage component 2050 may include a blood glucose (BG) measurement receiving component 2051 for periodically receiving blood glucose measurements on which correction bolus doses of glucagon are based. Delivery stage component 2050 may include a measurement evaluating component 2052 for smoothing, manipulating, modifying and/or supplementing the received blood glucose measurements to reduce the effect of noise or abrupt perturbations on obtained blood glucose values as described anywhere in this disclosure. In some embodiments, such smoothing, manipulating, modifying and/or supplementing the received blood glucose measurements may also be considered implementing a safety factor on the received blood glucose measurements in order to avoid overdosing over or underdosing glucagon.

Delivery stage component 2050 may include a correction dose determining component 2053 for determining whether a glucagon correction bolus dose is appropriate based on one or more true and/or evaluated blood glucose measurements to bring the user to a target blood glucose (or above such a target value). Correction dose determining component 2053 may be configured to compare a received blood glucose value from measurement receiving component 2051 (or a smoothed, manipulated, modified and/or supplemented value from evaluating component 2052) to a target blood glucose. In some embodiments, correction dose determining component 2053 is configured to make an affirmative determination to deliver a predetermined correction dose of glucagon (e.g., 1 mL) calculated to increase the user's blood glucose level above the target blood glucose level based on one or more factors. Such factors may comprise the received and/or evaluated blood glucose value first falling below the target blood glucose. Such factors may comprise the received and/or evaluated blood glucose value staying below the target blood glucose for one or more consecutive iteration periods of received and/or evaluated blood glucose values, or for a predetermined interval of time. Such factors may comprise the received and/or evaluated blood glucose value being below the target blood glucose and a first derivative (rate of change) of the received and/or evaluated blood glucose values are below a predetermined value (e.g., 0), e.g., indicating blood glucose levels are below the target and are not increasing or are not increasing fast enough. Such factors may comprise the received and/or evaluated blood glucose value being below the target blood glucose and a second derivative (acceleration of change) of the received and/or evaluated blood glucose values are below a predetermined value (e.g., 0), e.g., indicating blood glucose levels are below the target and are not increasing fast enough. In some but not all embodiments, where a glucagon sensitivity factor (GSF) is utilized in determining a size of a correction dose of glucagon to be delivered, amounts of delivered glucagon may be based on a doctor's prescription, input by a user, or may be based on the user's age and/or weight from a look up table (as described above). In some such embodiments, correction dose determining component 2053 may also, or alternatively, be configured to determine, adjust and/or adapt GSF, or the effective GSF, based on one or more of a variety of factors, including but not limited to prior and/or current blood glucose values, IOB, patient history, knowledge of whether the user is awake and/or aware of the event, e.g., via interaction with a UI of a mobile device 2102.

Delivery stage component 2050 may include an alarm component 2054 configured to trigger an alarm or send, or cause to be sent, an indication to another mobile device (e.g., 2102) that the blood glucose levels of the user of delivery device 2001 have triggered the target blood glucose (e.g., has fallen below the target). In some embodiments, such a mobile device may be monitored by a caregiver, such as a doctor or a parent of a child using the glucagon delivery device, thereby allowing the caregiver to be notified of developments regarding the user's blood glucose and care.

Figure 21:
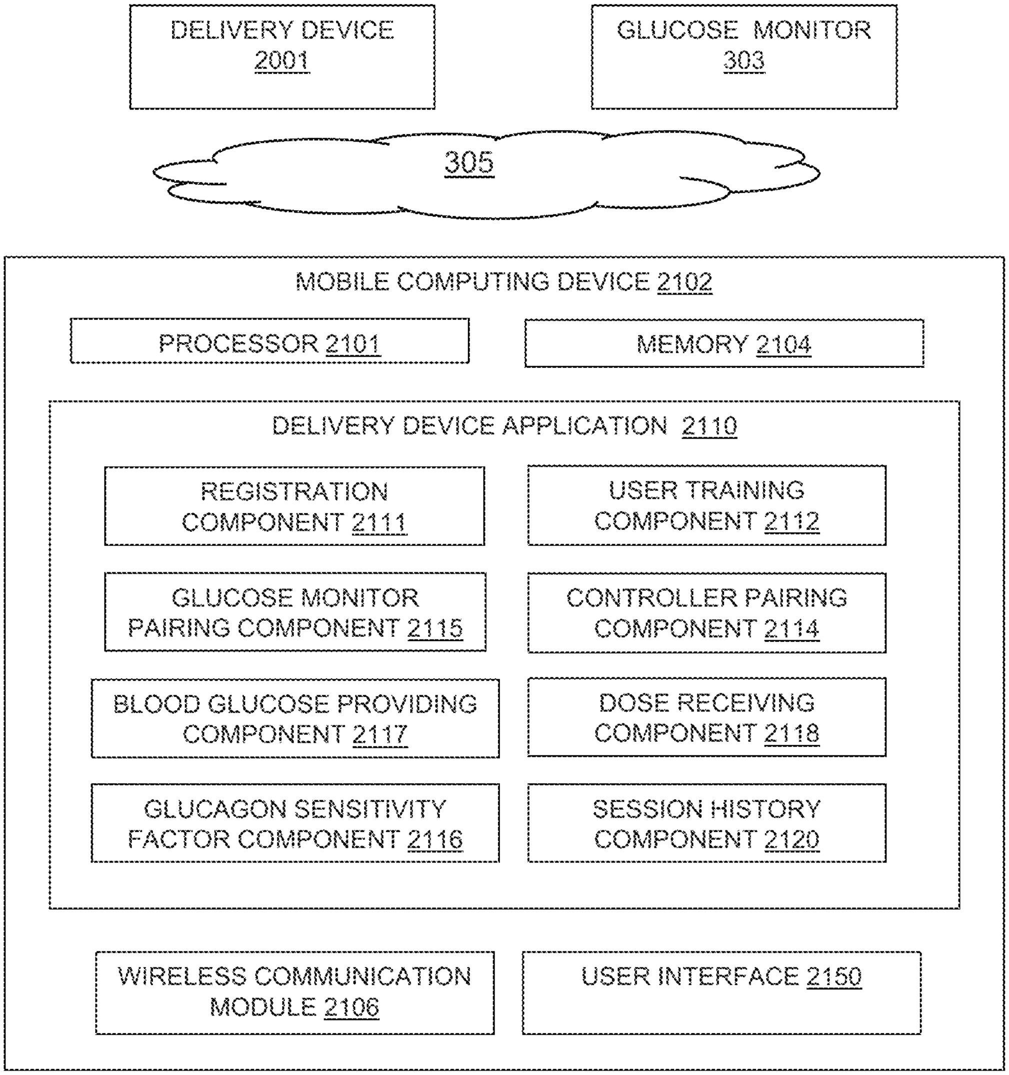
FIG. 21 is a block diagram of a system providing a computer application for interacting with a delivery device for controlling delivery of glucagon, according to some example embodiments.

FIG. 21 illustrates a block diagram showing an example embodiment of a system including mobile computing device 2102 such as a mobile phone, laptop or desktop computer. The mobile computing device 2102 may communicate via wireless network 305 with delivery device 2001, which may comprise delivery device 1930. Mobile computing device 2102 may also communicate via wireless network 305 with glucose monitor 303 for receiving glucose measurement of a user. Mobile computing device 2102 may include a wireless communication module 2106 configured to facilitate any and all wireless communications with other devices. Mobile computing device 2102 may also include a user interface 2150 configured to display any indications and/or information to the user and/or receive any information from the user as required, desired and/or described anywhere in this disclosure. In some embodiments, one or more portions or functionalities of the processing of controller 1932 including the delivery algorithm may be provided remotely by the mobile computing device 2102. In other embodiments, one or more portions or functionalities of the processing of controller 1932 including the delivery algorithm may be provided remotely by a cloud server either directly to the controller 1932 or in coordination with the mobile computing device 2102.

Mobile computing device 2102 may include a processor 2101 for executing the functions of components described herein, which may be provided by hardware or by software units executing on mobile computing device 2102. The software units may be stored in a memory component 2104 and instructions may be provided to processor 2101 to carry out the functionality of the described components. In some cases, for example in a cloud computing implementation, software units arranged to manage and/or process data on behalf of mobile computing device 2102 may be provided remotely. Some or all of the components may be provided by a software application downloadable onto and executable on mobile computing device 2102.

A delivery device application 2110 may be provided by the hardware or software units for managing the described fasting delivery device as described anywhere in this disclosure. Delivery device application 2110 may include a registration component 2111 for registering a user of the application as described anywhere in this disclosure. Delivery device application 2110 may include a user training component 2112 for providing training steps instructing the user how to use a delivery device as described anywhere in this disclosure, including filling glucagon.

Delivery device application 2110 may include a controller pairing component 2114 for pairing mobile communication device 2102 running delivery device application 2110 with a controller of delivery device 2001. Delivery device application 2110 may include a glucose monitor pairing component 2115 for pairing mobile communication device 2102 running application 2110 with blood glucose monitor 303 worn by the user.

In some embodiments, delivery device application 2110 may include a glucagon sensitivity factor (GSF) providing component 2116 for providing the user's GSF to the delivery algorithm of the controller of the delivery device 2001 for use in the calculation of the correction doses as described anywhere in this disclosure. In some embodiments, glucagon delivery is not determined based on a GSF of the user, instead being a predetermined dose for all users, a predetermined dose based on age and/or body size of the user, or a dose determined or predetermined according to any other suitable metric(s).

Delivery device application 2110 may include a blood glucose providing component 2117 for receiving blood glucose measurements as monitored from glucose monitor 303 and sending these to the controller for calculation of correction bolus doses as described anywhere in this disclosure. In some embodiments, application 2110 may include a dose receiving component 2118 for receiving a record of glucagon correction bolus doses given by the delivery device as described anywhere in this disclosure.

Delivery device application 2110 may include a session history component 2120 for providing a session history including a display of glucagon correction doses given by the delivery device together with the blood glucose measurements and, in some cases, including additional statistics for user information as described anywhere in this disclosure. For example, as previously described, session history component 2120 may be configured to provide an indication that the blood glucose levels of the user of delivery device 2001 have triggered the target blood glucose (e.g., has fallen below the target). In some such embodiments, mobile device 2102 (or any other electronic device configured to receive such an indication) may be monitored by a caregiver, such as a doctor or a parent of a child using glucagon delivery device 2001, thereby allowing the caregiver to be notified of developments regarding the user's blood glucose and care.

Session histories for previous sessions may also be provided as described anywhere in this disclosure.

Figure 22:
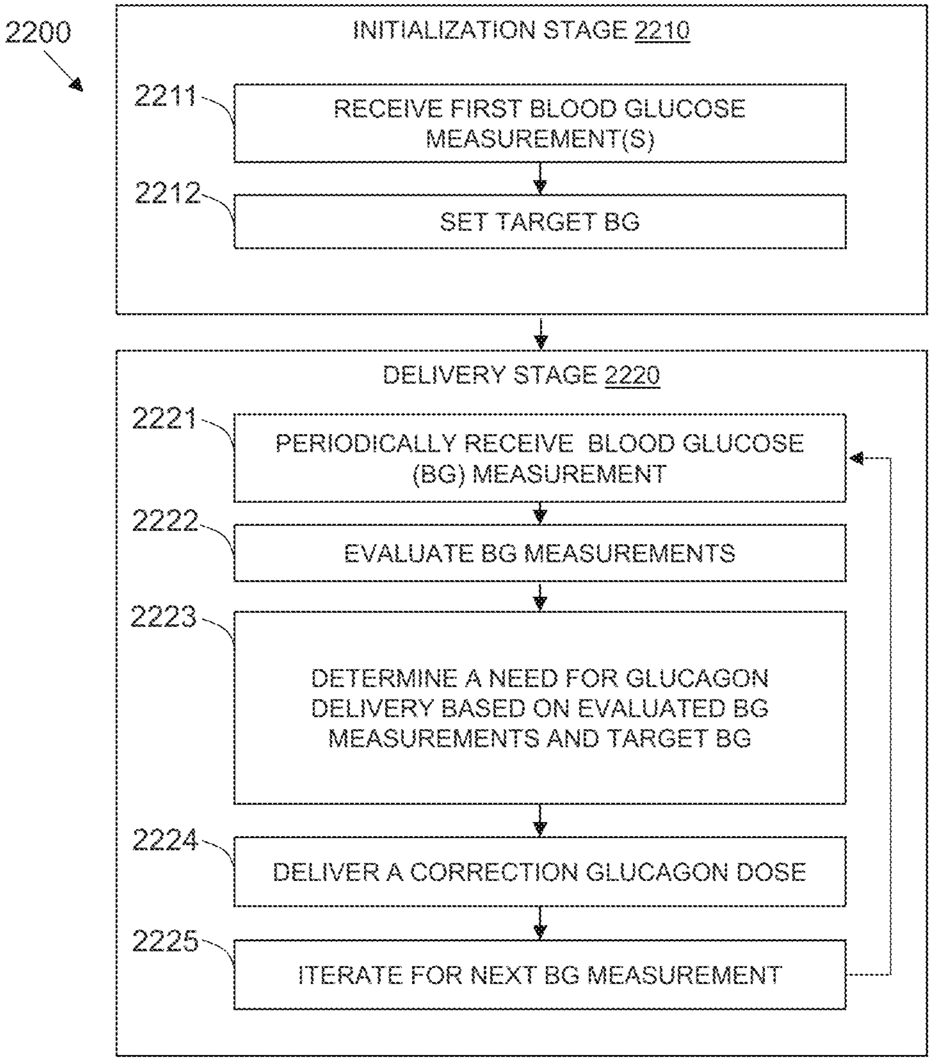
FIG. 22 is a flow diagram of methods of controlling delivery of glucagon, according to some example embodiments.

Referring to FIG. 22, a flow diagram 2200 shows an example embodiment of a method of controlling the delivery of glucagon from a delivery device, for example, delivery device 1930 of FIG. 19. The method may be utilized to deliver glucagon at any time of day or night from delivery device 1930. In some embodiments, no insulin is given by delivery device 1930. Such a method may be carried out at and/or by a controller, such as controller 1932 of delivery device 1930 shown in FIG. 19, at and/or by delivery device 2101 or mobile computing device 2002 as shown in FIGS. 20 and/or 21, and/or remotely at and/or by a server, computing device, or the like, such computing device 500 shown in FIG. 5, instructions then being sent to the controller. In some embodiments, certain steps may be carried out by such an above-described controller of the delivery device and/or with some of the steps carried out remotely to the controller. Accordingly, in some embodiments, such methods may be carried out in cooperation with such an above-described controller with a user application provided on a user's mobile computing device, for example mobile computing device 2102.

While not shown in flowchart 2200, such a method may include delivery device 1930 detecting its own activation, for example and not limitation, when the user starts to wear device 1930. Alternatively, where one or more steps and/or calculation procedures are carried out remotely by another device, such as mobile device 220 or remote cloud device 240, such a method may include detection or receiving notification, by the other device, of such activation of delivery device 1930. For example, in some embodiments, activation component 2046 of delivery device 2001 of FIG. 20 may be configured to perform such detection.

The method may include an initialization stage 2210 in which various parameters and safety factors are set-up for the delivery algorithm, and a delivery stage 2220 in which correction dose(s) are calculated and/or delivered to the user. In some embodiments, some steps, or safety factors, of the initialization stage 2210 may be updated during the delivery stage 2220. In some embodiments, initialization component 2030 of mobile device 2102 of FIG. 21 may be configured for initialization stage 2210 and delivery stage component 2050 may be configured for delivery stage 2220.

Block 2211 includes receiving a first blood glucose measurement. For example, blood glucose measurements may be received periodically from a glucose monitor (e.g., CGM 205 in FIG. 2). In some embodiments, BG receiving component 2051 of delivery device 2001 of FIG. 20 may be configured to perform the functions of block 2211.

Block 2212 includes setting the blood glucose target. For example, as stated above, target blood glucose may be set at a relatively low level (e.g., 40 mg/dl, 50 mg/dl, 60 mg/dl, 70 mg/dl) to guard against severe hypoglycemia. In some embodiments, target blood glucose may be set a predetermined or constant value for all users, or at a respective one of a plurality of constant values for each of a plurality of classifications of user.

As previously described, safety factors may also be applied to actual blood glucose measurements in the form of filtering and/or any other modification thereto as described anywhere in this disclosure. However, such adjustments are largely discussed as evaluating blood glucose measurements at block 2222.

During the delivery stage 2220, at block 2221, blood glucose measurements are periodically received, for example, from a glucose monitor such as CGM 205 in FIG. 2. In some embodiments, BG measurement receiving component 2051 of delivery device 2001 of FIG. 20 may be configured to perform the functions of block 2221.

As stated above, guarding against over-delivering, or calculating to over-deliver, glucagon may be better achieved by utilizing a processed, evaluated and/or filtered proxy of the user's actual blood glucose levels that more accurately represents the long-term trends of the user's actual blood glucose levels while also attenuating, eliminating or otherwise filtering out short-term noise and/or aberrations. Accordingly, at block 2222, the periodically received blood glucose measurements (or a subset thereof) are evaluated. For example, the periodically received blood glucose measurements may be processed and/or filtered as described anywhere in this disclosure in order to obtain a proxy of the user's actual blood glucose levels that more accurately represents the long-term trends of the user's actual blood glucose levels while also attenuating, eliminating or otherwise filtering out short-term noise and/or aberrations.

Accordingly, at block 2222, received blood glucose measurements are evaluated. While such evaluation may be carried out by delivery device 1930 (e.g., controller 1932), mobile device 2102 and/or computing device 500, in some embodiments, such evaluation of blood glucose measurements as described anywhere in this disclosure, or portions thereof, may be carried out by CGM 205. In some embodiments, BG measurement evaluating component 2052 of delivery device 2001 of FIG. 20 may be configured to perform the functions of block 2222.

At block 2223, a need for glucagon delivery is determined based on evaluated blood glucose measurements and target blood glucose. In some embodiments, correction dose determining component 2053 of delivery device 2001 of FIG. 20 may be configured to perform the functions of block 2223 based on one or more factors. Such factors may comprise the received and/or evaluated blood glucose value first falling below the target blood glucose. Such factors may comprise the received and/or evaluated blood glucose value staying below the target blood glucose for one or more consecutive iteration periods of received and/or evaluated blood glucose values, or for a predetermined interval of time. Such factors may comprise the received and/or evaluated blood glucose value being below the target blood glucose and a first derivative (velocity of change) of the received and/or evaluated blood glucose values are below a predetermined value (e.g., 0), e.g., indicating blood glucose levels are below the target and are not increasing or are not increasing fast enough. Such factors may comprise the received and/or evaluated blood glucose value being below the target blood glucose and a second derivative (acceleration of change) of the received and/or evaluated blood glucose values are below a predetermined value (e.g., 0), e.g., indicating blood glucose levels are below the target, are not increasing fast enough, and/or the increase in blood glucose levels is not increasing fast enough.

Block 2224 comprises delivering one or more correction glucagon doses. In some embodiments, dose delivery mechanism 2031 of delivery device 2001 of FIG. 20 may be configured to perform the functions of block 2224. For example, in reference to FIG. 23, one or more glucagon doses 2310 may be delivered to the user by delivery device 1930 upon blood glucose falling below the target value. As illustrated, blood glucose begins to rise after delivery of the one or more glucagon doses 2310 and quickly reaches a level above the target. For example, in some embodiments, if subsequent blood glucose measurements after delivering an initial glucagon dose reveal that blood glucose levels are still under the target and not rising (e.g., first derivate of blood glucose measurement values is zero or negative), or are under the target and not rising fast enough (e.g., second derivative of blood glucose measurements values is not sufficiently large in relation to the first derivative to predict blood glucose levels will rise above the target within a predetermined interval of time (e.g., 15 minutes)) one or more subsequent doses of glucagon may have been delivered.

Figure 23:
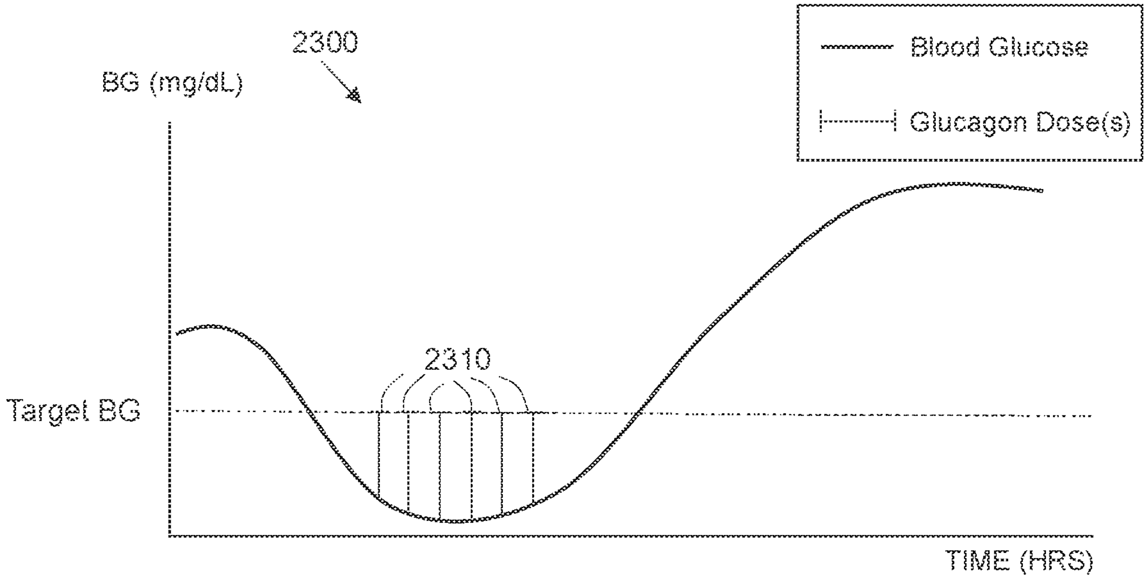
FIG. 23 is a graph illustrating an example patient storyline during a method of controlling delivery of glucagon, according to some example embodiments.

In some embodiments, the size of the glucagon dose(s) may be determined based on age and/or bodyweight of the user. For example, for powder or solution injections, individuals 6 years and older and weighing 25 kg or more may receive 1 mL of glucagon injection, while individuals under 6 years old or weighing less than 25 kg may receive 0.5 mL of glucagon injection. In further example, for autoinjector or prefilled syringes, individuals 12 years and older may receive 1 mg or 0.2 mL of glucagon injection, children 2 to 11 years old and weighing 45 kg or more may receive 1 mg or 0.2 mL of glucagon injection, children 2 to 11 years old and weighing less than 45 kg may receive 0.5 mg or 0.1 mL of glucagon injection, and children under 2 years may receive a doctor determined dose of glucagon injection. In some embodiments, where multiple glucagon doses are delivered, appropriate above-mentioned glucagon dose may be divided into several smaller, micro-doses, for example as shown in FIG. 23.

Block 2225 comprises continuously iterating for the next blood glucose measurement during the delivery stage 2220 to accommodate periodically received blood glucose measurements. When a next received blood glucose measurement is received, the method may include determining whether to deliver another glucagon dose based on an updated calculation, thereby, providing a correction to avoid severe hypoglycemia risk.

A use case for glucagon delivery, for example via delivery device 1930, will now be described. In a first use case, a 9 year old, 30 kg type 1 diabetic girl is attending a sleepover and a friend's house and the girl's parents are concerned about whether she will be able to properly control her blood sugar, especially without their parental supervision. During the early evening, the girl's blood glucose is generally maintained within a range of 100-150 mg/dL. However, once the child has fallen asleep, for any number of reasons including but not limited to overdosing meal bolus insulin or basal insulin during the day, her blood glucose begins to drift downward, for example as shown in FIG. 23. At some time during the night, when the child is sleeping, her blood glucose falls below the target, which may be 40 mg/dl in an example. Since such a lower blood glucose level can interfere with the brain's ability to take up blood glucose for energy, a dangerous hypoglycemic event is occurring. Based on blood glucose values being below the target, delivery device 1930 delivers a 0.5 mg or 0.1 mL of glucagon dose to the girl, and her blood glucose levels quickly rise above the target and into safer territory for her context, sleeping or resting. In some such embodiments, delivery device 1930 delivers the above glucagon dose as a series of micro-doses that, together, total the desired 0.5 mg or 0.1 mL of glucagon dose. In some embodiments, delivery device 1930 sends an alarm message to a mobile device running an application for remote monitoring of the child's blood glucose levels and/or operation of deliver device 1930, for example, providing indication of the hypoglycemic event and/or particulars of the relevant session history to the parent.

Another use case for glucagon delivery, for example via delivery device 1930, will now be described. In a first use case, a 12 year old, 46 kg type 1 diabetic boy is attending an afternoon sporting event and the boy's parents are concerned about whether he will be able to properly control his blood sugar, especially during high levels of physical activity. During the sporting event, the boy's blood glucose is generally maintained within a range of 80-120 mg/dL. However, during a particularly physically demanding interval, his blood glucose begins to drift downward, for example as shown in FIG. 23. At some time during the particularly physically demanding interval, his blood glucose falls below the target, which may be 60 mg/dl in this example, although any other suitable blood glucose target is also contemplated. Since such a low blood glucose level can interfere with muscle's ability to fire maximally and the brain's ability to function effectively and control those muscles, a dangerous hypoglycemic event is occurring. Based on blood glucose values being below the target, delivery device 1930 delivers a 1 mg or 0.2 mL of glucagon dose to the boy, and his blood glucose levels quickly rise above the target and into safer territory for the context of his situation, waking physical exercise. In some such embodiments, delivery device 1930 delivers the above appropriate glucagon dose as a series of micro-doses that, together, total the desired 1 mg or 0.2 mL of glucagon dose.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

Any of the steps, operations, components or processes described herein may be performed or implemented with one or more hardware or software units, alone or in combination with other devices. In one embodiment, a software unit is implemented with a computer program product comprising a non-transient or non-transitory computer-readable medium containing computer program code, which can be executed by a processor for performing any or all of the steps, operations, or processes described. Software units or functions described in this application may be implemented as computer program code using any suitable computer language such as, for example, Java™, C++, or Perl™ using, for example, conventional or object-oriented techniques. The computer program code may be stored as a series of instructions, or commands on a non-transitory computer-readable medium, such as a random access memory (RAM), a read-only memory (ROM), a magnetic medium such as a hard-drive, or an optical medium such as a CD-ROM. Any such computer-readable medium may also reside on or within a single computational apparatus, and may be present on or within different computational apparatuses within a system or network.

Flowchart illustrations and block diagrams of methods, systems, and computer program products according to embodiments are used herein. Each block of the flowchart illustrations and/or block diagrams, and combinations of blocks in the flowchart illustrations and/or block diagrams, may provide functions which may be implemented by computer readable program instructions. In some alternative implementations, the functions identified by the blocks may take place in a different order to that shown in the flowchart illustrations.

A computer program product may include one or more computer readable hardware storage devices having computer readable program code stored therein, said program code executable by one or more processors to implement the described methods.

Some portions of this description describe the embodiments of the invention in terms of algorithms and symbolic representations of operations on information. These algorithmic descriptions and representations, such as accompanying flow diagrams, are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations may be embodied in software, firmware, hardware, or any combinations thereof.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention set forth in any accompanying claims.

Finally, throughout the specification and any accompanying claims, unless the context requires otherwise, the word 'comprise' or variations such as 'comprises' or 'comprising' will be understood to imply the inclusion of a stated integer or group of integers but not the exclusion of any other integer or group of integers.

The invention claimed is:

1. An insulin management method, comprising:

projecting a downward trend of a plurality of received blood glucose measurements and adding the downward trend to one of the plurality of received blood glucose measurements to obtain an evaluated blood glucose measurement;

calculating a correction bolus dose of insulin by comparing the evaluated blood glucose measurement to a target blood glucose to obtain a difference, adjusting the difference by a user insulin sensitivity factor to obtain a resultant insulin dose amount, and compensating the resultant insulin dose amount by a determined insulin on board; and delivering the calculated correction bolus dose of insulin as a plurality of delivered correction bolus doses of insulin from a first insulin delivery device during a fasting period within an overall time period, wherein the first insulin delivery device is not configured to deliver basal insulin, and wherein at least one of a basal dose of insulin and a meal bolus dose of insulin is received by the user from a second non-fasting insulin management modality during a non-fasting period within the overall time period.

2. The method of claim 1, wherein a single non-fasting period and a single fasting period are provided in the overall time period and wherein the single fasting period is the major sleep portion of a user's regular daily routine.

3. The method of claim 1, wherein the user insulin sensitivity factor is derived from a total daily basal insulin dose information received from the second non-fasting insulin management modality in a defined period prior to the fasting period.

4. The method of claim 1, wherein, when the calculated correction bolus dose is a first correction bolus dose calculated during the fasting period, the determined insulin on board is set equal to an assumed insulin on board calculated as an amount of insulin needed to correct the evaluated blood glucose value to the target blood glucose.

5. The method of claim 4, wherein the determined insulin on board comprises the assumed insulin on board and a known delivered insulin from the first insulin delivery device.

6. The method of claim 1, wherein the target blood glucose is fixed for all users.

7. The method of claim 1, wherein delivering the calculated correction bolus dose of insulin as the plurality of delivered bolus doses of insulin from the first insulin delivery device during the fasting period is commenced based on detection of activation of the first delivery device by the user.

8. The method of claim 1, wherein the correction bolus doses of insulin for the fasting period are calculated at each blood glucose measurement timepoint to determine a timing and an amount of insulin required to bring the user to the target blood glucose.

9. The method of claim 1, wherein the evaluated blood glucose measurement is evaluated at least in part by smoothing the plurality of received blood glucose measurements with a low pass filter to reduce the effect of noise and/or abrupt perturbations to obtain blood glucose values.

10. The method of claim 1, wherein the evaluated blood glucose measurement is evaluated at least in part by retaining a received blood glucose measurement that is less than a rolling average of a predetermined number of prior received blood glucose measurements and retaining the rolling average for the received blood glucose measurement otherwise.

11. The method of claim 1, wherein the downward trend is determined based at least in part on a largest negative slope between any of the received blood glucose measurement within a predetermined timeframe and a reference blood glucose measurement.

12. The method of claim 1, wherein the evaluated blood glucose measurement is evaluated at least in part by fitting received blood glucose measurements within a predetermined timeframe to the downward trend having a median slope selected from a plurality of regression fit slopes for different rolling subsets of received blood glucose measurements within the predetermined timeframe.

13. The method of claim 1, wherein the evaluated blood glucose measurement is evaluated at least in part by filtering the received blood glucose measurements, the filtering comprising:

imposing a progressively increasing limit on how much each next received blood glucose measurement can increase compared to the previous received blood glucose measurement for increasing received blood glucose measurements; and amplifying how much each next received blood glucose measurement decreases compared to the previous received blood glucose measurement for decreasing received blood glucose measurements.

14. The method of claim 1, comprising limiting each of the plurality of delivered correction bolus doses to a defined maximum dose per delivered correction bolus dose such that each of the delivered correction bolus dose is a divided portion of the calculated correction bolus dose of insulin.

15. The method of claim 1, comprising providing coordination between the second non-fasting insulin management modality and the first delivery device to the user.

16. The method of claim 15, wherein the coordination comprises providing one or more recommendations to the user relating to the non-fasting insulin management modality and/or the first delivery device.

17. The method of claim 15, wherein the coordination comprises providing one or more predictions to the user relating to a hypothetical use of the non-fasting insulin management modality and/or the first delivery device.

18. The method of claim 16, wherein the one or more recommendations comprise at least one of:

a recommendation for the user to utilize the first delivery device for a recommended timeframe at night; and a recommendation for the user to adjust daily basal doses of insulin from a current value to a different value.

19. The method of claim 17, wherein the one or more predictions comprise one or more of:

a prediction of waking blood glucose levels for the user based on an assumption that the user utilizes the first delivery device for a recommended timeframe at night;

a prediction of waking blood glucose levels for the user based on an assumption that the user adjusts daily basal doses of insulin from a current value to a different value; and a prediction of waking blood glucose levels for the user based on an assumption that the user does not utilize the first delivery device for an entire night.

20. The method of claim 15, wherein the coordination comprises:

coordinating a fast-ending procedure for the user, wherein coordinating the fast-ending procedure comprises:

receiving information relating to a fast-breaking meal that requires a meal bolus;

dividing a fast-ending meal bolus into a first portion equal to a remaining insulin in the first delivery device at the end of the fasting period and a second portion to be delivered to the user utilizing the non-fasting insulin management modality in a next non-fasting period immediately following the fasting period; and providing the user with instructions to deliver the second portion of the fast-ending meal bolus dose from the non-fasting insulin management modality.

21. An insulin management system comprising a first insulin delivery device attachable to a user's body for a duration of a fasting period within an overall time period, the first insulin delivery device comprising:

a delivery component configured to;

project a downward trend of a plurality of received blood glucose measurements and add the downward trend to one of the plurality of received blood glucose measurements to obtain an evaluated blood glucose measurement, calculate a correction bolus dose of insulin by comparing the evaluated blood glucose measurement to a target blood glucose to obtain a difference, adjusting the difference by a user insulin sensitivity factor to obtain a resultant insulin dose amount, and compensating the resultant insulin dose amount by a determined insulin on board, and deliver the calculated correction bolus dose of insulin as a plurality of delivered correction bolus doses of insulin from the first insulin delivery device during the fasting period, wherein the delivery component is not configured to deliver basal insulin, and wherein at least one of a basal dose of insulin and a meal bolus dose of insulin is received by the user from a second non-fasting insulin management modality during a non-fasting period within the overall time period.

22. The system of claim 21, wherein the user insulin sensitivity factor is derived from a total daily basal insulin dose information received from the second non-fasting insulin management modality in a defined period prior to the fasting period.

23. The system of claim 21, wherein the delivery component includes an initializing component configured to, at a start of the delivery from the first insulin delivery device, determine an assumed insulin on board as an amount of insulin needed to correct the evaluated blood glucose value to the target blood glucose.

24. The system of claim 21, wherein the delivery component includes a processor and a memory configured to provide non-transitory, computer-readable program instructions to the processor to execute functions of the components.

25. The system of claim 21, including a mobile user computing device comprising:

a processor and a memory configured to provide non-transitory, computer-readable program instructions to the processor to execute functions of one or more components of the mobile user computing device;

a basal insulin input component for requesting a value from a user of a total daily basal insulin dose information used in a defined period prior to the fasting period; and a controller pairing component for pairing the mobile user computing device to a controller of the first insulin delivery device.

26. An automatic insulin delivery device attachable to a user's body for a duration of a fasting period, the delivery device comprising:

a durable portion including a delivery component configured to;

project a downward trend of a plurality of received blood glucose measurements and add the downward trend to one of the plurality of received blood glucose measurements to obtain an evaluated blood glucose measurement, and calculate a correction bolus dose of insulin by comparing the evaluated blood glucose measurement to a target blood glucose to obtain a difference, adjusting the difference by a user insulin sensitivity factor to obtain a resultant insulin dose amount, and compensating the resultant insulin dose amount by a determined insulin on board; and a disposable portion including a reservoir configured to contain insulin and configured to deliver the calculated correction bolus dose of insulin as a plurality of delivered correction bolus doses of insulin to the user during the fasting period under control of the delivery component.

27. The delivery device of claim 26, wherein the reservoir is configured to be fillable from a non-fasting insulin injection device used during a non-fasting period.

* * * * *